United States Patent [19]

Levitt

[11]  4,169,719

[45]  Oct. 2, 1979

[54] HERBICIDAL SULFONAMIDES

[75] Inventor: George Levitt, Wilmington, Del.

[73] Assignee: E. I. Du Pont de Nemours and Co., Wilmington, Del.

[21] Appl. No.: 840,389

[22] Filed: Oct. 6, 1977

Related U.S. Application Data

[63] Continuation-in-part of Ser. No. 769,913, Feb. 23, 1977, abandoned, which is a continuation-in-part of Ser. No. 674,668, Apr. 7, 1976, abandoned.

[30] Foreign Application Priority Data

Apr. 6, 1977 [NZ] New Zealand .......................... 183821

[51] Int. Cl.$^2$ ........................ A01N 9/22; C07D 239/32
[52] U.S. Cl. ..................................... 71/92; 260/347.2; 544/320; 544/331; 544/332
[58] Field of Search ...................... 260/256.5 R; 71/92

[56] References Cited

FOREIGN PATENT DOCUMENTS 1468747  2/1967  France.

OTHER PUBLICATIONS

Wojciechowski, J. Acta. Polon. Pharm. 19, pp. 121-125 (1962).
Abbott; R. E., "Proceedings of the Northeastern Weed Control Conference," vol. 19, pp. 18-23 (1966).
Logemann et al., Chem. Abs., 53, 18052g (1959).

*Primary Examiner*—Donald G. Daus
*Assistant Examiner*—Lisa Jones

[57]  ABSTRACT

N-(heterocyclicaminocarbonyl)arylsulfonamides, such as N-[(4,6-dimethylpyrimidin-2-yl)aminocarbonyl]benzenesulfonamide, are useful for the regulation of plant growth and as herbicides, particularly for controlling nutsedge.

126 Claims, No Drawings

HERBICIDAL SULFONAMIDES

CROSS-REFERENCE TO RELATED APPLICATIONS

This application is a continuation-in-part of my U.S. application Ser. No. 769,913, filed Feb. 23, 1977, now abandoned which is a continuation-in-part of my U.S. application Ser. No. 674,668, filed Apr. 7, 1976, now abandoned.

BACKGROUND OF THE INVENTION

This invention relates to N-(heterocyclicaminocarbonyl)arylsulfonamide agricultural chemicals.

French Pat. No. 1,468,747 discloses the following para-substituted phenylsulfonamides, useful as antidiabetic agents:

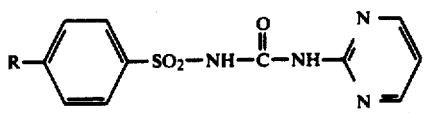

wherein R=H, halogen, CF₃ or alkyl.

Logemann et al. Chem. Ab., 53, 18052 g (1959), disclose a number of sulfonamides, including uracil derivatives and those having the formula:

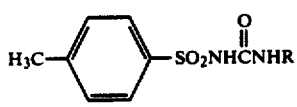

wherein R is butyl, phenyl or

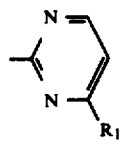

and $R_1$ is hydrogen or methyl. When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

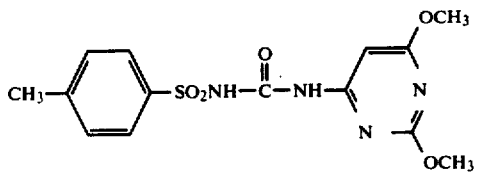

Based upon similarity to a known compound, the author predicted hypoglycemic activity for the foregoing compound.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Preventing or minimizing the loss of a portion of such valuable crops by killing, or inhibiting the growth of undesired vegetation is one way of improving this efficiency.

A wide variety of materials useful for killing or inhibiting (controlling) the growth of undesired vegetation is available; such materials are commonly referred to as herbicides. However, the need still exists for effective herbicides that destroy or control weeds while not significantly damaging useful crops. Some weeds (nutsedge is a particular example) are very difficult to control; many of the herbicides that are used to control nutsedge are so nonselective that they cause damage to the crops themselves.

SUMMARY OF THE INVENTION

According to this invention, there are provided novel compounds of Formula I and their agriculturally suitable salts, suitable agricultural compositions containing them, and methods of using them as selective, as well as general herbicides having both preemergence and postemergence activity. These compounds are highly active herbicides. They are especially useful in controlling nutsedge, yet cause minimal damage to desired crops, such as cotton, rice, corn, wheat, and the like.

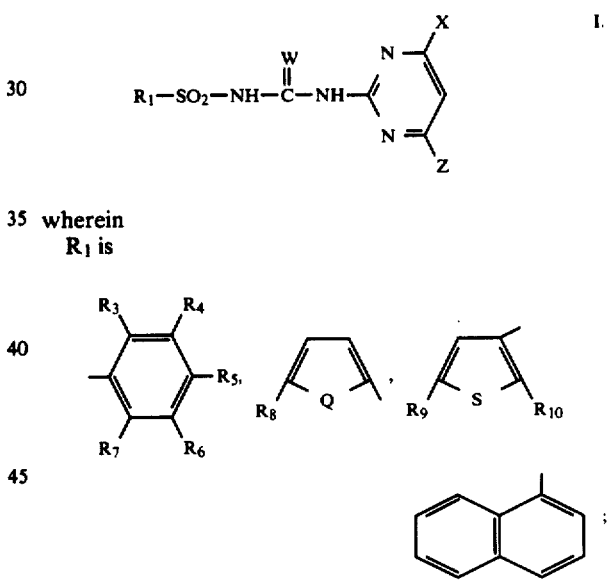

wherein
$R_1$ is $R_3$ and $R_6$ are independently hydrogen, fluorine, chlorine, bromine, iodine, alkyl of 1-4 carbon atoms, alkoxy of 1-4 carbon atoms, nitro, trifluoromethyl, cyano, $CH_3S(O)_n-$ or $CH_3CH_2S(O)_n-$;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1-2 carbon atoms or alkoxy of 1-2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1-3 carbon atoms, trifluoromethyl, $CH_3S-$ or $CH_3OCH_2-$; and Z is methyl or methoxy;
or their agriculturally suitable salts;
provided that:
(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;
(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and
(c) when $R_3$ and $R_7$ are both hydrogen at least one of $R_4$, $R_5$ or $R_6$ must be hydrogen.

Preferred in order of increasing preference based on activity or cost or both are
(1) those compounds of Formula I, defined above, wherein $R_1$ is

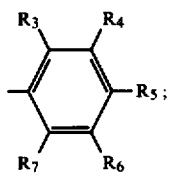

(2) compounds of preference (1) wherein
$R_3$ is hydrogen, fluorine, chlorine, bromine, alkyl of 1-4 carbon atoms, alkoxy of 1-4 carbon atoms, $CH_3S-$, $CH_3CH_2S-$ or nitro; and
$R_5$ is hydrogen, fluorine, chlorine, bromine or methyl; and
$R_6$ is hydrogen, fluorine, chlorine, bromine, alkyl of 1-4 carbon atoms, alkoxy of 1-4 carbon atoms, trifluoromethyl, nitro, $CH_3S-$ or $CH_3CH_2S-$;
provided that:
(a) when $R_5$ is other than hydrogen, $R_3$, $R_6$ or $R_7$ must independently be hydrogen, fluorine, chlorine, bromine, methyl or methoxy, and $R_4$ must be hydrogen, fluorine, chlorine, bromine or methyl;
(3) compounds of preference (2) wherein X is methyl or alkoxy having 1-3 carbon atoms; and Z is methyl or methoxy;
(4) compounds of preference (3) wherein
$R_3$ is hydrogen, fluorine, chlorine, bromine, alkyl of 1-2 carbon atoms, alkoxy of 1-2 carbon atoms, $CH_3S-$, $CH_3CH_2S-$ or nitro; and
$R_4$, $R_5$ and $R_7$ are independently hydrogen, fluorine, chlorine or methyl; and
$R_6$ is hydrogen, fluorine, chlorine, bromine, alkyl of 1-2 carbon atoms, alkoxy of 1-2 carbon atoms, trifluoromethyl, nitro, $CH_3S-$, or $CH_3CH_2S-$;
(5) compounds of preference (3) wherein $R_3$, $R_4$, $R_5$, $R_6$ and $R_7$ are independently hydrogen, fluorine, chlorine or methyl;
(6) compounds of preference (3) wherein
$R_3$ is fluorine, chlorine or methyl; and
$R_4$, $R_5$, $R_6$ and $R_7$ are independently hydrogen, fluorine, chlorine or methyl;
provided that:
when $R_5$ is other than hydrogen, $R_4$ and $R_6$ must be hydrogen;
(7) compounds of preference (3) wherein
$R_3$ is fluorine, chlorine or methyl; and
$R_4$ and $R_6$ are hydrogen; and
$R_5$ and $R_7$ are independently hydrogen, fluorine, chlorine or methyl;
(8) compounds of preference (3) wherein
$R_3$ is hydrogen, fluorine, chlorine, bromine, alkyl of 1-4 carbon atoms, alkoxy of 1-4 carbon atoms, $CH_3S-$, or $CH_3CH_2S-$; and
$R_4R_5$ and $R_7$ are hydrogen; and
$R_6$ is hydrogen, fluorine, chlorine, bromine, alkyl of 1-4 carbon atoms, alkoxy of 1-4 carbon atoms, trifluoromethyl, nitro, $CH_3S-$ or $CH_3CH_2S$;
(9) compounds of preference (8) wherein
$R_3$ is fluorine, chlorine, bromine, alkyl of 1-2 carbon atoms or alkoxy of 1-2 carbon atoms; and
$R_6$ is hydrogen, fluorine, chlorine, bromine, alkyl of 1-2 carbon atoms, alkoxy of 1-2 carbon atoms, trifluoromethyl or nitro; and
(10) compounds of preference (8) wherein
$R_3$ is fluorine, chlorine, bromine, methyl or methoxy; and
$R_6$ is hydrogen, fluorine, chlorine, bromine, methyl, methoxy or nitro; and
(11) compounds of preference (4) wherein $R_3$ is nitro and each of $R_4$, $R_5$, $R_6$ and $R_7$ is hydrogen.

Also, preferred in order of increasing preference based on activity or cost or both are:
(A) those compounds of Formula I, defined above, wherein
$R_1$ is

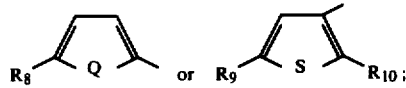

(B) compounds of preference (A) wherein Q is sulfur; X is methyl or alkoxy of 1-3 carbon atoms; and Z is methyl or methoxy;
(C) compounds of preference (A) wherein $R_1$ is

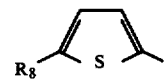

and $R_8$ is hydrogen.

Similarly, preferred based on activity are those compounds of Formula I, defined above, wherein
(1) $R_1$ is

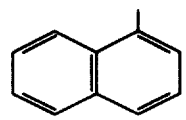

and W is oxygen.

Specifically, preferred for their outstanding activity or highly favorable cost or both are:
(1) N-[(4-methoxy-6-methylpyrimidin-2-yl)aminocarbonyl]-2-chlorobenzenesulfonamide, m.p. 194°–196° C.;
(2) N-[(4,6-dimethoxypyrimidin-2-yl)aminocarbonyl]-2,5-dichlorobenzenesulfonamide, m.p. 189°–190° C.;
(3) N-[(4-methoxy-6-methylpyrimidin-2-yl)aminocarbonyl]-2-methylbenzenesulfonamide, m.p. 172°–174° C.;
(4) N-[(4,6-dimethylpyrimidin-2-yl)aminocarbonyl]-2-thiophenesulfonamide, m.p. 224°–228° C.;

(5) N-[(4-methoxy-6-methylpyrimidin-2-yl)aminocarbonyl]-2-nitrobenzenesulfonamide, m.p. 223°–225° C.;

(6) N-[(4,6-dimethylpyrimidin-2-yl)aminocarbonyl]-2-nitrobenzenesulfonamide, m.p. 210°–212° C.(d);

(7) N-[(4,6-dimethoxypyrimidin-2-yl)aminocarbonyl]-2-nitrobenzenesulfonamide, m.p. 219°–220° C.; and (8) N-[(4-chloro-6-methylpyrimidin-2yl)aminocarbonyl]-2-nitrobenzenesulfonamide, m.p. 170°–172° C.

While all of the compounds of Formula I are herbicidal, not all of them are selective on all crops. However, by selecting particular compounds, weed control and crop safety can be obtained. Thus, some compounds show particular selectivity for control of weeds in wheat and rice; nutsedge control in crop such as corn, cotton, soybeans or rice; and water hyacinth control. In addition, the compounds of Formula I are useful plant growth regulants, e.g. increasing sugar content in sugarcane and sorghum and suppressing seedhead formation in grasses such as Bahia grass.

Specifically, preferred (A) for selective control of weeds in wheat is:
(1) N-[(4-methoxy-6-methylpyrimidin-2-yl)aminocarbonyl]-2-chloro-5-methoxybenzenesulfonamide, m.p. 199°–200° C.;

(B) for their selective control of nutsedge in crops are:
(1) N-[(4,6-dimethoxypyrimidin-2-yl)aminocarbonyl]-2,5-dichlorobenzenesulfonamide, m.p. 189°–190° C.; and
(2) N-[(4,6-dimethylpyrimidin-2-yl)aminocarbonyl]-2,6-dichlorobenzenesulfonamide, m.p. 177°–182° C.;

(C) for water hyacinth control is:
(1) N-[4-methoxy-6-methylpyrimidin-2-yl)aminocarbonyl]-2-chlorobenzenesulfonamide, m.p. 194°–196° C.;

(D) for growth regulant use are:
(1) N-[4,6-dimethylpyrimidin-2-yl)aminocarbonyl]-benzenesulfonamide, m.p. 228°–230° C.; and
(2) N-[(4,6-dimethoxypyrimidin-2-yl)aminocarbonyl]-2,5-dichlorobenzenesulfonamide, m.p. 189°–190° C.

(E) for selective control of weeds in rice are:
(1) N-[(4-methylpyrimidin-2-yl)aminocarbonyl]-2-chlorobenzenesulfonamide; m.p. 201°–203° C.; and
(2) N-[(4,6-dimethoxypyrimidin-2-yl)aminocarbonyl]-2,5-dibromobenzenesulfonamide; m.p. 201°–204° C.

Synthesis

As shown in Equation 1, the compounds of Formula I can be prepared by reacting an appropriate 2-amino pyrimidine of Formula III with an appropriately substituted sulfonyl is isocyanate or isothiocyanate of Formula II; $R_1$, W, X and Z being as previously defined.

$$R_1SO_2NCW + NH_2-\underset{(III)}{\text{pyrimidine}} \longrightarrow \underset{(I)}{R_1SO_2NHCNH-\text{pyrimidine}}$$

Equation 1.

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate or isothiocyanate to a stirred suspension of the aminopyrimidine. Since such isocyanates and isothiocyanates usually are liquids, their addition can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether, and filtration.

In certain cases, it may be possible to obtain isomeric products from the reaction shown in Equation 1. Such isomeric products would result from addition of compound II to an endocyclic nitrogen atom of 2-aminopyrimidine III and have a structure as exemplified below:

It is to be understood that reaction products resulting from the addition of a compound of Formula II to the exocyclic as well as the endocyclic nitrogen atoms of 2-aminopyrimidine III are to be considered a part of this invention.

The intermediate sulfonyl isocyanates of Formula II (wherein W is O) can be prepared by reacting corresponding sulfonamides with phosgene in the presence of n-butyl isocyanate at reflux in a solvent such as chlorobenzene, according to the procedure of H. Ulrich and A. A. Y. Sayigh, *Newer Methods of Preparative Organic Chemistry*, Vol. VI p 223–241, Academic Press, New York and London. W. Foerst Ed.

The preparation of sulfonamides from ammonium hydroxide and sulfonyl chlorides is widely reported in the literature, e.g. Crossley et al., *J. Am. Chem. Soc.* 60, 2223 (1938). The preparation of 2-furansulfonamide is described in *J. Org. Chem.* 18 894 (1953).

Certain sulfonyl chlorides are best prepared by chlorosulfonation of a substituted benzene, naphthalene, or thiophene in carbon tetrachloride according to the teaching of H. T. Clarke et al. *Org. Synth. Coll.* Vol 1, 2nd Ed. 1941, p 85. Other benzenesulfonyl chlorides are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, *J. Org. Chem.* 25 1824 (1960).

Furansulfonylchlorides are best prepared as shown in Equation 2.

Equation 2.

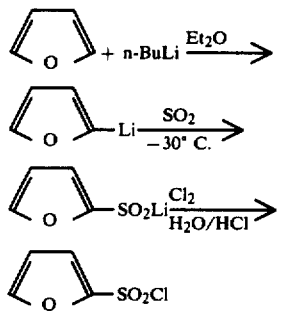

Sulfonyl isothiocyanates can be prepared by treatment of sulfonamides with carbon disulfide and potassium hydroxide followed by reaction of the dipotassium salt with phosgene according to the teaching of K. Hartke, *Arch. Pharm.*, 299, 174 (1966).

The synthesis of heterocyclic amine derivatives has been reviewed in "*The Chemistry of Heterocyclic Compounds,*" a series published by Interscience Publ., New York and London. 2-Aminopyrimidines are described by D. J. Brown in "The Pyrimidines," Vol. XVI of the above series.

Agriculturally suitable salts of compounds of Formula I are also useful herbicides and can be prepared by a number of ways known to the art. For example, metal salts can be made by treating compounds of Formula I with a solution of an alkali or alkaline earth metal salt having a sufficiently basic anion (e.g. hydroxide, alkoxide, carbonate or hydride). Quaternary amine salt can be made by similar techniques.

Salts of compounds of Formula I can also be prepared by exchange of one cation for another. Cationic exchange can be effected by direct treatment of an aqueous solution of a salt of a compound of Formula I (e.g. alkali metal or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g. an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water soluble.

Acid addition salts, useful in this invention, can be obtained by reacting a compound of Formula I with a suitable acid, e.g. p-toluenesulfonic acid, trichloroacetic acid or the like.

The compounds of this invention and their preparation are further illustrated by the following examples wherein temperatures are given in degrees centrigrade.

EXAMPLE 1

N-[(4,6-Dimethylpyrimidin-2-yl)ainocarbonyl]benzenesulfonamide

To a dry, well-stirred mixture of 12.4 g of 2-amino-4,6-dimethylpyrimidine in 250 ml of methylene chloride at ambient temperature and pressure was added dropwise 18.3 g of benzenesulfonyl isocyanate. The resulting mixture was stirred for two hours and the precipitated product removed by filtration. After being washed with 1-chlorobutane, the product melted at 228°-230° and showed characteristic absorption bands in the infrared spectrum at 1710 cm$^{-1}$, 1620 cm$^{-1}$, and 1550 cm$^{-1}$. The product was N-[(4,6-dimethylpyrimidin-2-yl)aminocarbonyl]benzenesulfonamide.

EXAMPLE 2

N-[(4-methoxy-6-methylpyrimidin-2-yl)aminocarbonyl]-2-chlorobenzenesulfonamide

To a suspension of 280 g of 2-amino-4-methoxy-6-methylpyrimidine in 2000 ml of methylene chloride was added 434 g of 2-chlorobenzenesulfonyl isocyanate with stirring. The resultant mixture was stirred for 16 hours, cooled to 10° and filtered to yield 470 g of a solid melting at 195°-196°. Mass spectrographic analysis showed this product to have a molecular weight of 356.

Analysis-Calculated for $C_{13}H_{13}ClN_4O_4S$: C, 43.89%; H, 3.40%; N, 15.75%;

Found: C, 43.47%; H, 3.56%; N, 15.30%.

This product was N-[(4-methoxy-6-methylpyrimidin-2-yl)aminocarbonyl]-2-chlorobenzenesulfonamide.

Partial evaporation of the filtrate caused precipitation of 20 g of by-product material melting at 160°-162°. The infrared absorption spectrum of the by-product was similar to the first precipitate, and it had a molecular weight of 356.

Analysis-Calculated for $C_{13}H_{13}ClN_4O_4S$: C, 43.89%; H, 3.40%; N, 15.75%;

Found: C, 44.09%; H, 3.56%; N, 14.97%.

By using an equivalent amount of an appropriate 2-aminopyrimidine and an appropriately substituted benzenesulfonyl isocyanate, the following compounds of Formula I can be prepared by the procedure of Examples 1 or 2;

TABLE I-A

| $R_3$ | $R_4$ | $R_5$ | $R_6$ | $R_7$ | m.p. |
|---|---|---|---|---|---|
| H | H | H | H | H | 228-230 |
| F | H | H | H | H | 218-219 |
| $CH_3$ | H | H | H | H | 195-196 |
| Cl | H | H | H | H | 204-205 |

TABLE I-A-continued

Structure: R5, R6, R7, R4, R3 substituted phenyl-SO2NHC(O)NH-pyrimidine (with 4,6-dimethyl pyrimidine)

| R3 | R4 | R5 | R6 | R7 | m.p. |
|---|---|---|---|---|---|
| H | H | H | NO2 | H | 193-196 |
| H | H | H | CF3 | H | 183(d) |
| H | Cl | H | H | H | 142-143 |
| —CF3 | H | H | H | H | 218-220 |
| NO2 | H | H | H | H | 210-212 |
| Cl | H | H | —SOCH3 | H | — |
| Cl | H | H | —SOC2H5 | H | — |
| CH3O— | H | CH3O— | H | H | 198-199 |
| Cl | H | H | NO2 | H | — |
| CH3 | H | H | NO2 | H | 191-192 |
| CH3 | H | H | —CH(CH3)2 | H | 157-160 |
| CH3 | H | H | Cl | H | 209-211 |
| Cl | H | H | CH3 | H | 211-213 |
| F | H | H | F | H | 189-190 |
| I | H | H | CH3 | H | — |
| CH3S— | H | H | NO2 | H | — |
| CH3O— | H | H | CH3 | H | 193-194 |
| Cl | H | H | H | CH3 | 230-232 |
| Cl | H | H | H | Cl | 177-182 |
| F | H | H | H | F | 208-211 |
| Cl | Cl | Cl | H | H | 215-217 |
| Cl | H | Cl | Cl | H | 204-205 |
| —CH(CH3)2 | H | Cl | —CH(CH3)2 | H | 131-136 |
| n-C4H9O | H | H | n-C4H9O | H | |
| n-C4H9 | H | H | n-C4H9 | H | |
| CN | H | H | CN | H | |
| C2H5SO2— | H | H | H | H | |
| CH3SO2— | H | H | H | H | |
| CH3 | H | CH3 | H | CH3 | 227-231(d) |
| F | H | F | H | F | 173-180 |
| Cl | H | Cl | H | Cl | 208-210 |
| CH3O— | H | CH3O— | H | CH3O— | 192-193 |
| Cl | Cl | H | Cl | Cl | 220-222 |
| CH3 | CH3 | H | CH3 | CH3 | 244-246 |
| Cl | Cl | H | H | H | 195-197 |
| Cl | CH3 | H | H | H | 196-199 |
| CH3O— | Cl | H | H | H | 179-180 |
| F | Cl | H | H | H | 196-197 |
| CH3 | Cl | H | H | H | 208-209 |
| Br | H | Br | H | Br | — |
| Cl | H | Cl | H | H | 202-205 |
| F | H | Cl | H | H | 202-203 |
| —SOCH3 | H | H | H | H | — |
| H | Cl | Cl | H | H | 210-212 |
| Cl | F | H | H | H | — |
| H | Cl | H | Cl | H | 199-202 |
| F | H | H | CH3 | H | 210-212 |
| CH3 | H | H | F | H | 200-201 |
| Cl | H | H | CH3O— | | 198-199 |
| Br | H | H | Br | H | 211-212 |
| CH3O— | H | H | CH3O— | H | 193-195 |
| CH3 | H | H | CH3 | H | 204-205 |
| CH3 | H | H | Br | H | 205-207 |
| C2H5O— | H | H | C2H5O— | H | 208-210 |
| CH3O— | H | H | F | H | 199-201 |
| Cl | H | H | Cl | H | 212-213 |
| H | Br | H | I | H | |
| H | H | H | CH3S— | H | |
| H | H | H | C2H5SO2— | H | |
| CH3O— | H | H | Cl | H | 209-210 |

TABLE I-B

R_3, R_4, R_5, R_6, R_7 substituents on aryl sulfonylurea with 4-methoxy-6-methylpyrimidine.

| R_3 | R_4 | R_5 | R_6 | R_7 | m.p. |
|---|---|---|---|---|---|
| H | H | H | H | H | 204–205 |
| H | CH_3 | H | H | H | 149–151 |
| Br | H | H | H | H | 210–211 |
| F | H | H | H | H | 198–199 |
| CH_3 | H | H | H | H | 172–174 |
| CN | H | H | H | H | — |
| —SO_2CH_3 | H | H | H | H | 170–171 |
| H | H | Br | NO_2 | H | — |
| H | H | Cl | H | H | 151–153 |
| H | H | H | CF_3 | H | 150–152 |
| H | H | F | CN | H | — |
| H | H | H | —SO_2CH_3 | H | — |
| H | H | H | —SO_2C_2H_5 | H | — |
| Cl | Cl | H | H | H | 199–200 |
| Cl | CH_3 | H | H | H | 177–186 |
| CH_3O— | Cl | H | H | H | 190–193 |
| CH_3 | Cl | H | H | H | 190–192 |
| F | Cl | H | H | H | 193–195 |
| Cl | F | H | H | H | — |
| CH_3 | Br | H | H | Br | — |
| C_2H_5 | H | H | H | C_2H_5 | — |
| H | Cl | H | Cl | C_2H_5O— | — |
| H | Cl | H | H | H | 193–195 |
| n-C_4H_9O— | H | H | n-C_4H_9O— | H | 182–183 |
| F | H | Cl | H | H | 206–208 |
| I | H | H | H | H | — |
| NO_2 | H | H | H | H | 223–225 |
| CF_3 | H | H | H | H | 194–197 |
| Cl | H | F | H | H | 199–201 |
| Cl | H | Cl | H | H | 195–197 |
| Cl | H | CH_3O | H | H | — |
| H | Cl | H | Cl | H | 207–211 |
| H | CH_3 | CH_3 | H | H | 193–196 |
| C_2H_5S— | H | H | NO_2 | H | — |
| F | H | H | F | H | 177–178 |
| CH_3O— | H | H | Cl | H | 199–200 |
| CH_3 | H | H | Cl | H | 206–207 |
| C_2H_5O— | H | H | C_2H_5O— | H | 175–177 |
| Cl | H | H | CH_3 | H | 197–200 |
| CH_3 | H | H | NO_2 | H | 194–195 |
| CH_3 | H | H | —CH(CH_3)_2 | H | 136–142 |
| Cl | H | H | NO_2 | H | 178–180 |
| CH_3 | H | H | CH_3 | H | 174–176 |
| CH_3 | H | H | Br | H | 195–197 |
| Br | H | H | Br | H | 207–209 |
| CH_3O— | H | H | CH_3O— | H | 175–177 |
| Cl | H | H | Cl | H | 174–179 |
| F | H | H | CH_3 | H | 207–208 |
| CH_3 | H | H | F | H | 173–175 |
| Cl | H | H | CH_3O— | H | 199–200 |
| C_2H_5 | H | H | C_4H_9 | H | — |
| C_4H_9 | H | H | C_2H_5 | H | — |
| CH_3O— | H | H | CH_3 | H | 180–182 |
| F | H | H | H | F | 192–195 |
| Cl | H | H | H | Cl | 148–153 |
| Cl | H | H | H | CH_3 | 166–170 |
| C_2H_5SO_2— | H | H | H | H | — |
| CH_3S— | H | H | H | H | — |
| C_2H_5O— | H | H | Cl | H | 180–183 |
| Cl | H | H | —SOCH_3 | | — |
| Cl | H | H | —SOC_2H_5 | | — |
| Cl | Cl | Cl | H | H | 186–187 |
| Cl | H | Cl | Cl | H | 189–190 |
| CH_3 | H | CH_3 | H | CH_3 | 203–205 |
| F | H | F | H | F | 197–199 |
| Cl | H | Cl | H | Cl | 181–186 |
| CH_3O— | H | CH_3O— | H | CH_3O | 185–187 |
| Cl | Cl | H | Cl | Cl | 215–218 |
| CH_3 | CH_3 | H | CH_3 | CH_3 | 223–226 |
| CH_3O | Cl | H | Cl | H | 181–183 |
| CH_3 | H | H | NO_2 | H | 182–183.5 |

TABLE I-C

R_3, R_4, R_5, R_6, R_7 substituents on aryl sulfonylurea with 4,6-dimethoxypyrimidine.

| R_3 | R_4 | R_5 | R_6 | R_7 | m.p. |
|---|---|---|---|---|---|
| H | H | H | H | H | 202–203 |
| F | H | H | H | H | 200–201 |
| Cl | H | H | H | H | 179–181 |
| CH_3 | H | H | H | H | 184–186 |
| SO_2C_2H_5 | H | H | H | H | — |
| H | H | H | NO_2 | H | — |
| H | Cl | H | H | H | >250 |
| H | H | H | CF_3 | H | 190–191 |
| Cl | H | H | CH_3S— | H | — |
| Cl | H | H | C_2H_5S— | H | — |
| CH_3O— | Cl | H | H | H | 183–184 |
| F | H | Cl | H | H | 244–245 |
| F | H | H | Cl | H | 223–224 |
| Cl | H | F | H | H | 203–205 |
| Cl | H | Cl | H | H | 190–191 |
| —SOC_2H_5 | H | H | NO_2 | H | — |
| CH_3O— | H | CH_3O— | H | H | 182–184 |
| CH_3O— | H | H | CH_3 | H | 227–229 |
| Cl | H | H | CF_3 | H | 161–162 |
| F | H | H | F | H | 210–212 |
| Br | H | H | Br | H | 201–204 |
| CH_3O— | H | H | CH_3O— | H | 198–199 |
| CH_3 | H | H | Br | H | 170–172 |
| Cl | H | H | NO_2 | H | 225–228 |
| Cl | H | H | CH_3O— | H | 180–181 |
| n-C_3H_7O— | H | H | n-C_3H_7O | H | 188–189 |
| n-C_4H_9O— | H | H | n-C_4H_9O— | H | 165–167 |
| C_2H_5O— | H | H | C_2H_5O— | H | 181–183 |
| CH_3O— | H | H | F | H | 192–194 |
| CH_3O— | H | H | Cl | H | 197–198 |
| Cl | H | H | Cl | H | 189–190 |
| CH_3 | H | H | Cl | H | 181–183 |
| Cl | H | H | CH_3 | H | 216–217 |
| CH_3 | H | H | NO_2 | H | 205–207 |
| CH_3 | H | H | —CH(CH_3)_2 | H | 110–116 |
| CH_3 | H | H | CH_3 | H | 187–189 |
| CH_3O— | H | H | I | H | — |
| CH_3O— | H | CH_3O— | H | H | 173–175 |
| Cl | H | H | H | CH_3 | 171–174 |
| CH_3 | H | H | H | CH_3 | 197–198 |
| F | H | F | H | F | 219–221 |
| Cl | H | Cl | H | Cl | 194–195 |
| CH_3O— | H | CH_3O— | H | CH_3O— | 180–181 |
| Cl | Cl | H | Cl | Cl | 223–224 |
| CH_3 | CH_3 | H | CH_3 | CH_3 | 182–184 |
| CF_3 | H | H | H | H | 219–220 |
| CH_3O | Cl | H | Cl | H | 183–185 |
| CH_3 | Cl | H | NO_2 | H | 207–209 |

TABLE I-D

| R_3 | R_4 | R_5 | R_6 | R_7 | X | m.p. |
|---|---|---|---|---|---|---|
| H | H | H | H | H | H | 187–189 |
| CH_3 | H | H | H | H | —CH_2OCH_3 | 157–158 |
| Cl | H | H | H | H | —CH_2OCH_3 | 179–180 |
| Cl | H | H | Cl | H | —CH_2OCH_3 | 174–176 |
| CH_3O— | H | H | CH_3O— | H | —CH_2OCH_3 | 155–157 |
| F | H | H | H | H | H | 192–193 |
| CH_3 | H | H | H | H | H | 211–213 |
| Cl | H | H | H | H | H | 201–203 |
| H | Cl | H | H | H | H | 198–199 |
| F | Cl | H | H | H | H | 219–220 |
| CH_3 | Cl | H | H | H | H | 211–213 |

TABLE I-D-continued $$R_5 \underset{R_4}{\overset{R_6}{\diagdown}} \underset{R_3}{\overset{R_7}{\diagup}} - SO_2\underset{H}{\overset{|}{N}}\overset{O}{\overset{||}{C}}NH - \underset{N}{\overset{N}{\diagdown}} \underset{X}{\overset{CH_3}{\diagup}}$$

| $R_3$ | $R_4$ | $R_5$ | $R_6$ | $R_7$ | X | m.p. |
|---|---|---|---|---|---|---|
| F | H | Cl | H | H | H | 222-235(d) |
| H | Cl | H | Cl | H | H | 201-203 |
| CH$_3$O— | H | H | Cl | H | H | 224-226 |
| Cl | H | H | Cl | H | H | 207-209 |
| CH$_3$ | H | H | Cl | H | H | 217-219 |
| F | H | H | F | H | H | 173-199 |
| Cl | H | H | H | Cl | H | 160-163 |
| H | H | H | H | H | C$_2$H$_5$O— | 180-182 |
| Cl | H | H | Cl | H | C$_2$H$_5$O— | — |
| CH$_3$ | H | H | Cl | H | C$_2$H$_5$O— | — |
| CH$_3$ | H | H | CH$_3$ | H | C$_2$H$_5$O— | — |
| H | H | H | H | H | (CH$_3$)$_2$CHO— | 116-120 |
| H | H | H | H | H | Cl | 213-215 |
| CH$_3$ | H | H | H | H | Cl | — |
| H | Cl | H | H | H | Cl | 194-195 |
| Cl | H | H | Cl | H | Cl | — |
| CH$_3$ | H | H | Cl | H | C$_2$H$_5$ | — |
| CH$_3$ | H | H | CH$_3$ | H | CH$_3$ | — |
| CH$_3$ | H | H | H | H | Br | — |
| Cl | H | H | H | H | Br | — |
| Cl | H | H | Cl | H | Br | — |
| H | H | H | H | H | CH$_3$S— | 208(d) |
| Cl | H | H | H | H | CH$_3$S— | — |
| CH$_3$ | H | H | H | H | CH$_3$S— | — |
| Cl | H | H | Cl | H | CH$_3$S— | — |
| CH$_3$ | H | H | CH$_3$ | H | CH$_3$S— | — |
| H | H | H | H | H | —CF$_3$ | 179-182 |
| CH$_3$ | H | H | H | H | —CF$_3$ | 172-174 |
| Cl | H | H | H | H | —CF$_3$ | 173-175 |
| H | H | H | —CF$_3$ | H | —CF$_3$ | 160-163 |
| Cl | H | H | Cl | H | —CF$_3$ | — |
| CH$_3$ | H | H | Cl | H | —CF$_3$ | — |
| CH$_3$ | H | H | CH$_3$ | H | —CF$_3$ | — |

TABLE I-E $$R_5 \underset{R_4}{\overset{R_6}{\diagdown}} \underset{R_3}{\overset{R_7}{\diagup}} - SO_2NH\overset{O}{\overset{||}{C}}NH - \underset{N}{\overset{N}{\diagdown}} \underset{X}{\overset{OCH_3}{\diagup}}$$

| $R_3$ | $R_4$ | $R_5$ | $R_6$ | $R_7$ | X | m.p. |
|---|---|---|---|---|---|---|
| H | H | H | H | H | H | 199-200(d) |
| H | H | H | H | H | —CH$_2$OCH$_3$ | — |
| CH$_3$ | H | H | H | H | —CH$_2$OCH$_3$ | — |
| H | H | H | H | H | Cl | 181-183 |
| Cl | H | H | H | H | Cl | 185-188 |
| CH$_3$ | H | H | H | H | Cl | 176-178 |
| Cl | H | H | Cl | H | Cl | — |
| CH$_3$ | H | H | CH$_3$ | H | Cl | — |
| H | H | H | H | H | CH$_3$S— | 194-196 |
| Cl | H | H | H | H | CH$_3$S— | — |
| CH$_3$ | H | H | H | H | CH$_3$S— | — |
| Cl | H | H | Cl | H | CH$_3$S— | — |
| CH$_3$ | H | H | Cl | H | CH$_3$S— | — |
| H | H | H | H | H | —CF$_3$ | 164-168 |
| Cl | H | H | H | H | —CF$_3$ | 204-208 |
| CH$_3$ | H | H | H | H | —CF$_3$ | 171-173 |
| H | H | H | —CF$_3$ | H | —CF$_3$ | 191-194 |
| Cl | H | H | Cl | H | —CF$_3$ | — |
| CH$_3$ | H | H | CH$_3$ | H | —CF$_3$ | — |
| H | H | H | H | H | C$_2$H$_5$O— | 163-165 |
| Cl | H | H | H | H | C$_2$H$_5$O— | 142-144 |
| CH$_3$ | H | H | H | H | C$_2$H$_5$O— | 148-149 |
| Cl | H | H | Cl | H | C$_2$H$_5$O— | — |
| CH$_3$ | H | H | CH$_3$ | H | C$_2$H$_5$O— | — |

EXAMPLE 3

N-[(4,6-dimethylpyrimidin-2-yl)aminocarbonyl]-2-thiophenesulfonamide

To 12 g of 2-amino-4,6-dimethylpyrimidine in 250 ml of acetonitrile was added, with stirring, 19 g of 2-thiophenesulfonyl isocyanate. The resulting mixture was stirred for 2 hours and filtered to yield the desired solid product, m.p. 215°-216°. The infrared spectrum for this product showed absorption peaks at 1540 cm$^{-1}$, 1605 cm$^{-1}$, and 1700 cm$^{-1}$.

EXAMPLE 4

N-[(4,6-dimethylpyrimidin-2-yl)aminocarbonyl]-2,5-dichloro-3-thiophenesulfonamide To a suspension of 12 g of 2-amino-4,6-dimethylpyrimidine in 300 ml of methylene chloride was added at ambient temperature 26 g of 2,5-dichloro-3-thiophenesulfonyl isocyanate. After stirring for 16 hours, the resulting solution was evaporated to dryness and the desired product, obtained as a solid residue, was triturated with ethyl ether and filtered. The solid product thus obtained melted at 192°-194° and showed infrared absorption peaks at 1550 cm$^{-1}$, 1605 cm$^{-1}$, and 1690 cm$^{-1}$.

EXAMPLE 5

N-[(4-methoxy-6-methylpyrimidin-2-yl)aminocarbonyl]-2-furansulfonamide

To a solution of 2.10 g of 2-furansulfonyl isocyanate in 40 ml of methylene chloride was added 1.60 g 2-amino-4-methoxy-6-methylpyrimidine. The resulting mixture was stirred for 1 hour at room temperature, then refluxed for 15 minutes, and the solvent was removed under vacuum. The solid obtained was allowed to stand under ethyl ether containing a trace of acetonitrile for one day, and was then filtered and dried to give the desired product melting at 185°-188° (dec).

By using an equivalent of an appropriate 2-aminopyrimidine and an appropriately substituted thiophene or furansulfonyl isocyanate, the following compounds of Table II can be prepared by the procedures of Examples 3-5:

TABLE II-A $$R_8 \underset{Q}{\diagdown}\diagup - SO_2NH\overset{O}{\overset{||}{C}} - NH - \underset{N}{\overset{N}{\diagdown}}\underset{Z}{\overset{X}{\diagup}} - H$$

| $R_8$ | Q | X | Z | m.p. |
|---|---|---|---|---|
| H | S | CH$_3$ | CH$_3$O— | 207-208 |
| H | S | CH$_3$O— | CH$_3$O— | 206-207 |
| Cl | S | CH$_3$ | CH$_3$O— | 186-187 |
| Cl | S | CH$_3$ | CH$_3$ | 198-199 |
| Cl | S | H | CH$_3$ | 197-198 |
| CH$_3$ | S | CH$_3$ | CH$_3$O— | |
| H | S | Cl | CH$_3$O— | |
| H | S | n-C$_3$H$_7$O | CH$_3$O— | |
| H | S | Br | CH$_3$O— | |
| H | S | CF$_3$ | CH$_3$O— | |
| H | S | CH$_3$S— | CH$_3$O— | |
| H | S | CH$_3$OCH$_2$— | CH$_3$ | |
| Cl | S | CH$_3$O— | CH$_3$O— | |
| Br | S | CH$_3$O— | CH$_3$O— | |
| CH$_3$ | S | CH$_3$O— | CH$_3$O— | |
| Br | S | CH$_3$ | CH$_3$O— | |
| Cl | S | CH$_3$ | CH$_3$ | |
| H | O | CH$_3$O— | CH$_3$O— | |

TABLE II-A-continued $$R_8-Q-SO_2NHC(=O)-NH-\text{pyrimidine}(X,Z,H)$$

| R8 | Q | X | Z | m.p. |
|---|---|---|---|---|
| H | O | CH₃ | CH₃ | |
| Br | S | CH₃ | CH₃ | |
| CH₃ | S | CH₃ | CH₃ | |

TABLE II-B $$R_9,R_{10}\text{-thiophene-}SO_2NHC(=O)NH-\text{pyrimidine}(X,Z,H)$$

| R9 | R10 | X | Z | m.p. |
|---|---|---|---|---|
| Cl | Cl | CH₃ | CH₃O— | 186–188 |
| Cl | Cl | CH₃O— | CH₃O— | 201–202 |
| CH₃ | CH₃ | CH₃ | CH₃ | |
| CH₃ | CH₃ | CH₃ | CH₃O— | |
| Br | Br | CH₃ | CH₃ | |
| CH₃ | Cl | CH₃ | CH₃ | |
| Br | Br | CH₃ | CH₃O— | |
| CH₃ | CH₃ | CH₃O— | CH₃O— | |
| H | H | CH₃ | CH₃O— | |

EXAMPLE 6

N-[(4,6-Dimethoxypyrimidin-2-yl)aminocarbonyl]-1-naphthalene sulfonamide

To a suspension of 15.6 g of 2-amino-4,6-dimethoxy pyrimidine in 400 ml of acetonitrile was added 23.3 g of 1-naphthalenesulfonyl isocyanate with stirring. After continued stirring for 14 hours, the desired solid product was removed by filtration, and after being washed with a small amount of ethyl ether, melted at 177°–178°.

By using an equivalent amount of an appropriate 2-aminopyrimidine and 1-naphthalenesulfonyl isocyanate, the following Formula I compounds can be prepared by the method of Example 6:

N-[(4-chloro-6-methylpyrimidin-2-yl)aminocarbonyl]-1-naphthalenesulfonamide, m.p. 205°–207°

N-[(4,6-dimethylpyrimidin-2-yl)aminocarbonyl]-1-naphthalenesulfonamide, m.p. 201°–202°

N-[(4-methylpyrimidin-2-yl)aminocarbonyl]-1-naphthalenesulfonamide, m.p. 182°–183°

N-[(4-methoxy-6-methylpyrimidin-2-yl)aminocarbonyl]-1-napthalenesulfonamide, m.p. 210°–211°.

EXAMPLE 7

N-[(4,6-Dimethylpyrimidin-2-yl)aminothioxomethyl]-benzenesulfonamide

To a dry suspension of 12.4 g of 2-amino-4,-6-dimethypyrimidine in 60 ml of acetonitrile was added 19.9 g of benzenesulfonyl isothiocyanate. The heavy white precipitate which formed was removed by filtration and washed with anhydrous ethyl ether. It melted at 165°170°. The product was N-[(4,6-dimethylpyrimidin-2-yl)-aminothioxomethyl]benzenesulfonamide.

By using an equivalent amount of the appropriate sulfonyl isothiocyanate and an appropriately substituted aminopyrimidine, the compound of Table III can be prepared by the procedure of Example 7:

TABLE III-A

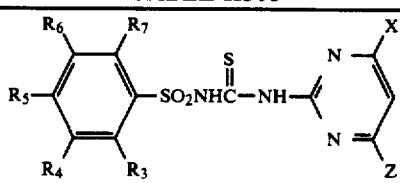

| R3 | R4 | R5 | R6 | R7 | X | Z | m.p. |
|---|---|---|---|---|---|---|---|
| H | H | H | H | H | CH₃ | CH₃O— | 188–189 |
| H | H | H | H | H | CH₃O | CH₃O | 192–193 |
| Cl | H | H | H | H | CH₃ | CH₃ | |
| C₂H₅SO₂ | H | H | CH₃SO₂ | H | CH₃ | CH₃O | |
| Cl | H | H | H | H | CH₃ | CH₃O— | 184–185 |
| Cl | H | H | H | H | CH₃O— | CH₃O— | 169–172 |
| Cl | H | H | Cl | H | CH₃ | CH₃ | |
| Cl | H | H | Cl | H | CH₃ | CH₃O— | |
| CH₃ | H | H | F | H | CH₃ | CH₃ | |
| CH₃ | H | H | H | H | CH₃ | CH₃O | 165–167 |
| CH₃ | H | H | H | H | CH₃O— | CH₃O— | 175–178 |
| Cl | H | H | H | Cl | CH₃ | CH₃O— | |
| CH₃O— | H | H | CH₃— | H | CH₃ | CH₃ | |
| CH₃O— | H | H | CH₃O— | H | CH₃ | CH₃O— | 178–180 |
| CH₃O— | H | H | CH₃O— | H | CH₃O— | CH₃O— | 191–193 |
| Cl | H | H | Cl | H | n-C₃H₇ | CH₃O— | |
| Cl | H | H | NO₂ | H | CH₃ | CH₃O— | |
| Cl | H | H | CF₃ | H | CH₃O— | CH₃O— | |
| Cl | H | H | NO₂ | H | CH₃ | CH₃ | |
| CH₃O— | H | H | Cl | H | CH₃ | CH₃O— | |
| CH₃O— | H | H | Cl | H | CF₃ | CH₃ | |
| Cl | H | Cl | H | H | CH₃S— | CH₃O— | |
| Cl | H | Cl | H | H | CH₃OCH₂— | CH₃O— | |
| C₂H₅O— | H | H | C₂H₅O— | H | CH₃O— | CH₃ | |
| CH₃ | H | CH₃ | H | CH₃O | CH₃ | CH₃O— | |

TABLE III-A-continued

Structure: R5, R6 on one side, R4, R3 on other, R7 at top, with SO2NHC(S)NH-pyrimidine bearing X and Z

| R3 | R4 | R5 | R6 | R7 | X | Z | m.p. |
|---|---|---|---|---|---|---|---|
| CH3 | H | CH3 | H | CH3 | CH2CH3 | CH3 | |
| CH3 | H | CH3 | H | CH3 | CH3O— | CH3O— | |
| H | H | H | CF3 | H | CH3 | CH3O— | |
| CH3 | F | H | NO2 | H | H | CH3O— | |
| CH3 | F | F | NO2 | H | H | CH3O— | |
| n-C4H9 | H | H | n-C4H9 | H | Cl | CH3 | |
| n-C4H9O— | H | H | n-C4H9O— | H | Br | CH3O— | |
| F | Cl | Cl | H | H | CH3O— | CH3O— | |
| CH3 | H | H | Cl | F | CH3O— | CH3O— | |
| NO2 | H | H | H | Br | CH3O— | CH3O— | |
| Cl | H | H | Cl | H | CH3O— | CH3O— | |
| I | CH3 | H | I | H | CH3O— | CH3O— | |
| CF3 | H | F | H | H | CH3O— | CH3O— | |
| CN | H | CH3O— | CN | H | CH3O— | CH3O— | |
| CH3S— | H | H | CH3S— | H | CH3O— | CH3O— | |

TABLE III-B

Structure: R8-thiophene-SO2NHC(S)NH-pyrimidine(X,Z)

| R8 | X | Z | m.p. |
|---|---|---|---|
| H | CH3 | CH3 | |
| H | CH3 | CH3O— | 196–197 |
| H | CH3O— | CH3O— | 202–204 |
| Cl | CH3 | CH3 | |
| Cl | CH3 | CH3O— | |
| Cl | CH3O— | CH3O— | |
| CH3 | CH3 | CH3 | |
| CH3 | CH3 | CH3O— | |
| CH3 | CH3O— | CH3O— | |
| Br | CH3 | CH3 | |
| Br | CH3 | CH3O— | |
| Br | CH3O— | CH3O— | |

TABLE III-C

Structure: R9, R10 substituted thiophene-SO2NHC(S)NH-pyrimidine(X,Z)

| R9 | R10 | X | Z |
|---|---|---|---|
| CH3 | CH3 | CH3 | CH3 |
| CH3 | CH3 | CH3 | CH3O— |
| CH3 | CH3 | CH3O— | CH3O— |
| Cl | Cl | CH3 | CH3 |
| Cl | Cl | CH3 | CH3O— |
| Cl | Cl | CH3O— | CH3O— |
| H | H | CH3 | CH3O— |
| Br | Br | CH3 | CH3O— |

EXAMPLE 8
2-Furansulfonylisocyanate

Reaction scheme: furan → (nBuLi, Et2O, RT) → 2-lithiofuran → (SO2, −30°) → furan-SO2Li → (Cl2, H2O, HCl) → furan-SO2Cl → (NH4OH, 0–5°) → furan-SO2NH2 → (excess (COCl)2) → furan-SO2NCO

A. Lithium - 2-furansulfinate

To a solution of 39.6 g furan (585 mm) in 200 ml anhydrous ethyl ether was added carefully, under nitrogen atmosphere, 400 ml 1.6 M N-butyl lithium in hexane while maintaining the reaction temperature at 30° or lower. The mixture was stirred until precipitation appeared complete. After cooling to −25 to −30°, excess gaseous sulfur dioxide was slowly passed through the mixture during a 2-hour period. The mixture was stirred at room temperature for an additional 90 minutes and the precipitated lithium-2-furansulfinate was filtered and washed with acetone. m.p. 250°. IR (Nujol) 3400–3000 cm$^{-1}$(W), 1700 cm$^{-1}$, 1550 cm$^{-1}$ (VW), 1210 cm$^{-1}$, 1140 cm$^{-1}$, 1115 cm$^{-1}$ (m), 1020 cm$^{-1}$(VS), 910 cm$^{-1}$, 880 cm$^{-1}$, 825 cm$^{-1}$ (W), 735 cm$^{-1}$(S).

B. 2-Furansulfonyl chloride

Ninety ml of water, 410 ml of conc. HCl, and 68.0 g of lithium 2-furansulfinate were stirred and cooled to 10°–15°. Liquid chlorine (12.3 ml, 39.4 g) was added dropwise over a 30-minute period. The mixture was stirred an additional 30 minutes at 5°, poured onto ice and extracted with methylene chloride. Evaporation of the methylene chloride yielded 44 g 2-furansulfonyl chloride, b.p. 95° at 7 mm Hg;

IR (neat) 3400 (m), 3120, 1800, 1550 (m), 1450 (S), 1380 (VS), 1210, 1160, 1120 (VS), 1035 (m), 1010 (VS), 913, 882 (S).

C. 2-Furansulfonamide

Twenty-three g of 2-furansulfonyl chloride (138 mm) was added dropwise into 200 ml of conc. NH$_4$OH at 0°–5°. After stirring overnight at room temperature, the water was removed under vacuum and the precipitate washed with ice water and dried. Yield: 14 g 2-furansulfonamide m.p. 120–122°. (literature m.p. 120°–122°: JOC 18, 894 (1953)). IR (Nujol) 3250 cm$^{-1}$, 3100 cm$^{-1}$, 1600 cm$^{-1}$ (W), 1550 cm$^{-1}$, 1310 cm$^{-1}$, 1190 cm$^{-1}$, 1140 cm$^{-1}$ 1120 cm$^{-1}$, 1055 cm$^{-1}$, 1005 cm$^{-1}$, 930 cm$^{-1}$, 880 cm$^{-1}$, 843 cm$^{-1}$ (S).

D. 2-Furansulfonyl isocyanate

Dry toluene (150 ml), 25 ml oxalyl chloride (295), and a trace of DABCO (diaza-bicyclo[2.2.2]octane) were heated to 90°. Ten g of 2-furansulfonamide was added over a 15 minute period and the mixture was held at 95° for 2 hours. After filtering, the solvent was removed under vacuum to yield 2.1 g of an oil showing the characteristic isocyanate absorption in the infrared (2280 cm$^{-1}$).

Formulations

Useful formulations of the compounds for Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE IV

|  | Active Ingredient | Diluent(s) | Surfactant(s) |
|---|---|---|---|
| Wettable Powders | 20–90 | 0–74 | 1–10 |
| Oil Suspensions, Emulsions, Solutions (including Emulsifiable Concentrates) | 3–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," 2nd Ed., Dorland Books, Caldwell, New Jersey. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual," MC Publishing Corp., Ridgewood, New Jersey, as well as Sisely and Wood, "Encyclopedia of Surface Active Agents," Chemical Publishing Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration," Chemical Engineering, Dec. 4, 1967, pp. 147ff. and "Perry's Chemical Engineer's Handbook," 4th Ed., McGraw-Hill, New York, 1963, pp. 8–59 ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3, line 66 through Col. 5, line 17 and Examples 1–4.

G. C. Klingman, "Weed Control as a Science," John Wiley & Sons, Inc., New York, 1961, pp. 81–96.

J. D. Fryer and S. A. Evans, "Weed Control Handbook," 5th Ed., Blackwell Scientific Publications, Oxford, 1968, pp. 101–103.

In the following examples, all parts are by weight unless otherwise indicated.

EXAMPLE 9

| Wettable Powder | |
|---|---|
| N-[(4,6-dimethylprimidin-2-yl)amino-carbonyl]benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns and then reblended.

EXAMPLE 10

| Wettable Powder | |
| --- | --- |
| N-[(4-methoxy-6-methylpyrimidin-2-yl)-aminocarbonyl]-2-chloro-5-methoxybenzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles of active essentially all below 10 microns in diameter. The product is reblended before packaging.

EXAMPLE 11

| Granule | |
| --- | --- |
| wettable powder of Example 10 | 5% |
| attapulgite granules (U.S.S. 20–50 mesh; 0.84–0.42 mm) | 95% |

A slurry of wettable powder containing 25% solids is sprayed on the surface of attapulgite granules in a double-cone blender. The granules are dried and packaged.

EXAMPLE 12

| Extruded Pellet | |
| --- | --- |
| N-[4-methoxy-6-methylpyrimidin-2-yl)-aminocarbonyl]-2-chlorobenzenesulfonamide | 25% |
| anhydrous sodium sulfate | 10% |
| crude calcium ligninsulfonate | 5% |
| sodium alkylnaphthalenesulfonae | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 Sieve (0,84 mm openings). The granules held on a U.S.S. No. 40 sieve (0.42 mm openings) may be packaged for use and the fines recycled.

EXAMPLE 13

| Oil Suspension | |
| --- | --- |
| N-[(4,6-dimethoxypyrimidin-2-yl)-aminocarbonyl]-2,5-dichlorobenzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 14

| Wettable Powder | |
| --- | --- |
| N-[(4,6-dimethylpyrimidin-2-yl)-aminocarbonyl]-2,6-dichlorobenzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer mill to produce particles essentially all below 100 microns, the material is reblended and sifted through a U.S.S. No. 50 sieve (0.3 mm opening) and packaged.

EXAMPLE 15

| Low Strength Granule | |
| --- | --- |
| N-[(4-methoxy-6-methylpyrimidin-2-yl)-aminocarbonyl]-2-methylbenzenesulfonamide | 1% |
| N,N-dimethylformamide | 9% |
| attapulgite granules (U.S.S. 20–40 mesh). | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 16

| Aqueous Suspension | |
| --- | --- |
| N-[(4,6-dimethylpyrimidin-2-yl)aminocarbonyl]-benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| Polyvinyl alcohol | 1.0% |
| Water | 56.7% |

The ingredients are blended and ground together in a sand mill to produce particles essentially all under 5 microns in size.

EXAMPLE 17

| Solution | |
| --- | --- |
| N-[(4-methoxy-6-methylpyrimidine-2-yl)-aminocarbonyl]-2-chlorobenzenesulfonamide, sodium salt | 5% |
| water | 95% |

The salt is added directly to the water with stirring to produce the solution, which may then be packaged for use.

EXAMPLE 18

| Low Strength Granule | |
| --- | --- |
| N-[(4,6-dimethylpyrimidin-2-yl)aminocarbonyl]-2,6-dichlorobenzenesulfonamide | 0.1% |
| attapulgite granules | |

-continued

| Low Strength Granule | |
|---|---|
| (U.S.S. 20-40 mesh) | 99.9% |

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 19

| Granule | |
|---|---|
| N-[(4,6-dimethoxypyrimidin-2-yl)-aminocarboyl]-2,5-dichloro-benzenesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 20

| High Strength Concentrate | |
|---|---|
| N-[(4,6-dimethylpyrimidin-2-yl)-aminocarboyl]-2-thiophene-sulfonamide | 99% |
| silica aerogel | 0.5% |
| synthetic amorphous silica | 0.5% |

The ingredients are blended and ground in a hammer mill to produce a material essentially all passing a U.S.S. No. 50 screen (0.3 mm opening). The concentrate may be formulated further if necessary.

EXAMPLE 21

| Wettable Powder: | |
|---|---|
| N-[(4-methoxy-6-methylpyrimidin-2-yl)-aminocarbonyl]-2-chlorobenzene-sulfonamide | 95% |
| dioctyl sodium sulfosuccinate | 0.1% |
| synthetic fine silica | 4.9% |

The ingredients are blended and ground in a hammer-mill to produce particles essentially all below 100 microns. The material is sifted through a U.S.S. No. 50 screen and then packaged.

EXAMPLE 22

| Wettable Powder: | |
|---|---|
| N-[(4,6-dimethoxypyrimidin-2-yl)aminocarbonyl]2,5-dichlorobenzene-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 23

| Oil Suspension | |
|---|---|
| N-[(4-methoxy-6-methylpyrimidin-2-yl)-aminocarbonyl]-2-methylbenzene-sulfonamide | 35% |
| blend of polyalcohol carboxylic% esters and oil petroleum sulfonates | 6% |
| xylene | 59% |

The ingredients are combined and ground together in a sand mill to produce particles essentially all below 5 microns. The product can be used directly, extended with oils, or emulsified in water.

The compounds of Formula I can be formulated using the procedures of Examples 9-23.

UTILITY

The compounds of Formula I are useful as herbicides. They may be applied either pre- or postemergence for the control of undesired vegetation in noncrop areas and for selective weed control in certain crops, e.g., wheat and barley. Some of these compounds are useful for the pre- and/or postemergence control of nutsedge in crops such as cotton, corn and rice. By properly selecting rate and time of application, compounds of this invention may be used to modify plant growth beneficially.

The precise amount of the compound of Formula I to be used in any given situation will vary according to the particular end result desired, the use involved, the weeds to be controlled, the soil type, the formulation and mode of application, weather conditions and like factors. Since so many variables play a role, it is not possible to state a rate of application suitable for all situations. Broadly speaking, the compounds of this invention are used at levels of about 0.005 to 20 kg/ha with a preferred range of 0.01 to 10 kg/ha. The lower rates of the range will generally be selected for lighter soils, for selective weed control in crops or in situations where maximum persistence is not necessary.

The compounds of Formula I may be combined with other herbicides and are particularly useful in combination with 3-(3,4-dichlorophenyl)-1,1-dimethylurea, the triazines such as 2,4-bis(isopropylamino)-6-(methylthio)-s-triazine, the uracils such as 5-bromo-3-sec-butyl-6-methyluracil, N-(phosponomethyl)glycine, 3-cyclohexyl-1-methyl-6-dimethylamino-s-triazine-2,4(1H,3H)-dione, N,N-dimethyl-2,2-diphenylacetamide, 2,4-dichlorophenoxyacetic acid (and closely related compounds), 4-chloro-2-butynyl-3-chlorophenylcarbamate (Carbyne ®), diisopropylthiolcarbamic acid, ester with 2,3-dichloroallyl alcohol (Avadex ®), diisopropylthiolcarbamic acid, S-(2,3,3-trichloroallyl) ester (Avadex ® BW), ethyl-N-benzoyl-N-(3,4-dichlorophenyl)-2-aminopropionate (Suffix ®), 1,2-dimethyl-3,5-diphenyl-pyrazolium methyl-sulfate (Avenge ®), methyl 2-[4-(2,4-dichlorophenoxy)-phenoxy]-propanoate(Hoelon ®), 4-amino-6-tertbutyl-3-(methylthio)-1,2,4-triazin-5(4H)-one (Lexone ®), 3-(3,4-dichlorophenyl)-1methoxy-1-methylurea (Lorox ®), 3-isopropyl-1H-2,1,3-benzothiodiazin-(4)-3H-one 2,2-dioxide, α,α,α-trifluoro-2,6-dinitro-N,N-dipropyl-p-toluidine, 1,1'-dimethyl-4,4'bipyridinium ion, monosodium methanearsonate, 2-chloro-2',6',-diethyl-(methoxymethyl) acetanilide, and 1,1-dimethyl-3-(α,α,α-trifluoro-m-tolyl)urea (Cotoran ®).

The activity of these compounds was discovered in greenhouse tests. The tests are described and the data resulting from them are shown below.

TEST PROCEDURE

Seeds of crabgrass (*Digitaria sp.*), barnyardgrass (*Echinochloa crusgalli*), wild oats (*Avena fatua*), Cassia tora, morningglory (*Ipomoea sp.*), cocklebur (*Xanthium sp.*), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliolate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days, then all species were compared to controls and visually rated for response to treatment.

Ratings for compounds tested by this procedure are recorded in Table V.

0 = no effect
& or 10 = maximum effect
B = burn
C = chlorosis or necrosis
D = defoliation
E = emergence inhibition
G = growth retardation
H = formative effects
I = increased green coloration
L = lodging
P = terminal bud kill
S = albinism
U = unusual pigmentation
6Y = abscised buds or flowers
%Z = fasciation
X = axillary stimulation
6F = delayed flowering

TABLE V-A

| R₃ | R₄ | R₅ | R₆ | R₇ | Mode of Application | Rate Kg/Ha | Bush Bean | Cotton | Sorghum | Corn | Soybean | Wheat | Wild Oats | Rice | Barnyard-grass | Crabgrass | Morning-glory | Cocklebur | Cassia | Nutsedge |
|---|---|---|---|---|---|---|---|---|---|---|---|---|---|---|---|---|---|---|---|---|
| F | H | Cl | H | H | Post | 0.4 | 1C | 3C | 1C | 2C | 1C | 1C | 1C | 0 | 1C | 0 | 3G | 3G | 0 | 0 |
|   |   |   |   |   | Pre  | 0.4 |    |    | 0  | 0  | 0  | 0  | 0  | 0 | 0  | 0 | 0  | 0  | 0  | 0 |
| CH₃ | Cl | H | H | H | Post | 0.4 | 2G | 1H | 5G | 2G | 0 | 2G | 0 | 2G | 0 | 0 | 1C | 7G | 2G | 5G |
|   |   |   |   |   | Post | 0.4 |    | 2C |    |    |   |    |   |    |   |    | 9G | 6F |    |    |
|   |   |   |   |   | Pre  | 0.4 |    | 4G |    |    |   |    |   |    |   |    |    |    |    |    |
| H | Cl | H | Cl | H | Pre  | 0.4 | 2C | 3C | 2H | 4G | 1H | 0 | 0 | 9H | 0 | 0 | 8G | 9G | 7G | 4G |
|   |   |   |   |   | Pre  | 0.4 | 5H | 7G | 8G | 0  |    |    |    |    |    |    |    |    |    |    |
|   |   |   |   |   | Post | 0.4 | 6Y |    | 0  |    |    |    |    |    |    |    |    |    |    |    |
| H | Cl | H | Cl | H | Post | 0.4 |    |    | 0 | 0 | 1C | 0 | 0 | 0 | 0 | 0 | 0 | 2G | 0 | 0 |
|   |   |   |   |   | Post | 0.4 |    |    |   |   | 5G |    |    |    |    |    |    |    |    |    |
| F | H | H | F | H | Pre  | 0.4 | 3S | 5C | 0 | 0 | 1C | 0 | 0 | 1C | 0 | 0 | 1C | 9G | 5G | 1C |
|   |   |   |   |   | Post | 0.4 | 7G | 7G | 2G |   | 1C |    |    | 2G | 2G | 2G | 2H | 3G | 3G | 7G |
|   |   |   |   |   | Post | 0.4 | 6Y |    |    |   | 3H |    |    |    |    |    | 7G |    |    |    |
| F | H | H | F | H | Pre  | 0.4 |    |    | 1H | 6g | 2C | 0 | 0 | 1C | 0 | 0 | 8G | 9G | 8G | 0 |
|   |   |   |   |   | Post | 0.4 |    |    |    |   | 2H |   |   | 6G |    |    |    |    |    |    |
| Cl | H | H | H | Cl | Post | 0.4 | 9C | 6C | 5U | 8H | 5C | 4G | 1C | 5C | 5C | 9G | 5C | &C | 6C | 7C |
|   |   |   |   |   | Pre  | 0.4 |    | 9G | 9G | 1C | 9G |    | 5G | 9G | 9H |    | 9G |    |    | 9G |
|   |   |   |   |   | Pre  | 0.4 |    |    | 9H | 9G | 9H | 7G | 6G | &E | 9H | 4G | 9G | 9G | 9C | &E |

TABLE V-B

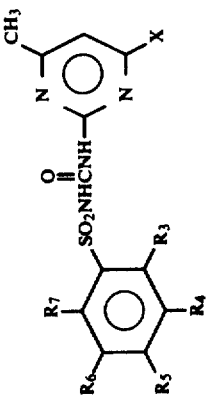

| R3 | R4 | R5 | R6 | R7 | X | Mode of Application | Rate Kg/Ha | Bush Bean | Cotton | Sorghum | Corn | Soybean | Wheat | Wild Oats | Rice | Barnyard-grass | Crab-grass | Morning-glory | Cock-lebur | Cassia | Nut-sedge |
|---|---|---|---|---|---|---|---|---|---|---|---|---|---|---|---|---|---|---|---|---|---|
| Cl | H | H | Cl | H | H | Post | 2.0 | 1C 4H | 1C 4G | 4G | 3G | &C | 0 | 0 | 3G | 1C | 1C 5G | 2G 9C | 2G 8G | 0 5G | 1C 6G |
|  |  |  |  |  |  | Post | 2.0 |  |  | 2G | 2G | 1C | 2G | 2C | 8G | 2C | 3G | 9C | 8G | 9C | 1C 9G |
| Cl | H | H | H | H | H | Pre | 2.0 | 9C | 9C | 4U 9H | 9H 9G | 5C 2C 6H | 6G 8G | 1C 1C 5G | 1C &E | &C 1C | 1C 5G | 9C 9C | 1C 8G | 9C 9G | 1C 9C &E |
|  |  |  |  |  |  | Pre | 0.4 |  |  |  |  |  |  |  |  |  |  |  |  |  |  |
| H | Cl | H | H | H | H | Post | 0.4 | 3S 7G 6Y | 5C 8G | 0 | 4G | 4G | 0 | 5G 0 | 4G | 0 | 3G | 1C 5G | &P 8G | 2C | 1C 4G |
|  |  |  |  |  |  | Pre | 0.4 |  |  |  |  |  |  |  |  |  |  |  |  |  |  |
| CH3 | H | H | H | H | H | Post | 0.4 | 1C | 0 | 5G | 0 | 5H | 0 | 2G | &E | 0 | 0 | 9C | 8H | 7G | 1C 9G |
|  |  |  |  |  |  | Pre | 0.4 |  |  | 0 | 0 | 1C 0 | 0 | 0 | 0 | 0 | 0 | 1C 9G | 0 9G | 0 1C 5G | 0 0 |
| F | Cl | H | H | H | H | Post | 0.4 | 3C 9G 9D | 4C 2H 8G | 2H 9G | 1H 6G | 1C 6G | 4G | 0 | 5G | 2C 9H | 2G | 1C 9G | 9C | 1C 4G | 1C 9G |
|  |  |  |  |  |  | Pre | 0.4 |  |  |  |  |  |  |  |  |  |  |  |  |  |  |
| CH3 | H | H | H | H | CH3OCH2 | Post | 0.4 | 6C 9G | 6C 9G | 2H 8G 2C 9H | 1C 7G 3C 9G 9G | 7H | 5G | 2G | 9H | 1C 6G 5C 9H | 1G | &C 9G | 9G | 9G | &E |
|  |  |  |  |  |  | Pre | 0.4 |  |  |  |  |  |  |  |  |  |  |  |  |  |  |
| Cl | H | H | H | H | CH3OCH2 | Post | 0.4 | 6C 9G | 7C 9G | 6C 9G 9H | 3C 9G | 2C 9G 8H | 8C 9H | 1C 8G 2C 7G | 5C 8G &E | 5C 9H 9H | 2C 7G 2C 9G | &C 9G | 9C &E | 5C 9G 9G | 2C 9G &E |
|  |  |  |  |  |  | Pre | 0.4 |  |  |  |  |  |  |  |  |  |  |  |  |  |  |
| Cl | H | H | Cl | H | CH3OCH2 | Post | 0.4 | 4C 8G 6Y | 5C 8G | 3C 9G | 8H | 2H | 2G | 2C 3C 2C 8H | 3C | 5C 9H 9H | 2C 8G 2C 9G 5G | 5C 9G | 2C 8G | 3C | 8G |
|  |  |  |  |  |  | Pre | 0.4 |  |  |  |  |  |  |  |  |  |  |  |  |  |  |
| CH3O— | H | H | CH3O— | H | CH3OCH2 | Post | 0.4 | 5C 9G | 7C 9G | 2C 8G 4C 9G 9H | 2C 8G 4U 9G 9G | 3C 9G 3H | 9H | 8G 2C 8G 6G | 9H 4C 8G &E | 2C 9H 9H | 8G 2C 8G 9C 5G | 1C 5G 9G | 2C 8G 9G | 9G 2C 8G 9G | 9G 7G &E |
|  |  |  |  |  |  | Pre | 0.4 |  |  |  |  |  |  |  |  |  |  |  |  |  |  |
| H | H | H | H | H | OC2H5 | Post | 2.0 | 2H 7G | 2H 8G | 7G | 1H 8G | 9C | 5G | 0 | 8G | 8H | 8G | 2H 8G | 2H 8G | 1C 5G | 8G |
|  |  |  |  |  |  | Post | 2.0 |  |  |  |  |  |  |  |  |  |  |  |  |  |  |

TABLE V-B-continued

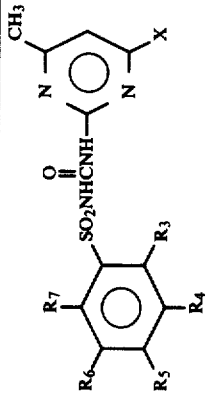

| R3 | R4 | R5 | R6 | R7 | X | Mode of Application | Rate Kg/Ha | Bush Bean | Cotton | Sorghum | Corn | Soybean | Wheat | Wild Oats | Rice | Barnyard-grass | Crab-grass | Morning-glory | Cocklebur | Cassia | Nut-sedge |
|---|---|---|---|---|---|---|---|---|---|---|---|---|---|---|---|---|---|---|---|---|---|
| H | H | H | H | H | H | Post | 2.0 | 6Y | | 9G | 9G | 4H 9G 2H 5G | 7G | 7G | &E | 7G | 2G | &E | — | &E | &E |
| | | | | | | Pre | 2.0 | | | 4G | 1C 5G | | 0 | 0 | 2G | 2G | 2G | 5G | 0 | 5G | 6G |
| | | | | | | Post | 2.0 | 3H 8G 6Y | 4H 7G | | | | | | | | | | | | |
| F | H | H | H | H | H | Post | 2.0 | 2C 8G 6Y | 3C 8G | 3G 2C 9G | 5G 1C 4G | 0 1C 8H | 0 1C 5G | 0 1C | 7G 5G | 5G 1C 9H | 0 1C 7G | 8G 1C 9G | 9G 9C | 8G 2C | 5G 1C 8G |
| | | | | | | Pre | 0.4 | | | | | | | | | | | | | | |
| | | | | | | Post | 0.4 | | | | | | | | | | | | | | |
| | | | | | | Pre | 0.4 | | | | | | | | | | | | | | |
| H | H | H | H | H | H | Post | 2.0 | 1C 9G 6Y | 2H 2C 9G | 1U 8G 2H 8G | 1C 8G 6G | 1C 6H 1C 9G | 9G | 5H | &E 1C 8G | 1C 9G 8H | 1C 7G 2G | 9G 2C 9G | 9G 9C | 8G 1C 4G | &E 6C 7G |
| | | | | | | Pre | 2.0 | | | | | | 0 | | | | | | | | |
| CH3 | H | H | H | H | H | Post | 2.0 | 1C 8G 6Y | 2C 7G 8G | 1C 7G 6G | 1C 8G 5L | 1C 7G 6G | 6G | 7G | &E | 1C 6H 1C 8G | 3G | 9G | 9G | 8G | 9G |
| | | | | | | Pre | 2.0 | | | | | | | | | | | | | | |
| | | | | | | Post | 2.0 | | | 1C 8G 2G | 9G | 4H 8G 1C 5G | 9G | 7G | 8G | | 2C 7G | 8C | 9C | 3C 5G | 7C 9G |
| | | | | | | Pre | 2.0 | 2C 8G 6Y | 2C 5G | | 2G | | 2G | 0 | &E | 2H 9G 1C | 9G | &E | — | 7G | &E |
| H | H | H | Cl | H | OCH(CH3)2 | Post | 2.0 | 1C 8G 6Y | 1C 2H 7G | 3H 2G | 5G 4G | 6G 1C 4G | 5G | 3G | 9H 5G | 2G | 0 | 5G | 2C 5G | 2C | 5G |
| | | | | | | Pre | 2.0 | | | | | | 0 | 0 | 5G | 0 | 0 | | &E 0 | | |
| OCH3 | H | H | H | H | H | Post | 2.0 | 2H 7G 6Y | | | | 4G | 2G | 2G | 9G | 0 | 5G | 9G | 1C 6G | 5G 2C | &E 1C 6G |
| | | | | | | Pre | 2.0 | | | 2G | 4G | | | | | | | | | 1C 5G | 1C 9G |

TABLE V-C

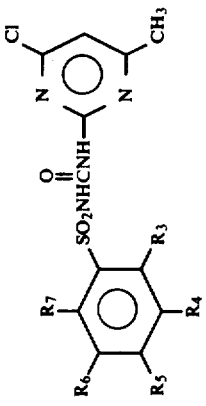

| R₃ | R₄ | R₅ | R₆ | R₇ | Mode of Application | Rate Kg/Ha | Bush Bean | Cotton | Sorghum | Corn | Soybean | Wheat | Wild Oats | Rice | Barnyard-grass | Crabgrass | Morning-glory | Cocklebur | Cassia | Nutsedge |
|---|---|---|---|---|---|---|---|---|---|---|---|---|---|---|---|---|---|---|---|---|
| H | H | H | H | H | Post | 2.0 | 1S | 1C | 6G | 1C | 2C | 0 | 1C | 1C | 1C | 3G | 1C | 5G | 1C | 5G |
|   |   |   |   |   | Post | 2.0 | 5G |   |   |   |   |   |   | 6G | 7H |   | 5G |   | 5G |   |
|   |   |   |   |   | Post | 2.0 | 6Y |   |   |   |   |   |   |   |   |   |   |   |   |   |
|   |   |   |   |   | Pre | 2.0 |   |   | 7G | 1C | 1C | 3G | 5G | &E | 2C | 5G | 5G | 5G | 6G | &E |
|   |   |   |   |   | Pre | 2.0 |   |   |   | 5G |   |   |   |   | 6G |   |   |   |   |   |
| Cl | H | H | H | H | Post | 2.0 | 3C | 2C | &C | 9C | 3C | 9C | 1C | &C | 2C | 3C | 2C | 4H | 9C | 8C |
|   |   |   |   |   | Post | 2.0 | 3H | 3H |   |   | 9G |   | 8G |   | &C | 8G | 9G | 9G |   | 9G |
|   |   |   |   |   | Post | 2.0 | 9G | 9G |   |   |   |   |   |   |   |   |   |   |   |   |
|   |   |   |   |   | Pre | 2.0 |   |   | 9G | 1U | &E | 9G | 3C | &E | 2C | 1C | &E | 9C | 2C | &E |
|   |   |   |   |   | Pre | 2.0 |   |   |   | &G | 5G | &G | 8G | &G | 9G | 5G |   |   | 9G |   |
| NO₂ | H | H | H | H | Post | 2.0 | &G | 8G | &C | 8H | 7G |   | 9G | &G | 9G | 5G | &C | &G | 7C | &C |
|   |   |   |   |   | Post | 2.0 | 5H | 2C |   |   | 5H | 4C | 3C | 7C | &C | 9C |   | 5C |   |   |
|   |   |   |   |   | Post | 2.0 | 6D |   |   |   |   |   |   |   |   |   |   |   |   |   |
|   |   |   |   |   | Pre | 2.0 |   |   | &C | &E | 7G | 7G | 7G | &E | 9G | 9G | 8G | 7G | 9G | &E |
|   |   |   |   |   | Pre | 2.0 |   |   |   |   | 7H |   |   |   | 5H |   |   | 5H | 7C |   |

TABLE V - D

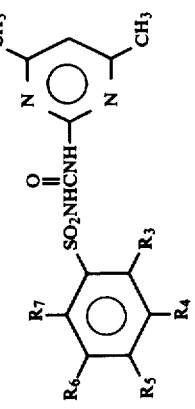

| R₃ | R₄ | R₅ | R₆ | R₇ | Mode of Application | Rate Kg/Ha | Bush Bean | Cotton | Sorghum | Corn | Soybean | Wheat | Wild Oats | Rice | Barnyard-grass | Crabgrass | Morning-glory | Cocklebur | Cassia | Nutsedge |
|---|---|---|---|---|---|---|---|---|---|---|---|---|---|---|---|---|---|---|---|---|
| Cl | H | H | H | CH₃ | Post | 0.4 | 4C 9G | 5C 9G | 5U 9G &E | 5U 9G &E | 9C 9H | 3C 7G 9H | 8G 2C 8G | 5C 7G &E | 9C 9H | 5C 8G 9H | &C 9G | 9C 9G | 6C 9G 9G | 9G &E |
| H | H | H | H | | Post | 0.4 | 2C 7G 6Y | 3H 2H 8G | 1C 9G | 2H 3H 7G 1C 9G 5H | 7G 5G | 8G | 2C 8G 9P | 7G 9G | 4G | 3G | 1C | 2C 7G | | 3G | |
| OCH₃ | Cl | H | H | H | Post | 0.4 | 2H 9G 6Y | 2H 2C 9G | 2H 9G 8H | 1C 9G 5H | 1C 6G 5H | 8G | 8G | &E | 2C 8G | 2G | 5G | 1C 9G 3C 9G | 5G 2H 8G | 2H 8G | 5G 2C 9G |
| Cl | H | H | CH₃ | H | Pre Post | 0.4 0.4 | 3C 9G 6Y | 3C 3H 9G | 5G 3U 9G 9H | 6G 9G 2C | 0 3C 9G | 2G 5G | 0 7G | 9H 8G | 1H 1C 9H | 4G 3G | 8G &C | 9G 2C 9G | 9G 6C 9G | 5G 1C 9G |
| H | H | H | NO₂ | H | Pre Post | 0.4 0.4 | | | 9H | 2C 9G 1C 9G | 6H | 1C 7G | 0 7G | 9H | 9H | 3G | 9G | &E | 9G | &E |
| H | H | H | H | H | Pre Post | 0.4 2.0 | 3C 7G | 2C 3H 8G | 1C 8G | 2C 9G 1C 9G | 1C 7G | 1C 7G | 2C 8G | 8C | 3C 7H | 3C 8G | 8G | 8G | 6C | 8G |
| CH₃ | H | H | H | H | Pre Post | 2.0 2.0 | 8G 6Y 8D | 2C 3H 8G | 1U 3C 8G &E | 3U 8G 5C &E | 3H 9G | 9H 8G 7C | 7C 9H 1G | &E 5C 8G | 9H | 1C 7G | 8G | &E | &E | &E |
| H | H | H | CF₃ | H | Pre Post | 2.0 2.0 | 1B 7G 6Y | 3B 3H 9G | 5G | 4G | 4G | 1G | 1C | &E 1C 8G | 1C | 9G | 9G | — | &E | 8G |
| H | H | H | H | H | Pre Post | 2.0 2.0 | 8G 9C | 9G 9C | 2C 5G 9C | 1C 7G &C | 4C 9G | 7G 9C | 7G 9C | &E 5C &E | 2G 9C | 0 &C | 8G 9G | 8C 9G | 8G &C | &E 2H 8G |
| NO₂ | H | H | H | H | Post | 0.4 | 9G 9C | 9G 9C | 2C 9G &E | &E | 9G | 9C | 9C | 5C &E | 9C | &C | &C | &C | 9G | 9C &E |
| CH₃ | CH₃ | H | CH₃ | CH₃ | Post Pre | 0.4 0.4 | 0 | 0 | 0 1C | 3G 1C | 0 1C | 0 1C | 0 1C | 4G 2G | 0 3C | 0 2G | 0 1C | 0 0 | 9C 5C 0 1C | 0 5G |

TABLE V - D-continued

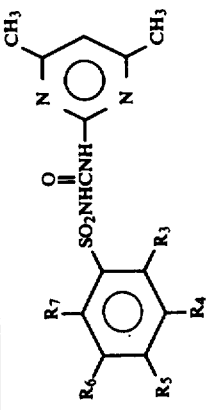

| R3 | R4 | R5 | R6 | R7 | Mode of Application | Rate Kg/Ha | Bush Bean | Cotton | Sorghum | Corn | Soybean | Wheat | Wild Oats | Rice | Barnyard-grass | Crabgrass | Morning-glory | Cocklebur | Cassia | Nutsedge |
|---|---|---|---|---|---|---|---|---|---|---|---|---|---|---|---|---|---|---|---|---|
| CH3 | H | H | NO2 | H | Pre | 0.4 | 3S | 2H | 7G | 3G | 2H | /G | 8G | 6G | 2C | 5G | 6H | 1H | 2C | 2C |
|  |  |  |  |  | Post | 0.4 | 7G | 3C | 2U | 9H | 8G |  |  |  | 7G |  | 2C | 6F |  | 8G |
|  |  |  |  |  |  |  | 6Y | 8G | 8G |  |  |  |  |  |  |  | 5G |  |  |  |
| F | H | F | H | F | Pre | 0.4 | 1C | 2H | 7G | 7G | 1G | 8G | 8G | 7H | 5G | 5G | 6G | 3H | 0 | &E |
|  |  |  |  |  | Post | 0.4 |  | 3C | 0 | 0 | 2G | 0 | 0 | 0 | 0 | 1C | 2C | 2C | 2C | 8G |
|  |  |  |  |  |  |  |  |  |  |  |  |  |  |  |  |  | 8G | 9G |  |  |
|  |  |  |  |  |  |  |  |  |  |  |  |  |  |  |  |  | 5G | 5G |  |  |
| Cl | H | Cl | H | Cl | Pre | 0.4 | 2C | 2C | 2G | 5G | 5G | 2G | 0 | 5G | 5G | 4G | 6G | 8G | 2G | 8G |
|  |  |  |  |  | Post | 0.4 | 2H | 4H | 0 | 0 | 0 |  |  |  | 0 | 0 | 2C | 2C | 0 | 0 |
|  |  |  |  |  |  |  |  |  |  |  |  |  |  |  |  |  | 8G | 8G |  |  |
|  |  |  |  |  |  |  |  |  |  |  |  |  |  |  |  |  | 7G | 5G |  |  |
| Cl | H | H | Cl | H | Pre | 0.4 | 2H | 2C | 1U | 4G | 0 | 7G | 2C | 0 | 0 | 5G | 8G | 8G | 0 | 5G |
|  |  |  |  |  | Post | 0.4 | 7G | 5H | 9G | 9H | 4H |  | 5G | 2C |  | 1C | &C | 9C | 5C | 1C |
|  |  |  |  |  |  |  | 6Y | 9G |  |  | 9G |  |  | 8G |  |  |  |  | 9G | 9G |
| OCH3 | H | H | Cl | H | Pre | 2.0 | 2H | 1C | 2C | 1C | 2C | 7G | 1C | &E | 2C | 2C | 9G | 8G | 8G | &E |
|  |  |  |  |  | Post | 2.0 | 8G | 2H | 9G | 9G | 2H | 1C | 6G | 1C | 6G | 6G | 2C |  |  |  |
|  |  |  |  |  |  |  | 6Y | 9G | 2H | 2H | 6G | 8G | 2C | &P | 8G | 1C | 9G |  |  |  |
|  |  |  |  |  |  |  |  |  | 9G |  | 5G |  | 9G | 8G |  | 6G |  |  |  |  |
| OCH3 | H | OCH3 | H | H | Pre | 2.0 | 3C | 5G | 2C | 2C | 0 | 1C | 1C | &E | 7C | 2C | 5G | 8G | 1C | &E |
|  |  |  |  |  | Post | 2.0 | 6Y | 9G | 8G | 5H | 0 | 9G | 9G | 7C | 2G | 5G | 3C | 0 | 8G |  |
|  |  |  |  |  |  |  |  |  |  |  |  |  |  |  |  |  |  |  | 0 |  |
| Cl | H | H | H | H | Pre | 0.4 | 9C | 0 | 2C | 2C | 1C | 7G | 6G | 9H | 2C | 6G | 8G | &E | — | 0 |
|  |  |  |  |  | Post | 0.4 |  |  | 8G | 9H | 9H | 2U | 1C | 9C | 7H |  | 9C | 0 |  |  |
|  |  |  |  |  |  |  |  |  | 9H | 9U | 9H | 1C | 2C | &E | 2C |  | 9G |  |  |  |
|  |  |  |  |  |  |  |  |  |  | &E |  | 9G | 9G | 8G | &C |  |  |  |  |  |
|  |  |  |  |  |  |  |  |  |  |  |  |  |  |  | 3C |  |  |  |  |  |
|  |  |  |  |  |  |  |  |  |  |  |  |  |  |  | 9G |  |  |  |  |  |
| H | H | H | H | H | Pre | 0.4 | 4S | 5C | 6G | 1H | 1C | 7G | 6G | 8G | 2G | 3G | 5G | 3C | 9C | 1C |
|  |  |  |  |  | Post | 0.4 | 6G | 9G |  | 6G | 4G | 3G | 2G | 4G |  | 1C | 8G | 9G | 8G | 5G |
|  |  |  |  |  |  |  | 6Y |  |  |  |  |  |  |  |  |  |  |  |  | 9G |
| CH3 | H | H | H | H | Pre | 0.4 | 1C | 2C | 2H | 1H | 1C | 3G | 2G | 9H | 0 | 1C | 2C | 2C | 3C | 9C |
|  |  |  |  |  | Post | 0.4 | 3G | 2H | 7G | 9G | 4G |  |  |  |  | 6G | 6G | 6F | 7G | &E |
|  |  |  |  |  |  |  |  | 7G | 2G |  |  |  |  |  |  |  | 8G | 9G |  |  |
| F | Cl | H | H | H | Pre | 0.4 | 5S | 5C | 1C | 1C | 1C | 4C | 1C | 9C | 3C | 1C | 1C | &C | 9G | 1C |
|  |  |  |  |  | Post | 0.4 |  |  | 3G | 5G | 4G |  |  |  |  |  | 9G |  |  | 5G |
|  |  |  |  |  |  |  |  |  | 9U | 9U | 9C |  |  |  |  |  |  |  |  | 2C |

TABLE V - D-continued

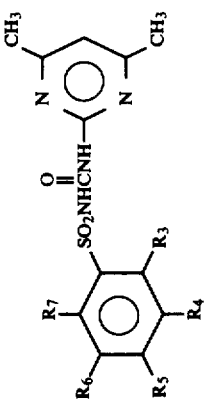

| R₃ | R₄ | R₅ | R₆ | R₇ | Mode of Application | Rate Kg/Ha | Bush Bean | Cotton | Sorghum | Corn | Soybean | Wheat | Wild Oats | Rice | Barnyard-grass | Crabgrass | Morning-glory | Cocklebur | Cassia | Nutsedge |
|---|---|---|---|---|---|---|---|---|---|---|---|---|---|---|---|---|---|---|---|---|
| | | | | | Post | 0.4 | 8G | 9G | 9G | 9G | | 9G | 3G | &E | 9H | 6G | 7G | | 8C | 9G |
| | | | | | Post | 0.4 | 6Y | | | | 8H | | | | | | | | | |
| H | H | H | H | H | Pre | 0.4 | | 2U | 1C | | 2C | 1C | 2C | 5C | 2C | 6G | 5G | 9G | 9G | &E |
| | | | | | Post | 0.4 | 4S | 5C | 9G | 9H | 4H | 9G | 7G | 9G | 9H | 5G | 9G | 1C | 5C | 7G |
| | | | | | Pre | 0.4 | 8G | 9G | 9G | | 5X | 8G | 9G | | 7G | | | 9G | | |
| | (sodium salt) | | | | Post | 0.4 | 2H | | | | | | | | | | | | | |
| CH₃ | H | H | H | H | Pre | 0.4 | 5C | 6C | 2C | 1C | 5G | 9G | 8G | 9C | 9C | 7G | &C | 8G | 8G | 8G |
| | | | | | Post | 0.4 | 9D | 9G | 1C | 4C | 4C | 9G | 9G | &E | 9H | 1C | 9G | 2C | 2C | 9C |
| | | | | | Pre | 0.4 | | | 9G | 9G | 8G | | 2C | | | 6G | 9G | | 9G | &E |
| | (sodium salt) | | | | Post | 0.4 | | | 9H | &E | 9H | 9G | 9G | &E | | 5G | | 9G | 5C | |
| F | H | Cl | H | H | Pre | 0.4 | 2G | 2C | 7G | 6G | 1C | 0 | 0 | 1C | 7G | 3G | 7G | 1C | 1C | 2G |
| | | | | | Post | 0.4 | | 5G | | | 5G | | | 6G | | | 8G | 9G | 4G | |
| CH₃ | Cl | H | H | H | Pre | 0.4 | | | 0 | 1C | | 0 | 0 | 8G | 8G | 0 | 0 | 8G | 8G | 3G | 0 |
| | | | | | Post | 0.4 | 5S | 6C | 1C | 2H | 1C | 2G | | | | | 1C | | 4C | 3C | 5X |
| | | | | | Pre | 0.4 | 9G | 9G | 9G | 8G | 3H | | 7G | | | 2G | | 5G | 9G | | 9G |
| | | | | | Post | 0.4 | 6Y | | | | | | | | | | | | | | |
| H | H | H | H | H | Pre | 0.4 | 2C | 2C | 8G | 2C | 1C | 7G | 0 | 1C | 9H | 1C | 0 | 3G | 1C | 3C |
| | | | | | Post | 0.4 | 7H | 3H | | 9G | 3H | | | 6G | | | | | 5C | | |
| | | | | | Pre | 0.4 | 6F | 7G | | 0 | 2H | 0 | 0 | 8G | 4G | 0 | 0 | 1C | 8G | | 4G |
| F | H | F | H | H | Post | 0.4 | | | 5G | 6G | 1C | 5G | 3G | 1C | 9H | 0 | 0 | 1C | 5C | 4G | 5G |
| | | | | | Pre | 0.4 | 3H | 5C | 6G | 3G | 2H | 3G | 0 | 8G | 7G | 0 | 0 | 5G | 8G | 0 | |
| | | | | | Post | 0.4 | 6G | 8G | | | 6G | | | | | | | | | | |
| Cl | H | H | Cl | Cl | Pre | 0.4 | 6Y | | 8G | 3G | 4G | | 0 | 0 | 9H | 2G | 0 | 5G | 5C | 4G | 0 |
| | | | | | Post | 0.4 | 3H | | 2H | 1C | 2H | 7G | 0 | 0 | 9H | &C | 9C | 9C | &C | 3C | 9C |
| F | H | H | H | F | Pre | 0.4 | 9C | 9C | 8G | 8G | 6G | 6C | 9C | 9C | 9C | 9H | 1C | 9C | 9C | 9C | &E |
| | | | | | Post | 0.4 | 3C | 6C | 5U | 9C | 3C | &E | 1C | 8G | &E | 6C | 9G | 3C | 2C | 2C | 6C |
| | | | | | Pre | 0.4 | 9G | 9G | 9H | 9G | 9H | 9G | 9G | 9H | 9H | 9H | 9G | 9G | 9G | 7G | 9G |
| | | | | | Post | 0.4 | 6Y | | | | | | | | | | | | | 1C | &E |

TABLE V - D-continued

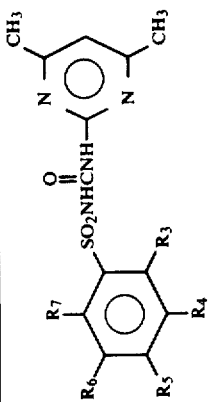

| R$_3$ | R$_4$ | R$_5$ | R$_6$ | R$_7$ | Mode of Application | Rate Kg/Ha | Bush Bean | Cotton | Sorghum | Corn | Soybean | Wheat | Wild Oats | Rice | Barnyard-grass | Crabgrass | Morning-glory | Cocklebur | Cassia | Nutsedge |
|---|---|---|---|---|---|---|---|---|---|---|---|---|---|---|---|---|---|---|---|---|
| OCH$_3$ | H | H | F | H | Pre | 0.4 | 2S 9G 6Y | 2H 3C 9G | 5U 9G | 2U 9H | 3C 9G | 8G | 8G | 3C 8G | 4C 9H | 2C 7G | 2C 9C | 1H | 9G 5C 8G | 9G |
|  |  |  |  |  | Post | 0.4 |  |  |  |  |  |  |  |  |  |  |  |  |  |  |
|  |  |  |  |  | Post | 0.4 |  |  | 9H | 9H | 4H | 9H | 8G | &E | 9H | 2C 6C 2C | 9C | 8G | &E | 3C 7G 2C | &E |
| OCH$_3$— | H | H | CH$_3$ | H | Pre | 0.4 | 3C 5G 6F | 5C 3G | 6G | 3G | 5C 4G | 0 | 2G | 5G | 2C | 2C | 3C | 3C |
|  |  |  |  |  | Post | 0.4 |  |  |  |  |  |  |  |  |  |  |  |  |  |  |
| Cl | Cl | H | H | H | Pre | 0.4 | 4C 9G 6Y | 9C | 5C 7G 3U 9G | 2C 5G 9C | 1C 5C 9G | 3G 3C 8G | 3C | 8G | 2C 4G 3C 9H | 1G 5G | 3G &C | 2C &C | 2G 2C 8G | 3G &C |
|  |  |  |  |  | Post | 0.4 |  |  |  |  |  |  |  |  |  |  |  |  |  |  |
| H | Cl | Cl | H | H | Pre | 0.4 | 2H 6G 6F | 2C 7H | &E | 8H | 2H 2A | 9H | 1C 8G | &E | 2C 9H 2G | 5G | 9G | 9G | 2C 9G 1H | &E |
|  |  |  |  |  | Post | 0.4 |  |  |  |  |  |  |  |  |  |  |  |  |  |  |
| H | F | H | H | CH$_3$ | Post | 2.0 | 2C 4H 9G | 2C 5H 9G | 7H 2H 9G | 7H 1C 6G | 1C 5G 3H 9G | 0 | 0 | &P 9G | 4G | 2G | 4G | 5C 9G | 7G | 5G | 4G |
|  |  |  |  |  | Pre | 2.0 |  |  |  |  |  |  |  |  |  |  |  |  |  |  |
|  |  |  |  |  | Post | 2.0 |  |  |  |  |  |  |  |  |  |  |  |  |  |  |
| H | H | H | F | H | Pre | 0.4 | 2H 5G 9G | 2C 2H 9G | 2H 9G | 8G 1C 6G | 6H 3H 8G | 0 4G | 0 2C 8G | 8H 9G | 1C 6G 9H | 2G 1H | 8G 1C 8G | 8G 2C 9G | 2C 8G | 5G 7G | 7G |
|  |  |  |  |  | Post | 0.4 |  |  |  |  |  |  |  |  |  |  |  |  |  |  |
| CH$_3$ | H | H | OCH$_3$ | H | Pre | 0.4 | 3H 9D 9G | 3C 3H 9G | 2H 7G 5U 9G | 2C 9G 9H | 3H 8G 2H 9G | 7G 2C | 8G | 2C 8G | 7G 6C 9H | 2G 1C 3G | 8G 1C 9G | 9G 2H 8G | 9C 1C 7G | 9C 1C 8G | 8G 1C 8G |
|  |  |  |  |  | Post | 0.4 |  |  |  |  |  |  |  |  |  |  |  |  |  |  |
| Cl | Cl | H | H | H | Pre | 0.4 | 2C | 3C 7G | 2H 9G | 9H 4G | 2H 9H 1C | 7G 0 | 8G 0 | &E 2C 8G | 6C 9H | 1C 6G 0 | 9G 7G | 9G 5C 9G | 9G 9C | 9G 9C | &E 3C 8G |
|  |  |  |  |  | Post | 0.4 |  |  |  |  |  |  |  |  |  |  |  |  |  |  |
|  |  |  |  |  | Pre | 2.0 |  |  |  |  |  |  |  |  |  |  |  |  |  |  |
| Cl | Cl | Cl | H | H | Post | 2.0 |  |  | 0 | 0 | 0 | 0 | 0 | 0 | 0 | 0 | 0 | 2C 9G 9G | 0 1H | 2G 0 |
|  |  |  |  |  | Pre | 2.0 |  |  |  |  |  |  |  |  |  |  |  |  |  |  |

TABLE V - D-continued

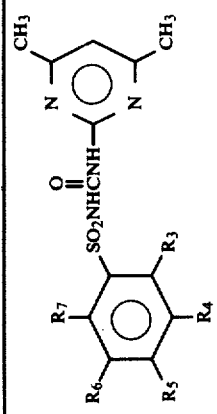

| R3 | R4 | R5 | R6 | R7 | Mode of Application | Rate Kg/Ha | Bush Bean | Cotton | Sorghum | Corn | Soybean | Wheat | Wild Oats | Rice | Barnyard-grass | Crabgrass | Morning-glory | Cocklebur | Cassia | Nutsedge |
|---|---|---|---|---|---|---|---|---|---|---|---|---|---|---|---|---|---|---|---|---|
| Cl | H | Cl | Cl | H | Post | 2.0 | 3H | 1H | 0 | 4H | 3G | 0 | 0 | 0 | 0 | 0 | 4G | 1C | 0 | 0 |
|  |  |  |  |  | Post | 2.0 |  |  |  | 1C | 2G |  |  | 7G | 2G | 0 | 8G | 8G | &E | 0 |
|  |  |  |  |  | Pre | 2.0 |  |  |  | 6G |  |  |  |  |  |  |  |  |  |  |
| Cl | CH3 | H | H | H | Post | 0.4 | 5C | 3C | 9U | 9C | 6C | 8G | 7G | 5C | &C | 2H | 9C | 9C | 9C | 3C |
|  |  |  |  |  | Post | 0.4 | 9G | 4D |  |  | 9G |  |  | 9G |  | 4G |  |  |  | 9G |
|  |  |  |  |  | Pre | 0.4 | 6Y | 8G |  |  |  |  |  |  |  |  |  |  |  |  |
| CH3 | H | H | H | H | Post | 0.4 | 3C | 6C | 9H | 9H | 9H | 9H | 9H | &E | 9H | 5G | &E | &E | 9G | &E |
|  |  |  |  |  | Post | 0.4 | 9G | 9G | 5U | 5C | 5C | 4C | 5C | 5C | 5C |  | 2C | 5C | 7C | 2C |
|  |  |  |  |  | Pre | 0.4 | 6F |  | 9G | 9G | 9G | 9G | 9H | 8G | 9C | 8G | 7G | 9G |  | 7G |
|  |  |  |  |  | Post | 0.4 |  |  | 9G | &E | 6H | 9H | 2C | &E | 9C | 8G | 9G | 9G | 9G | &E |
|  |  |  |  |  | Pre | 0.4 | 4S | 3C | 8H | 1C | 2H |  | 9H |  | 4G | 0 | 6G | 9C |  |  |
| (2-chloroethyltrimethyl-ammonium salt) |  |  |  |  | Post | 0.4 | 8G | 5H |  | 6H | 8G | 0 |  | 8G |  |  |  |  | — | 9G |
|  |  |  |  |  | Pre | 0.4 | 6Y | 9G |  |  |  |  |  |  |  |  |  |  |  |  |
| H | Br | H | H | Br | Post | 0.4 | 9C | 9C | 7H | 9H | 2H | 6G | 0 | 9H | 6G | 0 | 6G | &E | 5G | 8G |
|  |  |  |  |  | Post | 0.4 |  |  | &C | 9U | 9C | 4C | 3C | 3C | 9C | 5C | &C | 5C | 6C | 7C |
|  |  |  |  |  | Pre | 0.4 |  |  | &E | &E | 9H | 9H | 2C | &E | 9H | 9G | 9G | 8G | 9G | &E |
| CF3 | H | H | H | H | Post | 0.4 |  | 9C |  | 9H |  | 9H | 9H |  | 9H | 5H |  |  |  |  |
|  |  |  |  |  | Post | 0.4 | 4C | 6C | 5U | 5C | 5H | 1C | 2C | 5C | 9H | 5G | &P | 3H | 5C | 4C |
|  |  |  |  |  | Pre | 0.4 | 9G | 9G | 9G | 9H | 9H | 7G | 6G | 1C | 5C | 1C | 9G | 9G | 9G | 8G |
| OCH3 | H | H | OCH3 | H | Pre | 0.4 | 6Y |  |  | &H |  | 5G | 9G | &E | 8H | 2H |  |  |  |  |
|  |  |  |  |  | Post | 2.0 | 3S | 8C | 2U | &H | 9H | 9H | 9G | &E | 9H | 5G | 9G | 9G | 9G | 9G |
|  |  |  |  |  | Pre | 2.0 | 4H | 9G | 9H | 9H | 4C |  | 7G | 1C | 5C | 1C | 5C | &C | 3C | 9G |
| Cl | Cl | H | Cl | Cl | Post | 2.0 | 7G | 9G | 9H | 9H | 9H | 5G | 6G | 6G | 8H | 2H | 9C | 9G |  |  |
|  |  |  |  |  | Post | 2.0 |  |  |  |  |  |  |  |  |  |  |  |  |  |  |
|  |  |  |  |  | Pre | 2.0 | 2S | 1C | 0 | 9G | 8H | 9G | 9H | 9H | 9H | 4C | 9G | 9G | 7G | &E |
| CH(CH3)2 | H | Cl | CH(CH3)2 | H | Post | 2.0 | 5G |  |  | 0 | 4H |  | 0 | 0 | 1C | 8G | 0 | 0 | 0 | 0 |
|  |  |  |  |  | Post | 2.0 |  |  | 5G | 1C | 5H | 7G | 7G | 7G | 8G | 2G | 5G | 2G | 5G | 3G |
|  |  |  |  |  | Pre | 2.0 | 2B | 1B | 2H | 9H | 2H | 4G | 6G | 7G | 3C | 5G | 5G | 1C | 9C | 1C |
| CH3 | H | H | CH3 | H | Post | 2.0 | 6G | 4H | 8G |  | 7G |  |  |  | 9H |  |  | 4H |  | 4G |
|  |  |  |  |  | Post | 2.0 | 6Y | 8G |  |  |  |  |  |  |  |  |  | 6F |  |  |
|  |  |  |  |  | Pre | 2.0 |  |  | 9H | 9H | 9H | 8G | 7G | &E | 2C | 5G | 7G | 8G | 7G | &E |
| CH3 | H | H | CH(CH3)2 | H | Post | 0.4 | 4S | 2C | 0 | 0 | 1C | 0 | 0 | 2G | 8G | 0 | 2C | 1C | 1C |  |
|  |  |  |  |  | Post | 0.4 | 8G | 2H |  |  | 5G |  |  |  | 0 |  | 6G | 6G |  |  |

TABLE V - D-continued

[Structure: pyrimidine with two CH₃ groups connected via SO₂NHCNH(=O) to a benzene ring with substituents R₃, R₄, R₅, R₆, R₇]

| R₃ | R₄ | R₅ | R₆ | R₇ | Mode of Application | Rate Kg/Ha | Bush Bean | Cotton | Sorghum | Corn | Soybean | Wheat | Wild Oats | Rice | Barnyard-grass | Crabgrass | Morning-glory | Cocklebur | Cassia | Nutsedge |
|---|---|---|---|---|---|---|---|---|---|---|---|---|---|---|---|---|---|---|---|---|
| F | H | H | H | H | Post | 0.4 | 6Y | | 0 | 1C 7G | 0 | 0 | 0 | 0 | 0 | 3G | 2G | 7G | 0 | 0 |
| | | | | | Pre | 0.4 | | | | | | | | | | | | | | |
| | | | | | Pre | 0.4 | | | | | | | | | | | | | | |
| | | | | | Post | 0.4 | 2C 7G 6Y | 1C 2H 9G | 6U 9G | 5U 9G | 9C | 8G | 2C 7G | 9C | 3C 9H | 2C 8G | 9C | 8C | 9C | 7G |
| | | | | | Pre | 0.4 | | | | | | | | | | | | | | |
| | | | | | Pre | 0.4 | | | | | | | | | | | | | | |
| OC₂H₅ | H | H | OC₂H₅ | H | Post | 0.4 | 5D 9G 6Y | 9C | 1C 9G 2U 8G | 9G | 9H | 1C 9G 1C 6G | 1C 7G 6G | &E 3C 7G | 1C 9H 3C 9G | 1C 9G 6G | 9G | 5C 9G | 9H | 8G | &E 9G |
| | | | | | Pre | 0.4 | | | | | | | | | | | | | | |
| | | | | | Post | 0.4 | | | | | | | | | | | | | | |
| | | | | | Pre | 0.4 | | | | | | | | | | | | | | |
| CH₃ | H | H | Br | H | Post | 0.4 | | | 9H | 1C 8G 9H | 4H | 1C 7G 0 | 7G 0 | 9H 6G | 2C 8H 1C 5H | 4G 0 | 9G 2C 5G | 9G 2C 8G | 3C 9G 2C 5G | 9G 0 |
| | | | | | Pre | 0.4 | | | | | | | | | | | | | | |
| | | | | | Post | 0.4 | 2S 9G 6Y | 5C 9G | 2H 9G | | 5H 7G | | | 6G | | | | | | |
| | | | | | Pre | 0.4 | | | | | | | | | | | | | | |
| CH₃ | H | CH₃ | H | CH₃ | Post | 0.4 | 1H | 0 | 2H 5G 3G 1C 5G | 8H 2G 6G | 1H 5G 2H 0 | 1G 0 | 2G 0 | 5G 0 1C 7H 2G | 2C 7G 0 | 2C 0 | 3G 0 | 9G 0 7G | 6G 0 | 1C 7G 0 |
| | | | | | Pre | 0.4 | | | | | | | | | | | | | | |
| | | | | | Post | 0.4 | | | | | | | | | | | | | | |
| Cl | H | Cl | H | H | Post | 0.4 | 2C 3H | 3C 3H 6G | 0 | 1C | 2H 7G | 0 | 0 | 0 | 0 | 0 | 2G | 5C 9G | 3H 7G | 4C | 4G |
| | | | | | Pre | 0.4 | | | | | | | | | | | | | | |
| | | | | | Post | 0.4 | | | | 6G | 0 | 0 | 0 | 0 | 0 | 2H | 2G | 5G | 8G | 3G | 4G |
| | | | | | Pre | 0.4 | | | | | | | | | | | | | | |

TABLE V - E
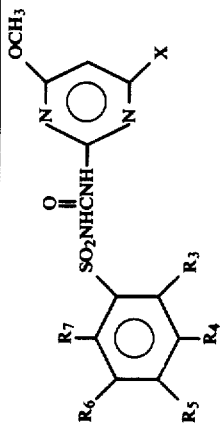
| R3 | R4 | R5 | R6 | R7 | X | Mode of Application | Rate Kg/Ha | BUSH BEAN | COTTON | SORGHUM | CORN | SOYBEAN | WHEAT | WILD OATS | RICE | BARN-YARD-GRASS | CRAB GRASS | MORN-ING GLORY | COCKLE-BUR | CASSIA | NUTS-EDGE |
|----|----|----|----|----|---|---|---|---|---|---|---|---|---|---|---|---|---|---|---|---|---|
| H | H | H | H | H | OC2H5 | Post | 2.0 | 9D | 3C | 8G | 7G | 2H | 3G | 2G | 1C | 3G | 3G | &C | 3C | 8G | 2C |
|  |  |  |  |  |  | Post | 2.0 | 9G | 9G |  |  | 9G |  |  | 9G |  |  |  | 9G |  | 7G |
|  |  |  |  |  |  | Post | 2.0 | 6F |  | 2H | 1C | 9H | 5G | 5G | &E | 7G | 8G | 9G | 8G | 9G | &E |
|  |  |  |  |  |  | Pre | 2.0 |  |  | 8G | 9G |  |  |  |  |  |  |  |  |  |  |
|  |  |  |  |  |  | Pre | 2.0 |  |  | 4G | 1C |  |  |  |  |  |  |  |  |  |  |
| H | H | H | H | H | H | Post | 2.0 | 3C | 5G |  |  | 2C | 0 | 0 | 2G | 1C | 1C | 1C | 2C | 5C | 1C |
|  |  |  |  |  |  | Post | 2.0 | 6F |  |  | 4G | 5G | 0 | 2G | 9H | 4G | 0 | 6G | 6G |  | 5G |
|  |  |  |  |  |  | Pre | 2.0 |  |  | 0 |  |  |  |  |  |  |  | 8G |  | 5G | &E |

TABLE V - F

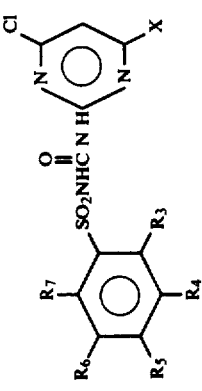

| R₃ | R₄ | R₅ | R₆ | R₇ | X | Mode of Application | Rate Kg/Ha | BUSH BEAN | COTTON | SORGHUM | CORN | SOYBEAN | WHEAT | WILD OATS | RICE | BARN-YARD-GRASS | CRAB-GRASS | MORN-ING-GLORY | COCKLE-BUR | CASSIA | NUTS-EDGE |
|---|---|---|---|---|---|---|---|---|---|---|---|---|---|---|---|---|---|---|---|---|---|
| H | H | H | H | H | OCH₃ | Post | 2.0 | 8D | 5C | 2C | 8H | 2H | 0 | 2G | &P | 4G | 2G | 5C | 5C | 8G | &C |
|  |  |  |  |  |  | Post | 2.0 | 9G | 9G | 7G |  | 9G |  |  | 9G |  |  | 9G | 9G |  |  |
|  |  |  |  |  |  | Post | 2.0 | 6Y |  |  |  |  |  |  |  |  |  |  |  |  |  |
|  |  |  |  |  |  | Pre | 2.0 |  |  | 2H | 1C | 9H | 6G | 5G | &E | 2G | 3G | 9G | 9G | 9G | &E |
|  |  |  |  |  |  | Pre | 2.0 |  |  | 7G | 8G |  |  |  |  | 7G |  |  |  |  |  |
| Cl | H | H | H | H | OCH₃ | Post | 2.0 | 3C | 6C | 5U | 2U | 2C | 1C | 2C | 5C | &C | 6G | &C | 6C | &C | &C |
|  |  |  |  |  |  | Post | 2.0 | 9D | 9G | 9G | 9G | 9G | 6G | 5G | 9G |  |  |  | 9G |  |  |
|  |  |  |  |  |  | Post | 2.0 | 9G |  |  |  |  |  |  |  |  |  |  |  |  |  |
|  |  |  |  |  |  | Pre | 2.0 |  |  | &E | 9G | 9H | 9G | 7G | &E | 6C | 9G | &E | 9H | 9C | &E |
|  |  |  |  |  |  |  |  |  |  |  |  |  |  |  |  | 9C |  |  |  |  |  |
| CH₃ | H | H | H | H | OCH₃ | Post | 2.0 | &D | 7C | 5U | 9H | 2C | 5G | 7G | 5C | 2C | 5G | 5C | 2C | 1C | &C |
|  |  |  |  |  |  | Post | 2.0 | 9G | 9G | 9G |  | 9G |  |  | 9G | 9H |  | 9G | 9G | 9G | E |
|  |  |  |  |  |  | Pre | 2.0 |  |  | 9G | 9H | 9H | 9H | 8G | 2C | 9G | &E | 9H9G | 9C | &E |  |
|  |  |  |  |  |  | Pre | 2.0 |  |  |  |  |  |  |  |  | 9H |  |  |  |  |  |

TABLE V - G

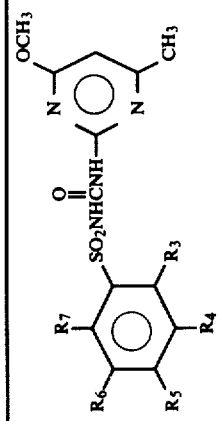

| R$_3$ | R$_4$ | R$_5$ | R$_6$ | R$_7$ | Mode of Application | Rate Kg/Ha | BUSH BEAN | COTTON | SORGHUM | CORN | SOYBEAN | WHEAT | WILD OATS | RICE | BARNYARD GRASS | CRAB-GRASS | MORNING-GLORY | COCKLE-BUR | CASSIA | NUTS-EDGE |
|---|---|---|---|---|---|---|---|---|---|---|---|---|---|---|---|---|---|---|---|---|
| Cl | H | H | H | H | Post | 0.4 | 9C | 9C | &C | &C | 8C | 8C | 9C | 9C | 9C | 5G | &C | &C | 6C | 5C |
|  |  |  |  |  | Post | 0.4 | &C | &C | &C | &C | 9C | 8C | &C | 9C | 9C | 3C | &C | &C | 5C | 9C |
|  |  |  |  |  | Post | 0.4 | 9C | 9C | 9H | &E | 9H | &E | 9H | &E | 9H | 8G | 9C | 9C | 9G | 9C |
|  |  |  |  |  | Pre | 0.4 |  |  | &H | &E | 9H | &H | 9H | &E | &H | 8G | 9H | 9H | 8G | 9G |
|  |  |  |  |  | Pre | 0.4 |  |  | &C | &E | 9H | 5C | 3C | 6G | 5C | 1C | 9C | 9G | 9H | &E |
|  |  |  |  |  | Pre | 0.4 |  |  |  |  | 9H | 9G | 9G |  | 9G | 9C |  | 9C | 9C |  |
| CH$_3$ | Cl | H | H | H | Post | 0.4 | 5C | 7C | 5H | 2H | 2H | 5G | 8G | 1C | 1C | 2G | 9C | 2C | 6G | 9G |
|  |  |  |  |  | Post | 0.4 | 9G | 9G | 8G | 8G | 9G |  | 1C | 7G | 1C | 1C | 9G | 8H | 8G | &E |
|  |  |  |  |  | Pre | 0.4 | 0.4 |  | 2C | 9H | 9H | 1C | 8G | 9H | 9H | 8H |  | &E | 9G |  |
| F | Cl | H | H | H | Post | 0.4 | 5S |  |  | 6C | 2C | 2G | 0 | 8G | 2C | 1C | 3G | 7G | 5G | 9C |
|  |  |  |  |  | Pre | 2.0 | Post 6Y | 2.0 | 9G | 9G |  |  | 8G | 6G |  | 3G |  |  | 9G |  |
| F | H | H | Cl | H | Post | 2.0 |  |  | 2C | 9G | 2C | 6G | 3G | 9H | 2C | 5G | 9G | 9C | 8G | 8E |
|  |  |  |  |  | Pre | 2.0 |  |  | 8H | 9H | 6H |  |  | 9C | 7G | 3C |  |  |  |  |
|  |  |  |  |  | Post | 2.0 | 9C | 9C | 3C | 3C | 3C | 9G | 9G | 9C | 199 2C | 5G | 6G | 9C | 9C | 8C |
|  |  |  |  |  | Post | 2.0 |  |  | 9G | 9G | 8H | 2C | 9G | &E | 9H | 4G | 9G | 9C | 9H | 9G |
|  |  |  |  |  | Pre | 2.0 |  |  | 9G | 9G | &E | 5G | 6G | 6G | 2C | 2G | 9G | 9G | 8G | &E |
| CH$_3$ | H | H | Cl | H | Post | 0.4 | 5C | 2H | 9H | 9H | 2C | 2C | 9H | 2C | 1C | 9G | 9G | 8G | 3C | 9G |
|  |  |  |  |  | Post | 0.4 | 9G | 5C |  |  | 9G | 9G |  |  | 3G | 1C | 5C |  | 9C |  |
|  |  |  |  |  | Post | 0.4 |  | 9G |  | 9G |  |  |  |  | 9C | 6G | 9G |  | &E |  |
| OCH$_3$ | Cl | H | H | H | Post | 0.4 | 5C | 6C | 3H | 3C | 2C | 2C | 2C | 2C | 1C | 1C | 5C | 2C | 6C | 3C |
|  |  |  |  |  | Post | 0.4 | 9G | 9G | 9G | 9G | 9H | 9G | 9G | 9C | 3G | 6C | 9G | 8G | 9C | 9G |
|  |  |  |  |  | Post | 0.4 |  |  | 9H | 9G |  | 9H | 2C | &E | 9C | 1C | 9G | 9G | 5C | &E |
|  |  |  |  |  | Post | 0.4 | 4S | 2H |  | 2C | 2C | 0 | 9G | 2G | 2C | 5G | 2C | 2C | 9G |  |
|  |  |  |  |  | Post | 0.4 | 7G | 5C | 5G | 7G | 3H |  | 0 |  | 9H | 0 |  | 8G | 1C | 9C |
| H | H | H | H | H | Post | 0.4 | 64 | 9G | 3H | 7G | 1C | 9H | 7G | 8G | 8C | 2C | 0 | 5G | 8G | 8G |
|  |  |  |  |  | Post | 0.4 | 0.4 |  | 9G | 9G | 8C |  |  |  | 1C | 4C | 8C | 9C | 5C | 9C |
| F | H | F | H | H | Pre | 0.4 | 3S | 7C | 9G | 3U | 2C | 8G | 2C | 2C | 7G | 1C |  |  |  |  |
|  |  |  |  |  | Post | 0.4 | 7G | 9G | 7G | 9G | 8G | 2C | 7G | 7G | 1C | 6C |  |  |  |  |
|  |  |  |  |  | Post | 0.4 | 6Y |  | 5L |  |  |  |  |  | 9L | 5C |  |  |  |  |
|  |  |  |  |  | Pre | 0.4 |  |  | 9H | 9G | 9H | 9G | 8G | &E | 2C | 3G | 9G | 9G | 9C | &E |

TABLE V - G-continued

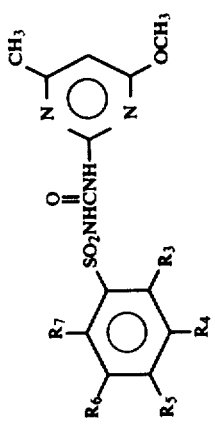

| R1 | R4 | R5 | R6 | R7 | Mode of Application | Rate Kg/Ha | BUSH BEAN | COTTON | SORGHUM | CORN | SOYBEAN | WHEAT | WILD OATS | RICE | BARNYARD GRASS | CRABGRASS | MORNING GLORY | COCKLEBUR | CASSIA | NUTSEDGE |
|---|---|---|---|---|---|---|---|---|---|---|---|---|---|---|---|---|---|---|---|---|
| F | H | H | H | F | Post | 0.4 | 9C | 9C | 9U 9H | &C &E | 6C 9H | &P &E | 5C 9H 86 | 9C &E | 9C 9H | 5C 1C | 9C 9G | &C 9C | 9C 9C | 9C &E |
|  |  |  |  |  | Pre | 0.4 |  |  |  |  |  |  |  |  |  |  |  |  |  |  |
| Cl | H | H | H | Cl | Pre | 0.4 |  | 9C &E | &C &E | 9C 9H | 5C &E | 6C &E | 9C &E | 9C 9H | 9C 9H | 3C 9G 9C 1C 4G | 9C &E | &C 9C | &C &E | 9C |
| Cl | Cl | H | H | H | Pre | 0.4 | 9C | 9C | 5U 9G | 9C | 6C 9H | 3C 9G | 1C 9G | 9C | 3C 9H | &C | &C |  |  |  |
|  |  |  |  |  | Post | 0.4 | 5C 9G 6Y |  |  |  |  |  |  |  |  |  |  |  |  |  |
| H | Cl | Cl | H | H | Post | 0.4 | 3H 7G 6F | 5C 6G | 9H | &E | 9H | 9H | 9G | &E | 3C 9H 2G | 4C 8G 0 | &E | 3H 9G | 4H | &E |
|  |  |  |  |  | Post | 2.0 | 4H 9G 6Y | 6C 9G | 8H | 8H | 3H 8G | 0 | 0 | 6H | 1C 5G 2C 9H | 0 | 5C 9G | 9C | 9G | 1C 5G |
| F | H | H | CH3 | H | Post | 2.0 |  |  | 2C 7H 2U 9G | 3C 9H 9G | 8H 5C 9G | 8G 4G | 4G 5G | 9H | 9H 2C 9H | 2G 6G | 9G 3C 9G | 9C | 9G | 1C 7G 9C |
|  |  |  |  |  | Post | 2.0 |  |  |  |  |  |  |  |  |  |  |  |  |  |  |
|  |  |  |  |  | Post | 0.4 | 3H 8G 6Y | 5C 9G | 2H 9G | 9G | 9H 5 | 8G | 1C 9G | &E 2C 8G | 9H | 7G | &E | 9C | 9G | &E |
|  | H | H | F | H | Pre | 0.4 |  |  |  |  |  |  |  |  |  |  |  |  |  |  |
| CH3 |  |  |  |  | Post | 0.4 |  |  | 9H 5U 9G 3H 9G | 9G &C | 4C 9G 9G 9H | 9H 1C 4G 9H | 9H 1C 9G | &E 2C 8G &E | 9H &C &H | 4G 6G 1H 4G | 5C 9G 9G &C | 3H 9G 9C &E | 9G 9C | &C 9C |
| Cl | H | H | OCH3 | H | Pre | 0.4 | 9C | 9C | &E | &E | 9H | 9C | 9G | &E | 9C | 6G 9G 5C 1C | 9G | 9C | 8C | &C |
| Cl | H | H | H | H | Post | 0.4 | 9C | 9C | &C &E | &C &E | 5C 9H | 8C &E | 9C 9G | 9C &E | &C 9C | 9G 6C 1C | 9C &C | 9C &E | 9G | 9C |
| Cl (sodium salt) | H | H | H | H | Pre | 0.4 | 9C | 9C | &C &E | &C &E | 5C 9H | 8C &E | 9C 9G | 9C &E | &C 9C | 5C 1C 9G | 9C | 9C | 9C | 9C |
| Cl (potassium salt) | H | H | H | H | Post | 0.4 | 9C | 9C | &C &H | &C &E | 5C 9H | 8C &E | 8C 9G | 9C &E | &C 9C | 6C 1C 9G | &C 9G | 9C 9G | 9C 9G | &C 9G |
|  |  |  |  |  | Pre | 0.4 |  |  |  |  |  |  |  |  |  |  |  |  |  |  |
| Cl (p-toluene sulfonic acid salt) | H | H | H | H | Post | 0.4 | 9C | 9C | &C 9H | &C &E | 5C 9H | 8C &E | 8C 9G | 9C &E | &C 9C | 2C 1C 8G | 9C 9G | 9C 9G | 9C 9G | 9C &E |
|  |  |  |  |  | Pre | 0.4 |  |  |  |  |  |  |  |  |  |  |  |  |  |  |

TABLE V - G-continued

| R₃ | R₄ | R₅ | R₆ | R₇ | Mode of Application | Rate Kg/Ha | BUSH BEAN | COTTON | SOR-GHUM | CORN | SOY-BEAN | WHEAT | WILD OATS | RICE | BARN-YARD-GRASS | CRAB-GRASS | MORN-ING-GLORY | COCKLE-BUR | CASSIA | NUTS-EDGE |
|---|---|---|---|---|---|---|---|---|---|---|---|---|---|---|---|---|---|---|---|---|
| F | H | H | H | H | Pre | 0.4 | 9C | 9C | &C | &C | &C | 9C | 9C | 9C | &C | 2C | &C | 9C | &C | 1C |
| | | | | | Post | 0.4 | | | 2C | &E | 1H | 1C | 1C | &E | 1C | 1C | 9G | 8G | &E | &E |
| CH₃ (sodium salt) | H | H | H | H | Pre | 0.4 | 6C | | 9G | &C | 9G | 9G | 9G | 5C | 9C | 9G | 9C | 9C | 5C | |
| | | | | | Post | 0.4 | 9G | | 3C | | 5C | 3C | 2C | 8G | 4C | 7G | | | 8G | |
| | | | | | Pre | 0.4 | | | 9G | | 5C | 7G | 8G | &E | 9C | 5G | | | 9G | |
| | | | | | Post | 0.4 | | | &E | &E | 9H | 9H | 2C | &E | 5C | | | | | |
| H | H | H | CF₃ | H | Pre | 2.0 | 8C | 3B | 2H | 3H | 9C | 6G | 7G | 3C | 3C | 2C | 9C | 9C | &C | &E |
| | | | | | Post | 2.0 | 8D | 5H | 8G | 9G | | | 5L | 9G | | 8G | | | | |
| | | | | | | | | 9G | | | | | | | | | | | | |
| CH₃ | H | H | CH₃ | H | Pre | 2.0 | 5C | 5H | &E | 5C | 9H | 5C | 8C | &E | 3C | 2C | &E | 9G | &E | 1C |
| | | | | | Post | 2.0 | 9H | 9G | 3H | 9G | | 8G | 8G | &C | 6G | 8G | | | | 8G |
| | | | | | | | | | 9G | 9H | | | 5G | | &C | 5C | | | | 8G |
| OCH₃ | Cl | H | H | H | Pre | 2.0 | 2H | 2H | 2H | 9H | 9H | 9H | 1C | &E | 9H | 8G | 9G | 9G | 9G | 9G |
| | | | | | Post | 2.0 | 9D | 9G | 9G | 5C | 5C | | 9G | 9G | 2C | 8G | 5C | 2C | | |
| | | | | | | | 9G | | 9G | 9G | | | 8G | | 9H | | 9G | 9G | | |
| CH₃ | H | H | Br | H | Pre | 2.0 | 7C | 7C | 5U | &C | 2C | 1C | 1C | 8G | 9H | 3G | 9C | 9C | 9C | &C |
| | | | | | Post | 2.0 | 9G | 9G | 9G | 9H | 9H | 6G | 2G | 7G | 9C | | 8C | 9C | 9C | |
| | | | | | | | | | 9H | | | | 8G | | | | | | | |
| Cl | H | H | H | H | Pre | 0.4 | 8C | 8C | 2H | &C | 1C | 2C | 1C | 5C | 3C | 3C | 9C | 9C | 2C | 8C |
| | | | | | Post | 0.4 | 9G | 9G | 9G | 9H | 2H | 8G | 8G | 9G | 9H | 8G | | | 7G | &E |
| | | | | | | | | | 9H | | 9H | | 9G | &E | | 2C | | | 9G | |
| CH₃ | H | CH₃ | H | CH₃ | Pre | 0.4 | 2S | 3C | 2H | 6G | 2H | 0 | 1C | 8G | 9H | 2C | 2C | 2C | 1C | 6G |
| | | | | | Post | 0.4 | 8G | 2H | 9G | | 8G | 0 | 9G | 0 | | 5G | 8G | 9G | 5G | |
| | | | | | | | 6F | 9G | | | | | | | | 0 | | | | |
| Cl | H | Cl | H | H | Pre | 0.4 | 3S | 5C | 9G | 9H | 4H | 9G | 8G | &E | 9H | 0 | 8G | 8G | 8G | &E |
| | | | | | Post | 0.4 | 8G | 8G | 9H | 8H | 3H | 0 | 0 | 5G | 1C | 0 | 2H | 2H | 5D | 7G |
| | | | | | | | 6F | | | | 9G | | | | | | 8G | 8G | 5G | 5X |
| Cl | H | H | H | H | Pre | 0.4 | | 5G | 1C | 8G | 7H | 4G | 2G | 5G | 3C | 3G | 8G | 8G | 9G | 9G |
| | | | | | Post | 0.4 | 5C | 2C | 5C | 4C | 9C | 5C | 8G | 5C | 6C | 5C | 5C | 3H | &P | 9C |
| Cl | H | H | NO₂ | H | Pre | 0.4 | | | | | | | | | | | | | | |

TABLE V - G-continued

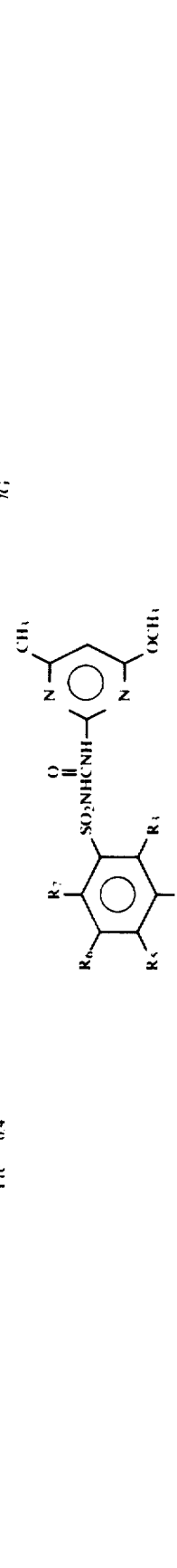

| R₃ | R₄ | R₅ | R₆ | R₇ | Mode of Application | Rate Kg/Ha | BUSH BEAN | COT- TON | SOR- GHUM | CORN | SOY- BEAN | WHEAT | WILD OATS | RICE | BARN- YARD- GRASS | CRAB- GRASS | MORN- ING- GLORY | COCKLE- BUR | CASSIA | NUTS EDGE |
|---|---|---|---|---|---|---|---|---|---|---|---|---|---|---|---|---|---|---|---|---|
| CH₃ | | | | | Pre | 0.4 | 9G 0.4 | 3H 6Y | 9G 9H | 9H | 9H | 8G | | 7G | 9G | 9G | 9G | 9G | 9G | |
| | CH₃ | H | CH₃ | CH₃ | Pre | 0.4 | | | 9H | 9G | 9H | 9G | 2C 8G | &E | 9H | 9G | 9G | 9G | 9G | &E |
| | | | | | Post | 0.4 | 4S 7G 6Y | 2C | 2G | 3H | 2H | 9G 0 | 0 | 4G | 8C | 3G | 1C | 1C | 1C | 0 |
| OC₂H₅ | H | H | OC₂H₅ | H | Pre | 0.4 | | | | | | | | | | | | | | |
| | | | | | Pre | 0.4 | 5C 9G | 9C | 2U 2U 8G 2U 9G | 2C 5G 1C 9G 2U 9G | 1C 4H 9G 9H | 4G 1C 6G 9H | 3G | 8G | 2C 8G 3C 9H 9G 1C | 1C 4G 2C | 8G | 5G | 2G 9H 9H 8G 3C | 1C | 8G |
| CH₃ | H | H | CH(CH₃)₂ | H | Pre | 0.4 | 3H 4C 9G | 6C 9G | 7G | 9H 9G | 3C | 0 | 0 | 5G 3G | 9G 1C | 2G 9G | 5C 9G | 8G | 2C | 9G |
| OCH₃ | H | H | CH₃ | H | Pre | 0.4 | 8C 7G | 9C | 9G 3C 4G &E | 9H 3C 5G 9G | 8H 7C 6G 7G | 5G 4G | 5G | 9H 5C 5G &E | 9H 8C | 2G 7C | &C | 5C | 7C | 7C 9G 3C |
| OC₂H₅ | H | H | Cl | H | Pre | 0.4 | 5C 9G 6Y | 9C | 2C 8G | 3C 5G 9G | 3C 9G | 2C 5G | 7G | 2C 7G | 8G 5C 9G | 6G 5G | 7G | 5G | 3G | &P 8G | &E |
| | 152 6Y | &E | | 9G | Post 9H | 0.4 9H | 1C | &E | 9H | 8G | 9G | &E | 9G | &E | | | 9C | 3C 8H | &P 8G | 9C |
| CF₃ | H | H | H | H | Pre | 0.4 | 9C | 9C | 9C &E | 9U &E | 5C 9H | 2C 9H | 8G 2C 4C 9H 2C 4C 8H | 4C &E | 9C 9H | 8C 9H | &C &E | 5C &E | 9C &G | 9C &E |
| OCH₃ | H | H | H | H | Post | 0.4 | 9C | 9C | 5U 9H | 9C &E | 9C 9H | 9C 9H | 0 | 3C &E | 9C 9H | 9C &E | &C &E | 5C 8G | &C 9G | 4C &E |
| O(CH₂)₃CH₃ | H | H | O(CH₂)₃CH₃ | H | Post | 0.4 | 2C 5G 6Y | 1C 4H | 0 | 0 | 1C | 0 | 0 | 0 | 0 | 0 | 1C 3H | 2C | 2C | 0 |
| | | | | | Pre | 0.4 | | | 3G | 3G | 0 | 0 | 0 | 7G | 0 | 0 | 0 | 0 | 0 | 0 |

TABLE V - G-continued

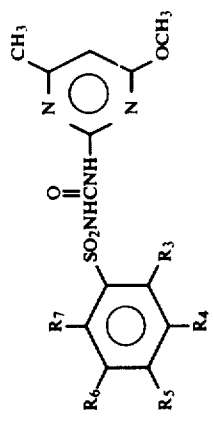

| R₃ | R₄ | R₅ | R₆ | R₇ | Mode of Application | Rate Kg/Ha | BUSH BEAN | COT-TON | SOR-GHUM | CORN | SOY-BEAN | WHEAT | WILD OATS | RICE | BARN-YARD-GRASS | CRAB-GRASS | MORN-ING-GLORY | COCKLE-BUR | CASSIA | NUTS-EDGE |
|---|---|---|---|---|---|---|---|---|---|---|---|---|---|---|---|---|---|---|---|---|
| OCH₃ | H | OCH₃ | H | H | Pre | 0.4 | 3S 8G 6Y | 2C 5G | 2C 8G | 9H | 1C 1H | 4G | 6G | 3C 9G | 1C 9H | 5G | 2C 4H | 3C | 4C | 1C 4G |
|  |  |  |  |  | Post | 0.4 |  |  |  |  |  |  |  |  |  |  |  |  |  |  |
| H | CH₃ | H | H | H | Pre | 0.4 | 3C 8G 6Y | 9C | &E 2U 9G | 9G 2U 9G | 2G 9C | 9H 4G | 1C 8G 8C | &E 5C 8G | 9H 2C 9C | 9H 2C 9G | 9G | 8C | 7G 9C | 2C 5H 6C 9G | 2C 7G 3C 9G |
|  |  |  |  |  | Post | 0.4 |  |  |  |  |  |  |  |  |  |  |  |  |  |  |
| H | CH₃ | CH₃ | H | H | Pre | 0.4 | 1C | 5G | &E 0 2G &E 9C | 9G 3H 2C 9C | 9H 1H 0 9C | 9G 0 7C 9C | 8G 0 1C 8C 7C | &E 2G 6G 8C 7G &E | 9H 1C 3C 9C | 8G 0 2G 9C 5C 8G 9G | &E 0 9G 9C | &E 1C &E 9C | 9G 0 9G 6C 9G | &E 0 &C &C |
|  |  |  |  |  | Post | 0.4 |  |  |  |  |  |  |  |  |  |  |  |  |  |  |
| NO₂ | H | H | H | H | Pre | 2.0 | 9C 9C | 9C 9C | &E &E | &E &E | 9H 9H | 9H 9H |  | &E &E | &H 9H | 9G | &E &E | &E 9G | 9G 9G | &E &E |
|  |  |  |  |  | Post | 0.4 |  |  |  |  |  |  |  |  |  |  |  |  |  |  |
|  |  |  |  |  | Pre | 2.0 |  |  |  |  |  |  |  |  |  |  |  |  |  |  |
|  |  |  |  |  | Post | 0.4 |  |  |  |  |  |  |  |  |  |  |  |  |  |  |
| Cl | Cl | Cl | H | H | Pre | 2.0 | 3S 8G 6Y | 3H 3C 8G | 4G | 9H | 3C 8G | 3G | 5G | 3G | 2G | 2G | 3C 8G | 5C 9G | 1C 5G | 2C 7G |
|  |  |  |  |  | Post | 2.0 |  |  |  |  |  |  |  |  |  |  |  |  |  |  |
| Cl | Cl | H | Cl | H | Pre | 2.0 | 3C 8G | 3C 9G | 0 | 1C 6G 4H | 5H | 0 | 0 | 6G | 4H | 0 | 9G | 9G | &E | 5G |
|  |  |  |  |  | Post | 2.0 |  |  |  |  |  |  |  |  |  |  |  |  |  |  |
| Cl | Cl | H | H | H | Pre | 2.0 | 3C 7G 6Y | 3C 9G | 2G | 1C 7G 9H | 3H 9G | 0 | 0 | 3G | 3G | 2G | 5C 9G | 2C 9H | 2C | 2C 7G |
|  |  |  |  |  | Post | 2.0 |  |  |  |  |  |  |  |  |  |  |  |  |  |  |
| Cl | H | H | Cl | H | Pre | 2.0 | 4S 8G 6Y | 7C 9G | 4G 1U 9G | 1C 7G 9H | 2C 8G 3H 9G | 3G 4G | 2G 5G | 9H 8H 1C 7G | 9H 8H 1C 7G | 3G | 3C 8G | &P 9G | &E 2C 9G | 9G 5G | 5G 8G |
|  |  |  |  |  | Post | 0.4 |  |  |  |  |  |  |  |  |  |  |  |  |  |  |
| Cl | H | H | H | H | Pre | 2.0 | 8C 9G | 8C 9G 7D | 9H 9U 9G | &H 9C | 9H 6C 9G | 9H 3C 9G | 8H 2C 9G | &E 6C 9G | 9H 9C | 3C 2H 5G | 9G 6C 9G | 9G | 3C 8G 9G | 9G 8G | 8G |
|  |  |  |  |  | Post | 0.4 |  |  |  |  |  |  |  |  |  |  |  |  |  |  |
| Cl | CH₃ | H | H | H | Pre | 2.0 |  |  | &E | &E | 9H | 9H |  | &E | &E | 1C 8G | 9G | 9C | 9G | &E |
|  |  |  |  |  | Post | 0.4 |  |  |  |  |  |  |  |  |  |  |  |  |  |  |
| Br | H | H | H | H | Pre | 2.0 | 9C | 9C | &C | &C | 9C | — | 9C | &C | 9C | &C | 5C | &C | &C | 9C | &C |
|  |  |  |  |  | Post | 0.4 |  |  |  |  |  |  |  |  |  |  |  |  |  |  |

TABLE V - G-continued

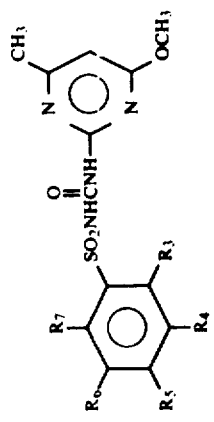

| R₁ | R₄ | R₅ | R₆ | R₇ | Mode of Application | Rate Kg/Ha | BUSH BEAN | COTTON | SORGHUM | CORN | SOYBEAN | WHEAT | WILD OATS | RICE | BARNYARD-GRASS | CRAB-GRASS | MORNING-GLORY | COCKLE-BUR | CASSIA | NUTS-EDGE |
|---|---|---|---|---|---|---|---|---|---|---|---|---|---|---|---|---|---|---|---|---|
| | | | | | Pre | 0.4 | | | | | | | | | | | | | | |
| H | Cl | H | H | H | Pre | 0.4 | 3H | 2H | 2C | 9H | 5C | 4G | 9H | &E | &H | 1C | &E | 9G | 9G | 9G |
| | | | | | Post | 0.4 | 9D | 4C | 9H | | 9G | | 1C | 8G | 2G | 8G | 2H | 5C | 5C | 8G |
| | | | | | | | 9G | 9G | | | | | 5G | | | 2G | 7G | 9G | 8G | |
| CH₃ | H | H | H | H | Pre | 0.4 | 5C | 9C | 9H | 9H | 9H | 8G | 8G | &E | 2C | 2C | 5C | 8C | 7C | &E |
| | | | | | Post | 0.4 | 9G | | | | | | 2C | 5C | 8G | 5G | 8G | | | |
| | | | | | | | 6F | | | | | | 7G | 8G | 9C | 7G | | | | |
| | (benzyltrimethyl ammonium salt) | | | | Pre | 0.4 | | | 9G | &E | 9G | &E | 2C | &E | 9C | 2C | 9G | 9G | 9G | &E |
| | | | | | Post | 0.4 | | | | | 5H | 9H | 3G | 5G | 9G | | | | | |
| Br | H | H | Br | H | Pre | 0.4 | 4C | 8C | 8H | 9H | 5H | 2G | 3G | | 8H | 1H | 9C | 9C | 5C | 4C |
| | | | | | Post | 0.4 | 9G | 9G | | | 9G | | | | | | | | 9G | 9G |
| | | | | | | | 6Y | | | | | | | | | | | | | |
| OCH₃ | H | H | OCH₃ | H | Pre | 0.4 | 9C | 9C | 8H | 9G | 9H | 8G | 8G | &E | 9H | 5G | 9G | 9G | 9G | 9G |
| | | | | | Post | 0.4 | | | 5U | 9H | 6C | 4G | 4C | 4C | 9C | 5C | &C | &C | 9C | 5C |
| | | | | | | | | | &H | &E | 9H | &E | 9H | &E | 9H | 2G | 9G | 9G | 9G | &E |
| Cl | Cl | H | Cl | Cl | Pre | 2.0 | 4C | 9C | 2U | 8H | 3C | 7G | 2C | 5G | 3C | 3H | 9G | 9C | 9C | 5C |
| | | | | | Post | 2.0 | 9G | | 9H | | 9G | | 9G | 9H | 9H | | | | | 8G |
| | | | | | | | 6Y | | | | | | | | | | | | | |
| Cl | H | H | H | CH₃ | Pre | 2.0 | 9C | | 9H | 9G | 9C | 9G | 5C | &P | 9C | 1C | 9G | 9G | 2C | 9C |
| | | | | | Post | 2.0 | | | 5U | 9U | 9H | 1C | 3C | &E | 9H | 7G | &C | &C | 9G | &E |
| | | | | | | | | | &E | &E | | 9H | 9H | | | 6C | &E | | | |
| | | | | | | | | | | | | | 9H | | | 9H | | | | |
| H | H | H | H | H | Pre | 2.0 | 7C | 6C | 1C | 2C | 3C | 2C | 2C | 5C | 2C | 2C | &C | 5C | 8G | 5C |
| | | | | | Post | 2.0 | 9G | 9G | 9G | 9G | 8G | 9G | 9G | 8G | 9G | 7G | | 9G | | &E |
| | | | | | | | | | 9G | &E | 9G | &E | 8G | &E | 1C | 1C | | | | |
| | | | | | | | | | | | | | 7H | | &C | 5G | | | | |
| | | | | | | | | | | | | | &C | | | 8C | | | | |
| CH₃ | H | H | H | H | Pre | 0.4 | 9G | 9G | &E | &E | 9C | 9C | 3C | &E | 2C | 3C | 9C | 9C | 9C | 9C |
| | | | | | Post | 0.4 | 9C | 9C | | | 9G | | 9H | | 9H | 8C | | | | &E |
| CH₃ | H | H | H | H | Pre | 0.4 | | 4C | 3& | 9C | 3C | 1C | 3C | &E | 2C | 3C | &E | 9C | &E | 3C |
| | | | | | Post | 0.4 | 3C | 9G | 9G | | 9G | 8G | 9H | | 9H | 9G | 8G | 9G | | 9G |
| CH₃ | H | H | NO₂ | H | Pre | 0.4 | 9G | | | 9C | 3C | 1C | 8G | 2C | 2C | 3C | 2C | 2C | 3C | 3C |
| | | | | | Post | 0.4 | 6Y | | | | 9G | 8G | | 8G | 9H | 6G | 8G | 9H | 7G | 9G |
| | | | | | | | | | | | | | | | | | | | | &E |

TABLE V - G-continued

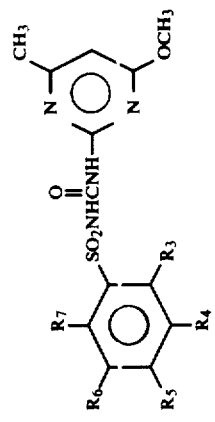

| | | | | Pre | 0.4 | | | | | | | | | | | | 7G | |

| $R_3$ | $R_4$ | $R_5$ | $R_6$ | $R_7$ | Mode of Application | Rate Kg/Ha | BUSH BEAN | COT-TON | SOR-GHUM | CORN | SOY-BEAN | WHEAT | WILD OATS | RICE | BARN-YARD-GRASS | CRAB-GRASS | MORN-ING-GLORY | COCKLE-BUR | CASSIA | NUTS-EDGE |
|---|---|---|---|---|---|---|---|---|---|---|---|---|---|---|---|---|---|---|---|---|
| Cl | H | H | CH(CH$_3$)$_2$ | H | Pre | 0.4 | | | &E | 9G | 9H | 9H | 1C 8G 7G | 9H | 9H | 1C 7G | 9G | 8G | 8G | &E |
| | | | | | Pre | 0.4 | | | | | | | | | | | | | | |
| | | | | | Post | 0.4 | 5H | 6C | 3U | 9G | 2C | 7G | | 3C | 2C | 6G | 7C | 3C | 6C | 9G |
| | | | | | Post | 0.4 | 9G 6Y | 9G | 9G | | 9G | | | 9G | 9H | | 9G | 9G | 9G | |
| F | H | F | H | F | Pre | 0.4 | | | | | | | | | | | | | | |
| | | | | | Post | 0.4 | 3S 6G 6Y | 3H 5C 9G | &E 6G | 9G 2H 7G | 9H 2H 6G | 9H 3G | 9G 0 | &E 7G | 9H 5G | 9G 0 | &E 2C 6H | 8G 5C 9G | 9G 2A | &E 7G |
| | | | | | Post | 0.4 | | | | | | | | | | | | | | |
| Cl | H | Cl | H | Cl | Pre | 0.4 | | | | | | | | | | | | | | |
| | | | | | Post | 0.4 | 5S 9G 6Y | 4C 8D 9G | 8H 3G | 7G 2G | 3G 2H 8G | 5G 0 | 3G 0 | 9H 0 | 6G 3G | 2G 0 | 9G 5C 7G | 9G 3C 9G | 7G 1C | &E 9G |
| | | | | | Post | 0.4 | | | 7G | 6C 9G | 2H | 5G | 6G | 0 | 5H | 2G | 9G | — | 5G | &E |
| | | | | | Pre | 0.4 | | | | | | | | | | | | | | |
| | | | | | Pre | 0.4 | | | | | | | | | | | | | | |

TABLE V - H

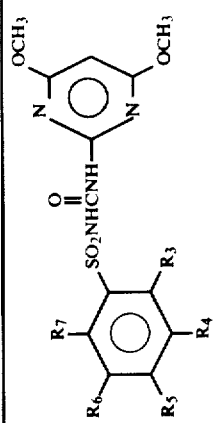

| $R_1$ | $R_4$ | $R_5$ | $R_6$ | $R_7$ | Mode of Application | Rate Kg/Ha | BUSH BEAN | COTTON | SORGHUM | CORN | SOY-BEAN | WHEAT | WILD OATS | RICE | BARN-YARD GRASS | CRAB-GRASS | MORN-ING-GLORY | COCK-LE-BUR | CASSIA | NUTS-EDGE |
|---|---|---|---|---|---|---|---|---|---|---|---|---|---|---|---|---|---|---|---|---|
| $CH_3$ | H | H | H | H | Post | 2.0 | 9C | 4H 9G | 2U 7G | 9C | 9C | 7G 8G 9G | | 5C 9H &E | 6C 9H | 7G | &C | 9C | &C | 9C |
| $OCH_3$ | Cl | H | H | H | Post | 2.0 | | 6C 9G | 1C 9G | 9G | 9H | 0 | 0 | | 9H | 7G | | | 8G | &E |
| | | | | | Pre | 2.0 | 9C | | 2H 7G | 9C | 5C 9G | 4G | 3G | 3C 8G &E | 3C 8H | 2G | 2H 9G | 5C 9G | 2C 9G | 2C 9G |
| $CH_3$ | H | F | Br | H | Pre | 0.4 | 6C | 5C 2U | 1C 9G 7H | 2H 9G | 2G 9H | 2G 3G | 8G 3G | 9H 9H | 2C 3G 9H | &C 2C 6G | 4C 8G 9G | 9G 9C | 4C 8G 9G | &C &E |
| Cl | H | $CH_3$ | H | H | Post | 0.4 | 8C 9G | 8C 9G | 2U 9G 9H | 9H | 3C 9H | 2G 3G | 1C | 3C 9G &E | 9C | 1C 5G 2C 6G | 4C 8G | 9G | 4C 8G 9G | |
| $CH_3$ | H | H | H | $CH_3$ | Pre | 0.4 | 2C 9G 6F | 2C 2H 9G | 2U 9G 1C 7G | 1C 6G | 2H 9G | 7G | 6G | &E | 2C 8H 3H | 1C 5G 2C 6G 0 | 2C 9G | 3H 9G | 2C 8G | 6G &E |
| Cl | H | Cl | H | H | Post | 0.4 | 6C 9G | 5C 9G | 2U 9G | 1C 5G 7G | 3H 9G 8H | 0 | 2G | 7G | 3H | 3G | 9G | 9G | 9G | &E |
| $CH_3$ | H | H | $NO_2$ | H | Pre | 0.4 | 5C 9G 6Y | 2C 4H 9G | 2G 9G | 2H 9G | 9C | 0 | 0 | 2G | 0 | 0 | &C | 9C | 4C 7G 8G | 2C 8G &E |
| Cl | H | H | $OCH_3$ | H | Post | 0.4 | 9C | 5C 9G | 3G 9G | 1C 9H | 4C 9G 9G | 1C 6G | 7G | 5C 8G | 1C 3G 9G | 3G | 9G | 9G | &P 9G | 5C 8G &E |
| Cl | H | H | H | H | Post | 0.4 | 9C | 9C | 2G 9G | 2H 9G | 2C 8G | 0 | 3G | &E | 9H | 4C 9G | &C | 9C | 9C | &E |
| Cl | H | H | H | $CH_3$ | Pre | 2.0 | 2C 7D 9G | 5C 9G | 1U 9G 9H 2H | 1C 9H 2H 9G | 4C 9G &E 2C 8G | 5G 5G 2G | 5G 5G 8G | 1C 6G 9H &E 1C | 2C 9H 9H 7G | &E 6G 9H 5G | 9C 9G &E 9C | 8G 9G 3C 9G | 8G 6C &P 9G | 9C 5C &E 8G |
| Cl | H | H | H | H | Post | 2.0 | | 5C 9G | 6G | 9G | 9G | 5G | 7G | &E | 5L 1C | 1C | 9G | 8G | 8G | &E |

TABLE V - H-continued

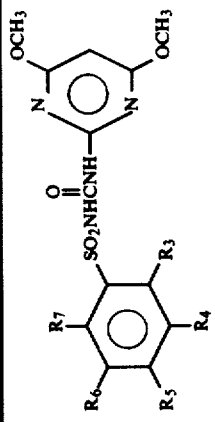

| R3 | R4 | R5 | R6 | R7 | Mode of Application | Rate Kg/Ha | BUSH BEAN | COTTON | SORGHUM | CORN | SOY-BEAN | WHEAT | WILD OATS | RICE | BARN-YARD GRASS | CRAB-GRASS | MORN-ING-GLORY | COCK-LE-BUR | CASSIA | NUTS-EDGE |
|---|---|---|---|---|---|---|---|---|---|---|---|---|---|---|---|---|---|---|---|---|
| Cl | H | H | Cl | H | Pre | 2.0 | 5C 9G 6Y | 3C 7D 9G | 5G | 6G | &C | 0 | 0 | 2G | 6G 7G 9L | 6G 3G | 9C | &C | 8C | 9C |
|  |  |  | (sodium salt) |  | Post | 0.4 |  |  |  |  |  |  |  |  |  |  |  |  |  |  |
| Cl | H | H | CH3 | H | Post | 0.4 | 5C 9G 6Y | 7C 9G | 8H 2U 8G | 9G 8G | 9H 3H 8G | 5G 4G | 2G 1C | 9H 3H 7G | 9H 5C 9H | 0 7G | &E 9C | 9G 9C | 9G 9C | &E |
|  |  |  |  |  | Pre | 0.4 |  |  |  |  |  |  |  |  |  |  |  |  |  |  |
| CH3 | H | H | NO2 | H | Post | 0.4 | 3C 9G 6Y | 3C 9G | 9H 5U 8G | 9G 7U 9G | 9H 9C | 8G 1C 8G | 8G 1C 8G | &E 3C 8G | 9H 3C 8H | 9G 2C 8G | 9G 9C | 9G 9C | 9G 3C 9G | &E 6C 9G |
|  |  |  |  |  | Pre | 0.4 |  |  |  |  |  |  |  |  |  |  |  |  |  |  |
| CH3 | H | H | (CH(CH3)2 | H | Post | 0.4 | 6C 9G |  | 9G | 9G | 9H | 9G | 9G | 9H | 9H | 1C 9G 2G | 9C | &C 9G | 8G | &E |
|  |  |  |  |  | Pre | 0.4 |  |  |  |  | 3H 9G 5H |  |  |  |  |  |  |  |  |  |
| OCH3 | H | H | F | H | Post | 0.4 | 5D 9G 6Y | 5C 9G | 3C 9G 9G | 9H 9C | 3H 9G 5H | 3G | 3G | 7G | 1G 2C 9H | 9G 2G 3G | &C 9G | 3C 9G 8G | 3C 6G 2C | &E |
|  |  |  |  |  | Pre | 0.4 |  |  |  |  |  |  |  |  |  |  |  |  |  |  |
| F | H | H | H | H | Post | 0.4 | 3C 8G 6Y | 8C 9G | 5U 9G | 90 | 90 | 40 7G | 50 7G | 60 9G | 2C 9H 9C | 5C 9G | 9G | 9C | 9C | 9G |
|  |  |  |  |  | Pre | 0.4 |  |  |  |  |  |  |  |  |  |  |  |  |  |  |
| OCH3 | H | H | CH3 | H | Post | 0.4 | &C |  | 2C 8G | 9G 51 | 9H | 9H 5G | 9H 2C 9G | &E | 9H | 6C 9G 6G | 9C | 9C | 5C 8G 9C | &E 7C 9G |
|  |  |  |  |  | Pre | 0.4 |  |  |  |  |  |  |  |  |  |  |  |  |  |  |
| F | H | H | H | H | Post | 0.4 |  | 7C 7G | 9H 5C 3G | 9G 6G | 9H 8C 7G | 7G 5G | 7G 4G | 5C 8G | 2C 9H 9C | 9G 2G 6G | 9G 9C | 9H 9C | 5C 8G 9C | &E 9G |
|  |  |  |  |  | Pre | 0.4 |  |  |  |  |  |  |  |  |  |  |  |  |  |  |
| OCH3 | H | H | CH3 | H | Post | 0.4 | 9C |  | 7C 7G | 7C 8G | 9H 8C 7G | 7G 5G | 5G | &E 7G 7G | 9C &C | 6C 9G 6G | 9G &C | 9G 5C | 9G 5C | &E 3C |
|  |  |  |  |  | Pre | 0.4 |  |  |  |  |  |  |  |  |  |  |  |  |  |  |
| OCH3 | H | H | CH3 | H | Post | 0.4 |  |  | 7C 8G | 7C 8G | 9H 5C 3G | 7G 5G | 5G | &E 7G 7G | 7C 7G | 9G &C | &E | 3G 3G | 4C | &E |
|  |  |  |  |  | Pre | 0.4 |  |  |  |  |  |  |  |  |  |  |  |  |  |  |
| CF3 | H | H | H | H | Post | 0.4 | 9C | 9C | 1U 8G | 7C 8G | 5C 5G 9H | 1C 8G | 1C 8G | 4C &E | 9C 9H | 2C 9H | &C &E | 3C 9C &E | 9C 9C | 2C &E |
|  |  |  |  |  | Pre | 0.4 |  |  |  |  |  |  |  |  |  |  |  |  |  |  |
| OCH3 | H | H | H | H | Post | 0.4 | 9C | 9C | 4U &E | 4U &E | 2C 9H | 2C 9H | 2C 4C 8H | 4C &E | 9C 9H | 5C &E | 8C &E | 5C 9G | 9C 9G | &C &E |
|  |  |  |  |  | Pre | 0.4 |  |  |  |  |  |  |  |  |  |  |  |  |  |  |

TABLE V - H-continued

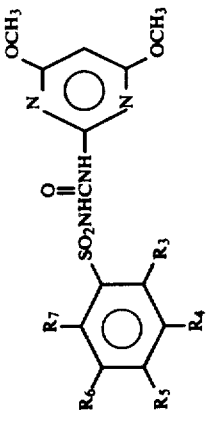

| R₁ | R₄ | R₅ | R₆ | R₇ | Mode of Application | Rate Kg/Ha | BUSH BEAN | COTTON | SORGHUM | CORN | SOY-BEAN | WHEAT | WILD OATS | RICE | BARN-YARD GRASS | CRAB-GRASS | MORN-ING-GLORY | COCK-LE-BUR | CASSIA | NUTS-EDGE |
|---|---|---|---|---|---|---|---|---|---|---|---|---|---|---|---|---|---|---|---|---|
| O(CH₂)₃C-H₃ | H | H | O(CH₂)₃C-H₃ | H | Post | 0.4 | 3S | 3C | 2G | 5H | 0 | 0 | 0 | 2G | 2C | 0 | 1C | 1C | 1C | 0 |
|  |  |  |  |  |  |  | 5G |  |  |  |  |  |  |  |  |  | 4H |  |  |  |
|  |  |  |  |  |  |  | 6Y |  |  |  |  |  |  |  |  |  |  |  |  |  |
| OCH₃ | H | OCH₃ | H | H | Post | 0.4 | 4S | 2C | 6G | 0 | 0 | 0 | 0 | 6G | 0 | 0 | 0 | 2C | 0 | 5G |
|  |  |  |  |  | Post | 0.4 | 7G | 7G | 1C | 9H | 1C | 1C | 5G | 2C | 2C | 5G | 1C |  | 3C | 2C |
|  |  |  |  |  | Pre | 0.4 | 6Y |  | 8G |  |  | 3G |  | 7G | 9G |  |  |  |  |  |
| NO₂ | H | H | H | H | Post | 0.4 | &G | &G | 9G | 2C | 2G | 9G | 8G | &G | 9H | &G | 2C | 5G | 8G | 7C | &E |
|  |  |  |  |  | Pre | 0.4 | 9C | 7C |  | &G |  |  | 5C | &C | 9G | &C | &C | 9C | 8C |  | &C |
|  |  |  |  |  |  |  | 3D |  | 5H | 5U |  |  | 3G | 6C |  |  |  |  |  |  |  |
|  |  |  |  |  | Post | 0.4 | 2C | &G | 9G | &G | 9G | 9G | 8G | &E | 9G | 9G | 9G | 9G | &C | &E | &E |
|  |  |  |  |  | Pre | 0.4 | 9G | 7C | 5C |  | 9G | &G | 8G | &C | 5H | 5H | 2G |  | 8C | &C | &C |
|  |  |  |  |  |  |  | 6Y |  | 1U | 9G |  | 3G |  | 6C | 2G | 8G |  |  |  |  |  |
| CH₃ | CH₃ | H | CH₃ | CH₃ | Post | 0.4 | 2C | 2C | 8G | 4H | 1C | 1C | 0 | 1C | 9H | 2C | 2G | 2C | 2C | 2C | 1C |
|  |  |  |  |  | Pre | 0.4 | 9G | 4H |  | 5H |  | 5H |  | 6G |  | 4G | 6G | 5H | 4G | 4G | 7G |
|  |  |  |  |  |  |  | 6Y | 7G |  |  |  |  |  |  |  |  |  |  |  |  | &C |
|  |  |  |  |  | Post | 0.4 | 9C | 9C | 9C | 9C | 4H | 1C | 1C | 1C | 8H | 1C | 1C | 9G | 7G | 3C | 1C |
|  |  |  |  |  | Pre | 0.4 |  |  | 9H |  | 9H | 9C | 7G | 7G |  | 7G |  |  |  |  | 7G |
|  |  |  |  |  |  |  |  |  |  |  |  | &H |  |  |  |  |  |  |  |  | &C |
| F | H | H | H | F | Post | 0.4 | 2C | 3C | 3C | 7G | 4H | 9C | 9C | 1C | 5C | 9C | 9C | 9C | 9C | 9G | 9G |
|  |  |  |  |  | Pre | 0.4 | 8G | 3H | 9H | &G | 7G | 9H | &H | 7G | &E | 9H | &E | 9G | 8G | 9G | &C |
|  |  |  |  |  |  |  | 6Y | 6G | 7G | 4G |  | 9G | 0 | 0 | 7G | 2G | 2G | 2C |  | 0 | 9G |
| F | F | H | H | Cl | Post | 0.4 | 3C | 3C | 8H | 6G | 2H | 4G | 2G | 9H | 6G | 4G | 9G | 9C | 4G | 4G | 1C |
|  |  |  |  |  | Pre | 0.4 | 8G |  | 3G |  | 5C | 9G |  | 0 | 1C | 0 | 5C | 2C | 4C |  | 7G |
|  |  |  |  |  |  |  | 6Y |  |  |  | 8G |  |  |  |  |  | 8C |  |  |  | &C |
| Cl | H | Cl | H | H | Post | 0.4 | 9C | 9C | 8H | 7G | 3H | 4G | 0 | 6G | 7H | 8G | 9G | 9G | 8H | 9G | 9G |
|  |  |  |  |  | Post | 2.0 |  |  | 2U | &C | 9C | 9C | 2C | 8G | &C | 2C | 2C | 2C | 9C | 9C | 8C |
|  |  |  |  |  |  |  |  |  | 9G |  |  | 5C | 9G | 5C | 1C | 7C | 8C | 9G |  |  | 8C |
| OCH₃ | H | H | Cl | H | Pre | 2.0 |  | 9G | &H |  | 9H |  | 9H | &E | 9H | 2C | 2C | 9G | 9C | 9G | &E |
|  |  |  |  |  | Post | 2.0 | 9C | 1C | 1C | 1H | &C | 5G | 1C | 1C | 2C | 1C | 1C | &C | &C |  | 9G |
|  |  |  |  |  | Pre | 2.0 |  | 5G | 5G | 6G |  |  | 5G | &E | 8H | 5G | &E | &E |  |  | 8C |
| Cl | H | H | Cl | H | Post | 2.0 | 9C | 3H | 2H | 1U |  | 9G | 1C | 1C | &E | 1C | 1C | &E | 9G | 9G | 9G |
|  |  |  |  |  | Pre | 2.0 |  | 5D |  |  |  |  |  |  | 5L |  |  |  |  |  |  |
|  |  |  |  |  |  |  |  | 9G |  |  |  |  |  |  | 1C |  |  |  |  |  | &E |

TABLE V - H-continued

[Structure: sulfonylurea with pyrimidine bearing two OCH₃ groups, connected via SO₂NHCNH to phenyl ring with substituents R₃, R₄, R₅, R₆, R₇]

| R₃ | R₄ | R₅ | R₆ | R₇ | Mode of Application | Rate Kg/Ha | BUSH BEAN | COTTON | SORGHUM | CORN | SOY-BEAN | WHEAT | WILD OATS | RICE | BARN-YARD GRASS | CRAB-GRASS | MORN-ING-GLORY | COCK-LE-BUR | CASSIA | NUTS-EDGE |
|---|---|---|---|---|---|---|---|---|---|---|---|---|---|---|---|---|---|---|---|---|
| CH₃ | H | H | Cl | H | Pre | 2.0 | 9C | 3H | 8G | 9G | 3C | 8G | 7G | | 7H | 7G | 5C | 9C | 5C | 1C |
| | | | | | Post | 0.4 | | 5C | 5G | 1C | 2H | 5G | 0 | 2G | 2H | 1C | 9G | | 9G | 7G |
| | | | | | Post | 0.4 | | 9G | | 5G | 9H | | | | 5G | 5G | | | | |
| F | Cl | H | H | H | Pre | 0.4 | 9G | 2H | 1C | 1C | 2C | 4G | 4G | 9H | 2C | 1G | 4G | 9G | 9G | &E |
| | | | | | Post | 0.4 | | 9G | 4G | 8G | 8G | 2C | 1C | 1C | 7G | 1C | | 2H | 5C | 2C |
| | | | | | | | | | 2H | 3H | 9H | | | | 1C | | | | | |
| Cl | H | H | H | H | Pre | 0.4 | 9C | | 2C | 1C | 2C | 1C | 1C | &E | 4C | 3C | 9G | 9G | 9G | &E |
| | | | | | Post | 0.4 | | 9C | 8G | 9G | 8G | 5G | 6G | 9C | 7G | 2C | | 2H | &C | 9C |
| | | | | | | | | | 5U | &C | 9H | &C | &C | &E | &C | 1C | | | &G | &E |
| | | | | | | | | | 9G | 9G | | 9G | | | 2C | 5G | | | | |
| OC₂H₅ | H | H | OC₂H₅ | H | Pre | 0.4 | 5C | 9C | 2C | 9H | 5C | 1C | 1C | 3C | 9H | 4G | 6C | 8H | 5C | 9G |
| | | | | | Post | 0.4 | 9G | | 9G | | 8G | 5G | 3G | 6G | 2C | | 9G | | 9G | |
| | | | | | Post | 0.4 | 6Y | | | | | | | | 9H | | | | | |
| CH₃ | H | H | CH₃ | H | Pre | 0.4 | 9C | 7C | 7G | 8H | 2C | 2C | 1C | 9H | 2C | 6G | 6C | 8G | 6C | &E |
| | | | | | Post | 0.4 | | 9G | 9G | | 4H | 4G | 3G | 7G | 9H | | 9G | 3H | 9G | 9G |
| | | | | | | | | | | | 2C | 0 | 0 | | 9H | | | 9G | | |
| | | | | | | | | | | | 9H | | | | | | | 8H | | |
| Cl | H | H | H | Cl | Pre | 0.4 | 9C | 9C | 7G | 9G | 9C | 1C | 6G | 1C | 3C | 2C | &E | 9C | 9C | &C |
| | | | | | Post | 0.4 | | | 9G | 2U | 1C | 9G | 8G | &E | 9H | 9G | &E | &E | 4C | &E |
| | | | | | | | | | 7G | 9G | 8G | 1G | 1G | 8G | &C | 2G | 5G | 7G | | 9C |
| | | | | | | | | | | 1C | | | | | 2C | | | 6F | | |
| F | H | Cl | H | H | Pre | 0.4 | 4S | 2H | 8G | 2C | 7G | 2G | 2G | 9H | 3C | 1G | 9G | &E | 9G | &E |
| | | | | | Post | 0.4 | 8G | 5C | 5H | 8H | 2H | 0 | 0 | 0 | 7G | 1C | | 5C | 2C | 9C |
| | | | | | | | 6Y | 9G | | | 9G | | | | 1H | | | 9H | 7G | |
| Cl | H | H | CF₃ | H | Pre | 0.4 | 4S | 2C | 7G | 7G | 7H | 3G | 2G | 8H | 5G | 0 | 9G | 8G | 8G | &E |
| | | | | | Post | 0.4 | 8H | 3H | 6G | 1C | 5C | 2G | 1C | 2C | 2C | 3H | 3C | 9C | 5C | 3C |
| | | | | | | | 6Y | 9G | | 4G | 9G | | | 8G | | | | | 8G | 9G |
| F | H | H | F | | Pre | 0.4 | 3C | 5C | 9H | 1C | 9H | 3G | 0 | &E | 3G | 4G | 9G | 9G | 9G | &E |
| | | | | | Pre | 0.4 | 8G | 9G | | 9G | | | | | | | | | | |
| | | | | | | | 6Y | | | | | | | | | | | | | |

TABLE V - H-continued

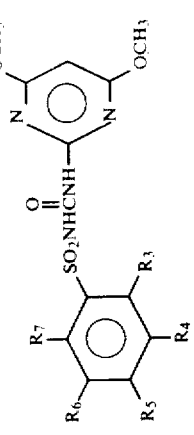

| R₁ | R₄ | R₅ | R₆ | R₇ | Mode of Appli- cation | Rate Kg/Ha | BUSH BEAN | COTTON | SORGHUM | CORN | SOY- BEAN | WHEAT | WILD OATS | RICE | BARN- YARD GRASS | CRAB- GRASS | MORN- ING- GLORY | COCK- LE- BUR | CASSIA | NUTS- EDGE |
|---|---|---|---|---|---|---|---|---|---|---|---|---|---|---|---|---|---|---|---|---|
| H | Cl | H | H | H | Post | 2.0 | 3C 8G 6Y | 2H 4C 9G | 3G | 2G | 2C 9G | 0 | 0 | 6G | 1G | 0 | 6G | 9H | 2C 8G | 8G |
|  |  |  |  |  | Post | 2.0 |  |  |  |  |  |  |  |  |  |  |  |  |  |  |
|  |  |  |  |  | Post | 2.0 |  |  |  |  |  |  |  |  |  |  |  |  |  |  |
|  |  |  |  |  | Pre | 2.0 |  |  |  |  |  |  |  |  |  |  |  |  |  |  |
| Br | H | H | Br | H | Post | 0.4 | 7C 9G | 6C 9G | 1G 5G | 8H 4G | 9H 5H 9H | 0 | 0 | &E 5G | 1H 1C 5H 8H | 0 1H | 9G 9C | 9G &C | 9G 9C | &E 9C |
|  |  |  |  |  | Pre | 0.4 |  |  |  |  |  |  |  |  |  |  |  |  |  |  |
| OCH₃ | H | H | OCH₃ | H | Post | 0.4 | 8D 9G 6Y | 9C | 2H 7G 9G | 1C 9G 5C 9G | 9H | 3G | 3G | 9H | 5H 8H | 4G | 9G | 9G | 9G | &E |
|  |  |  |  |  | Pre | 0.4 |  |  |  |  |  |  |  |  |  |  |  |  |  |  |
| Cl | Cl | H | Cl | Cl | Post | 0.4 | 8C 9G | 9C | 9H 1C 2G 8H | &E 1C 7G 9H | 9C | 2C 8G | 9H 4C | 5C 9G | 9C 4C 9H 9H | 4C 9G | 9G 9C | 9G 9C | 9G 9C | 6C 9G |
|  |  |  |  |  | Pre | 2.0 |  |  |  |  |  |  |  |  |  |  |  |  |  |  |
| H | H | H | CF₃ | H | Post | 2.0 | 5S 9G 6Y | 2H 9G | 5G | 1U | 2C 8G | &E 1C | 9H 4C | &E 3G | 9H 4C 9H 9H | 9G 1C 3H 1C 5G | 9G | &G 9C | 9G 9C | &E 9C |
|  |  |  |  |  | Pre | 2.0 |  |  |  |  |  |  |  |  |  |  |  |  |  |  |
|  |  |  |  |  | Post | 2.0 |  |  |  |  |  |  |  |  |  |  |  |  |  |  |
|  |  |  |  |  | Pre | 2.0 |  |  |  |  |  |  |  |  |  |  |  |  |  |  |
|  |  |  |  |  | Post | 2.0 |  |  | 4H | 5G | 3H 9G | 0 | 3G | 9H | 3G | 1H | 9G | 8G | 8G | &E |
|  |  |  |  |  | Pre | 2.0 |  |  |  |  |  |  |  |  |  |  |  |  |  |  |
|  |  |  |  |  | Pre | 2.0 |  |  |  |  |  |  |  |  |  |  |  |  |  |  |

TABLE V-J
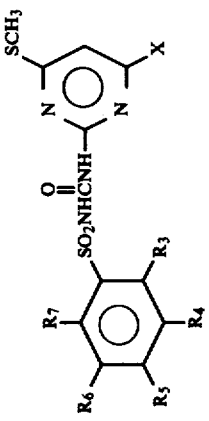
| R3 | R4 | R5 | R6 | R7 | X | Mode of Application | Kg/Ha | BUSH BEAN | COTTON | SORGHUM | CORN | SOYBEAN | WHEAT | WILD OATS | RICE | BARN-YARD GRASS | CRAB-GRASS | MORN-ing GLORY | COCKLE-BUR | CASSIA | NUTS EDGE |
|---|---|---|---|---|---|---|---|---|---|---|---|---|---|---|---|---|---|---|---|---|---|
| H | H | H | H | H | CH3 | Post | 2.0 | 3S 5H 6Y | 1C 5G | 4G | 1C 3G | 2C 2H | 0 | 0 | 6G | 2C | 4G | 1C | 0 | 2C | 7G |
|   |   |   |   |   |     | Post | 2.0 |          |       |    |       |       |   |   |    |    |    |    |   |    |    |
|   |   |   |   |   |     | Post | 2.0 |          |       | 5H | 1C 6H | 2H    | 1C| 1C| &E | 5C | 1C | 6G | 6G | 5G | &E |
|   |   |   |   |   |     | Pre  | 2.0 |          |       |    |       |       |   |   |    |    |    |    |   |    |    |
| H | H | H | H | H | OCH3| Pre  | 2.0 | 2C 3G    | 2C 7G | 5G | 1H 5G | 1C 7G | 0 | 0 | 7G | 2C | 2C | 4G | —  | 2G | 1C 4G |
|   |   |   |   |   |     | Post | 2.0 |          |       |    |       |       |   |   |    |    |    |    |   |    |    |
|   |   |   |   |   |     | Pre  | 2.0 |          |       | 7G | 1C 7G | 2G    | 3G| 2G| &E | 3G | 6G | 7G | 5G | 5G | &E |
|   |   |   |   |   |     | Pre  | 2.0 |          |       |    |       |       |   |   |    |    |    |    |   |    |    |

TABLE V-K

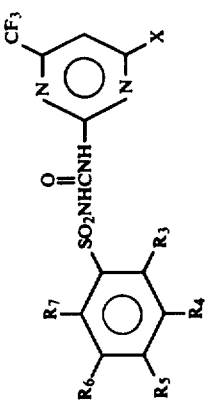

| R1 | R4 | R5 | R6 | R7 | X | Mode of Application | Rate Kg/Ha | BUSH BEAN | COTTON | SORGHUM | CORN | SOYBEAN | WHEAT | WILD OATS | RICE | BARN-YARD-GRASS | CRAB-GRASS | MORN-ING-GLORY | COCKLE-BUR | CASSIA | NUTS EDGE |
|---|---|---|---|---|---|---|---|---|---|---|---|---|---|---|---|---|---|---|---|---|---|
| CH3 | H | H | H | H | CH3 | Post | 2.0 | 3H 9G 6Y | 5C 8G | 3U 9G | 3C 9G | 3H 9G | 2C 7G | 8G | 4C 9G | 1C 9H | 3G | &C | &C | 5C | 9C |
| Cl Post 2.0 | H 5C | H 5C | H | H | CH3 &C | Post | 2.0 | | | 9H | 9H | 9H | 9H | 9G | &E | 2H 9G | 4G | &E | 9G | 9G | &E |
| | | | | | | Pre | 2.0 | | | | | | | | | | 7G | | | | |
| H | H | H | H | H | CH3 | 5C Post | 9C 2.0 | 1C 9G 6Y | 9C 9G | 9C | 2C | 9C 9G | &C | 9C 7G | &C | 2H 9G | 6G 0 | 9G 5C 9G | 9G 5C 9G | 9C 2C 7G | &E 8G |
| H | H | H | H | H | OCH3 | Post | 2.0 | 2C 9G 9D | 2C 3H 9G | 9H 5G | &E 9H | 9H 3H 9G | 9H 3G | 9G 3G | &E 3C 9G | 9H 0 | 0 | 9G | 9G | 9H | &E |
| Cl | H | H | H | H | OCH3 | Post | 2.0 | 3H 8G 6Y | 2C 5H 8G | 8H | 2C 8G | 9H | 8G | 7G | &E | 3G | 0 | 9G | 9G | 9H | 4G |
| | | | | | | Pre | 2.0 | | | 0 | 0 | 7G | 0 | 0 | 4G | 0 | 0 | 2C 9G | 2C 9C | — | 0 9C |
| CH3 | H | H | H | H | OCH3 | Post | 0.4 | 9G &D | 2C 4H 9G | 6G 9G | 5G 1C 9G | 1C 5H 9G | 0 2C 6G | 0 2C 7G | 2G 9G | 0 2C 7G | 6G 1C | 8G 9C | 2C 9C | 0 5C 7G | 0 9C |
| | | | | | | Pre | 0.4 | | | 0 | 0 | 0 | 0 | 0 | 0 | 0 | 0 | | | | |
| H | H | H | H | H | OCH3 | Post | 2.0 | 3S 8G 6Y | 1C | 2H 8G | 9G | 9H | 9G | 9G | &E | 7G | 3G | 9G | 9G | 9C | &E |
| | | | | | | Pre | 2.0 | | | 0 | 0 | 4H | 0 | 0 | 0 | 0 | 0 | 2C 9G | &C | 5C | 0 |
| H | H | CF3 | H | H | CH3 | Post | 2.0 | | 1H 6G | 0 | 0 | 0 | 0 | 0 | 0 | 0 | 0 | 6G &P 9G &C | 4G &P 9G 2C 9G 8G | 0 5G | 0 0 |
| | | | | | | Pre | 2.0 | 1C | | 0 | 0 | 0 | 0 | 0 | 0 | 3C | 0 | | | 0 | 0 |
| H | H | CF3 | H | H | CH3 | Post | 2.0 | 4S 8G 6Y | 2C 9G 5D | 5G | 5G | 1C 7G | 3G | 0 | 8G | 2G | 1C | 7G | 3C 8G | 5C | 8G |
| H | H | H | H | H | CH3 | Post | 2.0 | | | 1H | 7G | 6H | 7G | 4G | &E | | 0 | 8G | &E | 6G | &E |
| | | | | | | Pre | 2.0 | | | | | | | | | | | | | | |

TABLE V - L

| | Mode of Application | Rate Kg/Ha | BUSH BEAN | COTTON | SORGHUM | CORN | SOYBEAN | WHEAT | WILD OATS | RICE | BARN-YARD-GRASS | CRAB-GRASS | MORNING-GLORY | COCKLEBUR | CASSIA | NUTSEDGE |
|---|---|---|---|---|---|---|---|---|---|---|---|---|---|---|---|---|
| By-product of Example 2 | Post | 0.4 | 9C | 9C | 3U | &C | 4H | 1C | 1C | 9C | 1C | 5G | 9C | 9C | 7C | 9C |
| | Post | 0.4 | | | 9G | | 9G | 9G | 9H | | 9H | | | | | |
| | Pre | 0.4 | | | 9H | 9H | 9H | 9H | 9H | &E | 2C | 6G | &E | 9G | 9C | &E |
| | Pre | 0.4 | | | | | | | | | 9G | | | | | |

TABLE V-M

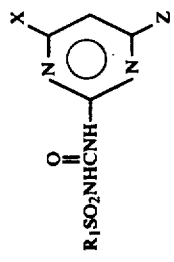

| R₁ | X | Z | Mode of Application | Rate Kg/Ha | BUSH-BEAN | COTTON | SOR-GHUM | CORN | SOYBEAN | WHEAT | WILD OATS | RICE | BARN YARD GRASS | CRAB-GRASS | MORN-ING-GLORY | COCKLE-BUR | CASSIA | NUTS-EDGE |
|---|---|---|---|---|---|---|---|---|---|---|---|---|---|---|---|---|---|---|
| naphthyl | Cl | CH₃ | Post | 2.0 | 1C 4H | 1H | 0 | 0 | 1H | 0 | 0 | 0 | 0 | 0 | 0 | 2G | 0 | 0 |
| chlorothienyl | | | Post | 2.0 | 3S 5G 6Y | 3C 5G | 1C 3G | 1C 3G | 2H | 0 | 0 | 9H | 2G | 0 | 2G | &E | 5G | 2G |
| naphthyl | H | CH₃ | Pre | 2.0 | | | 2G | 2G | 1C 1H | 2G | 0 | 0 | 0 | 0 | 1H | &P 7G | 2G | 1C 4G |
| thienyl | | | Pre | 2.0 | | | | | | | | | | | | | | |
| naphthyl | CH₃O— | CH₃O— | Post | 0.4 | 6C 9G | 3C 3H 9G | 1C 4G | 1C 4G | 6H 9G | 1C | 1C | 2C 7G | 1C 8H | 1C | 8G | 8G | 2G | 4C 9G |
| | | | Post | 0.4 | | | 5G | 9H | | | | 1C 5G | 9H | | 7G | &H | 1C 9G | 1C 9G |
| naphthyl | CH₃O— | CH₃ | Post | 0.4 | 8C | 6C 9G | 2H 8G | 1C 9G | 9H | 3G | 2G | 9H | 9H | 5C 7G 2C 9G | 9G | 9G | 9C | 9C |
| thienyl | | | Pre | 2.0 | | | &c 9G | &C &E | 5C 8G 9G | 1C 7G &E | 8C 3C 8G | 6C 8G &E | &C 9G | | &C &E | 9C 9C | 9C 9G | 9C &E |
| naphthyl | CH₃— | CH₃ | Post | 0.4 | 3C 3H 9G | 3H 5G 9G | 3H 9G | 5H 9G | 5H 9G | 1C 5G | 5G | 7G | 9H | 4G | 1C 6G | 9H | 2C 8G | 4C 9C |
| thienyl | | | Post | 0.4 | | | 1C 9G | 8H | 9G | 8G | 8G | 9H | 3C | 5G | 9G | 9G | 9C | 9C |
| dichlorothienyl | CH₃ | CH₃O— | Post | 0.4 | 4S 7G 6Y | 6C 9G | 7G | 3H 7G | 2C 8G | 2G | 0 | 2G | 7H | 0 | 9G | 2H 9G | 3C | 8G |
| dichlorothienyl | CH₃O— | CH₃O— | Post | 0.4 | 2H 5G | 6C 9G | 8H | 9H | 9H | 9G | 7G | 9H | 7H | 7H | 9G | 9G | 9G | 9C &E |
| dichlorothienyl | | | Post | 0.4 | 5C 8D 9G | 7C 9G | 2G 6G | 5G 8G | 2H 7G 9H | 5G | 0 | 0 | 1C | 0 | 1C 5H 8G | 5C 9G | 3C 6G 8G | 9C &E |
| thienyl | | | Pre | 0.4 | | | 9H | 5U 9G | 9H | 5G | 0 | 5H | 6H | &E | 3C 9G | 9G | 7G | 8G |
| | | | Pre | 0.4 | | | | | | 1C 8G | 1C 8G | 5C 9G &E | 3C 9G | 4G 1C 7G | 9G | 1C 9G | 5C 9G | 5C 9G &E |

TABLE V-M-continued $R_1SO_2NHCNH-$ (with pyrimidine bearing X and Z substituents, C=O linkage)

| R₁ | X | Z | Mode of Application | Rate Kg/Ha | BUSH-BEAN | COTTON | SOR-GHUM | CORN | SOYBEAN | WHEAT | WILD OATS | RICE | BARN-YARD-GRASS | CRAB-GRASS | MORN-ING-GLORY | COCKLE-BUR | CASSIA | NUTS-EDGE |
|---|---|---|---|---|---|---|---|---|---|---|---|---|---|---|---|---|---|---|
| 3-methyl-5-Cl-thiophene | CH₃ | CH₃O— | Post | 2.0 | 3C 7G 6Y | 5C 8G | 1C 7G | 9G | &C | 1C 6G | 1C 6G | 7C | 9C | 2C 5G | 5C | Pc | 2C 5G | 2C 7G |
| 5-Cl-thiophene | CH₃ | CH₃ | Post | 2.0 | | | 2C 8G | 9G | 9H | 9G | 7G | &E | 2C 8G | 3G | 9G | 9G | &E | &E |
| 5-Cl-thiophene | CH₃ | CH₃ | Post | 2.0 | 5S 6G 6Y | 2C 2H 8G | 1C 5G | 1H 4G | 1C 5G | 0 | 0 | 8G | 4G | 4G | 2G | 5C 8G | 1C | 1C 8G |
| 3-methylthiophene | CH₃ | CH₃ | Pre | 2.0 | | | 1C 7G | &E | 3G | 7G | 1C 5G | &E | 2C 6G | 2C 8G | 7G | 8G | 9G | &E |
| 3-methyl-5-Cl-thiophene | CH₃ | CH₃ | Post | 2.0 | 5C 9G 6Y | 2U 4H 9G | 3U 9G | 9C | 2C 8G | 5C 9G | 8G | 7C 8G | 2C 9G 9C | 2C 8G | 8G | 2C 8G | &P 9G | 8G |
| 2-Cl-furan | CH₃ | CH₃ | Pre | 2.0 | | | 1C 9G 5G | 4G | 3G | 2G | 2C 7G 0 | &E | 3C 9H 2G | 9G | 9G | 9C | 2G | 8G 2G |
| naphthyl | CH₃ | CH₃ | Post | 0.4 | 3G | 4H 5C 8G | 5G | 6G | 3H | 5G | 3G | 3G | 4G | 3G | 8G | 8G | 7G | 6E |
| naphthyl | CH₃ | CH₃ | Pre | 0.4 | | | 3U 9G | 9C | 9C | 1C 8G 5X 9H | 2C 8G | 6C 9G | 6C 9H | 2C 9G | &C | 9C | 6C 9G | 0 |
| naphthyl | H | CH₃O | Post | 2.0 | 5C 9G 6Y | 6C 9G | &E | &E | 9H | 2G | 2C 8G | &E | 9H | 9G | &E | 9G | 9G | &E |
| naphthyl | H | CH₃O | Pre | 2.0 | | 1B | 3G | 1C 6G | 6H | 0 | 0 | 3G | 0 | 0 | &P 8G | 9H | 0 | 1C 7G |
| naphthyl | CH₃ | CH₃ | Post | 0.4 | 2H 7G 6Y | | 6G | 7G | 5H | 2B | 0 | 9H | 2G | 0 | 9G | 9G | 9G | 2C 9G 5G |
| naphthyl | CH₃ | CH₃ | Pre | 0.4 | 3H 8G 6Y | 3C 3H 9G | 8G | 2C 7G | 2H 9G | 1C 3G | 2C | 6G | 2C | 1C | 1B 8G | 9H | 1C 5G | |
| naphthyl | CH₃ | CH₃ | Post | 0.4 | | | 5G | 6G | 0 | 0 | 0 | 9H | 0 | 0 | 5G | &E | 7G | 0 |

TABLE V-N
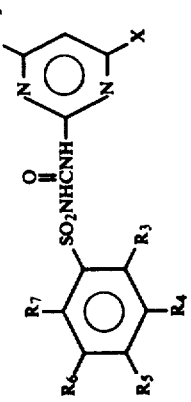
| R3 | R4 | R5 | R6 | R7 | X | Mode of Application | Rate Kg/Ha | BUSH BEAN | COTTON | SORGHUM | CORN | SOYBEAN | WHEAT | WILD OATS | RICE | BARN YARD GRASS | CRAB GRASS | MORN-ING GLORY | COCKLE-BUR | CASSIA | NUT SEDGE |
|---|---|---|---|---|---|---|---|---|---|---|---|---|---|---|---|---|---|---|---|---|---|
| H | H | H | H | H | CH3 | Post | 2.0 | 2H | 2C | 8G | 2C | 2C | 4G | 7G | 2G | 9H | 6G | 4G | 2C | 1C | 7G |
|  |  |  |  |  |  | Post | 2.0 | 8G | 2H | 5I | 2H |  |  |  | 8G |  |  |  | 2G | 5G |  |
|  |  |  |  |  |  | Post | 2.0 | 6Y | 7G |  | 6G | 7G | 9G | 7G | 8E | 1C | 5G | 6G | — | 5G | 9G |
|  |  |  |  |  |  | Pre | 2.0 |  |  | 1C | 9G |  |  |  |  | 8G |  |  |  |  |  |
|  |  |  |  |  |  | Pre | 2.0 |  |  | 8G |  |  |  |  |  |  |  |  |  |  |  |
| H | H | H | H | H | H | Post | 2.0 | 2S | 2C | 5G | 2G | 1C | 0 | 0 | 6G | 2G | 2G | 2C | 1C | 3C | 1C |
|  |  |  |  |  |  | Post | 2.0 | 3H | 2H |  |  |  |  |  |  |  |  | 6G |  |  | 5G |
|  |  |  |  |  |  | Pre | 2.0 | 6Y | 4G | 6G | 1C | 1C | 4G | 4G | 8E | 5G | 0 | 7G | — | 7G | 5G |
|  |  |  |  |  |  | Pre | 2.0 |  |  |  | 6G |  |  |  |  |  |  |  |  |  |  |

TABLE V-O

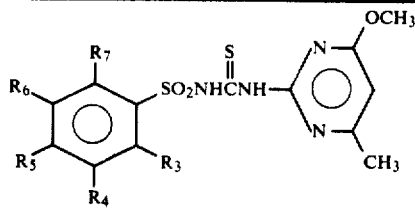

| $R_3$ | $R_4$ | $R_5$ | $R_6$ | $R_7$ | Mode of Application | Rate Kg/Ha | Bush Bean | Cotton | Sorghum | Corn | Soybean | Wheat | Wild Oats | Rice | Barnyardgrass | Crabgrass | Morningglory | Cocklebur | Cassia | Nutsedge |
|---|---|---|---|---|---|---|---|---|---|---|---|---|---|---|---|---|---|---|---|---|
| H | H | H | H | H | Post | 0.4 | 4C | 5C | 1C | 8G | 2C | 1G | 7G | 8C | 9H | 4G | 3C | 1C | 3C | 7G |
|   |   |   |   |   | Post | 0.4 | 9G | 8G | 9G |    | 8G |    |    |    |    |    |    | 5G | 7G |    |
|   |   |   |   |   | Post | 0.4 | 6Y |    |    |    |    |    |    |    |    |    |    |    |    |    |
|   |   |   |   |   | Pre | 0.4 |    |    | 9H | 9G | 9H | 9G | 1C | &E | 2C | 1C | 9G | 9G | &E | 9G |
|   |   |   |   |   | Pre | 0.4 |    |    |    |    |    |    | 8G |    | 8G | 5G |    |    |    |    |

TABLE V - P

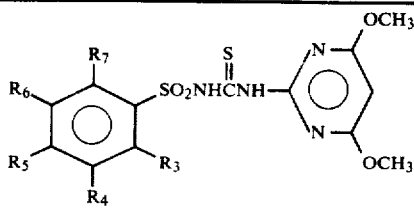

| $R_3$ | $R_4$ | $R_5$ | $R_6$ | $R_7$ | Mode of Application | Rate Kg/Ha | Bush Bean | Cotton | Sorghum | Corn | Soybean | Wheat | Wild Oats | Rice | Barnyardgrass | Crabgrass | Morningglory | Cocklebur | Cassia | Nutsedge |
|---|---|---|---|---|---|---|---|---|---|---|---|---|---|---|---|---|---|---|---|---|
| H | H | H | H | H | Post | 0.4 | 4C | 2C | 1C | 5H | 4C | 0 | 1C | 3C | 2C | 2C | 9C | 8G | 5C | 5C |
|   |   |   |   |   | Post | 0.4 | 8G | 3H | 8G |    | 8G |   |    | 8G | 5G |    |    |    |    | 9G |
|   |   |   |   |   | Post | 0.4 | 6Y | 9G |    |    |    |   |    |    |    |    |    |    |    |    |
|   |   |   |   |   | Pre | 0.4 |    |    | 9H | 2U | 1C | 4G | 5G | &E | 2C | 2C | 9G | &E | 9G | &E |
|   |   |   |   |   | Pre | 0.4 |    |    |    | 9G | 6H |    |    |    | 6G | 8G |    |    |    |    |

The following three tests illustrate the utility of compounds of this invention for the control of weeds in wheat.

A. Twenty-five cm diameter plastic pots filled with Fallsington silt loam were planted to soybean, cotton, alfalfa, corn, rice, wheat, sorghum, velvetleaf (*Abutilon theophrasti*), sesbania (*Sesbania exaltata*), Cassia (*Cassia tora*), morningglory (*Ipomoea sp.*), jimsonweed (*Datura stramonium*), cocklebur (*Xanthium pennsylvanicum*), crabgrass (*Digitaria sp.*), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were sprayed overall with the test chemicals dissolved in a nonphytotoxic solvent. Fourteen days after treatment, all species were compared to untreated controls and visually rated for response to treatment. The data are presented in Table VI.

TABLE VI

OVER-THE-TOP SOIL/FOLIAGE TREATMENT

| Structure | Rate, kg/ha | Soy-beans | Vel-vet-leaf | Ses-ban-ia | Cas-sia | Cot-ton | Morn-ing-glo-ry | Al-fal-fa | Jim-son-weed | Cock-le-bur | Corn | Crab-grass | Rice | Nut-sedge | Barn-yard-grass | Wheat | Gi-ant Fox-tail | Wild Oats | Sor-ghum |
|---|---|---|---|---|---|---|---|---|---|---|---|---|---|---|---|---|---|---|---|
| ![structure 1: 2-Cl phenyl] | 0.06 | 10G 8C | 10G 9C | 10G 9C | 10G 6C | 10G 8C | 8G 2C | 10G 2C | 10G 5C | 10G 5C | 9G 8C | 0 | 3G 2C | 5G 5C | 5G 2C | 2G | 5G 5C | | 5G 3C |
| | 0.12 | 10G 9C | 10G 9C | 10G 9C | 10G 7C | 10G 5C | 10G 7C | 10G 4C | 10G 6C | 10G 6C | 9G 9C | 4G | 2G 2C | 8G 8C | 5G 3C | 4G | 5G 3C | 3G | 3C 9G |
| | 0.50 | 10G 9C | 10G 9C | 10G 9C | 10G 9C | 10G 9C | 10G 8C | 10G 6C | 10G 6C | 10G 9C | 9G 8C | 2G | 2C 3C | 9G 9C | 7G 3C | 8G | 5G 5C | 7G | 9G 3C |
| ![structure 2: 4-Br, 2-CH3] | 0.06 | 10G 8B | 10C | 10G 9C | 10G 6C | 10G 8C | 10G 9C | 3G 2C | 7G 2C | 10G 9C | 0 | 0 | 4G | 5G 10C | 8G | 4C | 0 4G | 0 | 3G |
| | 0.25 | 10G 9B | — | 9C | 10G 9C | 10G 9C | 10G 9C | 8G 2C | 7G 3C | 10G 9C | 6G | 3G | 4G | 5C | 10G | 2G | | 0 | 8G |
| ![structure 3: 2,5-(OCH3)] | 0.06 | 10G 6C | 10G 8C | 10G 7B | 10G 7C | 10G 6C | 10G 7C | 10G 9C | 5G | 10G 6C | 7G 3C | 0 | 5G | 10G 5C | 10G 5H | 4G | 6G | 7G | 8G |
| | 0.25 | 10G 7C | 10G 8B | 10B 9C | 10G 8C | 10G 9C | 10G 6C | 10G 9C | 9G | 10G 9C | 10G 6C | 5G | — | 10G 3C | 10G 5H | 5G | 10G | 10G | 8G |
| ![structure 4: 2,5-Cl2] | 0.12 | 10G 5B | 10G 7B | 10G 7C | 8G 5B | 4G 3B | 8G 2B | 3G 2B | 5G 2B | 10B | 2C | 0 | 0 | 6G 5C | 3G 2C | 2C | 3C | 3C | 7G 3C |
| | 0.50 | 10G 5B | 10G 8B | 10G 7C | 10G 5B | 10G 7B | 8G 4B | 10G 6B | 10G 7B | 10B | 7G 5H | 5G 2H | 5G 3C | 6G 5C | 8G 3B | 3G | 3C | 5G 3C | 10G 7H |
| ![structure 5: 2,3,5-Cl3] | 0.06 | 10G 4B | 10G 5C | 10G 7C | 3G 6G | 6G 8C | 3G 5G | 5G 7G | 6G 8G | — | 5G 2H | 0 | 0 | 6G 5G | 6G 2H | 0 | 0 7G | 0 | 7G 5G |
| | 0.25 | 10G 5B | 10G 8C | 10G 7C | 7G 5C | 8G 3C | 5G 5G | 7G 3C | 8G 2C | — | 5G 2H | 0 | 3C | 5G | 6G 2H | 3G | 7G 2C | 3G | 2H |

TABLE VI-continued
OVER-THE-TOP SOIL/FOLIAGE TREATMENT

| Structure | Rate, kg/ha | Soy- beans | Vel- vet- leaf | Ses- ban- ia | Cas- sia | Cot- ton | Morn- ing- glo- ry | Al- fal- fa | Jim- son- weed | Cock- le- bur | Corn | Crab- grass | Rice | Nut- sedge | Barn- yard- grass | Wheat | Giant Fox- tail | Wild Oats | Sor- ghum |
|---|---|---|---|---|---|---|---|---|---|---|---|---|---|---|---|---|---|---|---|
| Structure 1 | 0.06 | 10G 4C | — | 10G 2C | 8G 4H | 10G 5C | 5G 10G | 10G 10G | 10G 4C | 6G | 3G | 0 | 0 | 0 | 4G | 0 | 0 | 0 | 6G |
|  | 0.25 | 10G 6C | — | 10G 8C | 10G 7C | 10G 8C | 10G 4C | 10G 2C | 10G | — | 5G | 0 | 2G | 3G | 6G | 2G | 0 | 0 | 8G |
| Structure 2 | 0.12 | 10G 7H | 8G 5H | 10B 6H | 10G 4H | 6G 5H | 6G 3H | 5G 3H | 8G 6H | 0 | 7G 5H | 0 4G 3H | 4H | 3G 7G 5H | 10G 7H 8G 6H | 0 | 0 2G | 10G 3H 8G 5H | 7G 5H 8G 7H |
|  | 0.50 | 10G 10C | 10G 7H | 8G 7H | 10G 7H | 10G 5H | 10G 7H | 10G 7H | 10G 6H | — | 8G 5H | | 3H | | | 4G | | | |
| Structure 3 | 1/16 | 10G 7B | 10C | 10C | 10G 5C | 10G 4C | 10G 8C | 5G | 2C 8G 10G 6C | 10G 7C 10G 9C | 3G 5G 3G | 0 | 0 | 6C 10G 10G 7C | 0 8G 3C | 0 | 0 | 0 | 3G |
|  | 1/4 | 10G 10C | 10C | 10C | 5C 10G 7C | 4C 10G 6C | 8C 10G 9C | 8G 10G 5C | | | | | | | | | 2G | | 3G |
| Structure 4 | 1/16 | 10G 3C | 4G 2C | 10G 3C | 4G 5G 2C | 4G 6G 3C | 4G 2C 10G 5C | 7G 5G 2C | 5G 2C 7G 2C | — 4G 2C | 0 5G 4G | 0 4G 2C | 0 | 5G 5G 2C | 8G 5G 7G 5H | 0 0 | 0 3G | 0 0 | 7G 10G 2C |
|  | 1/8 | 10G 4C | 6G 3C | 10G 3C | 6G 2C | 6G 3C | 10G 5C | 7G 5C | 7G 5C | — | 6G 2C | 6G 2C | 4G | 8G 2C | 9G 3C | 7G | 8G | 2G | 6G 3C |
|  | 1/2 | | 10G 8C | 10G 8C | | 10G 5C | | | | | | | | | | | | | |

Structure 1:
2,4,6-trimethylphenyl-SO₂—NH—C(=O)—NH—(4-methoxy-6-methylpyrimidin-2-yl)

Structure 2:
4-chloro-2-methoxyphenyl-SO₂—NH—C(=O)—NH—(4-methoxy-6-methylpyrimidin-2-yl)

Structure 3:
2,4-dibromophenyl-SO₂NHC(=O)NH-(4,6-dimethoxypyrimidin-2-yl)

Structure 4:
2-chlorophenyl-SO₂NHC(=O)NH-(4,6-dimethoxypyrimidin-2-yl)

B. The compounds were applied in a non-phytotoxic solvent as overall sprays on postemergence plantings of wheat (11 cm tall, 2 leaf stage), wild oats (*Avena fatua*) (9 cm tall, 1 leaf stage), *Bromus tectorum* (5 cm tall, 1 leaf stage), *B. secalinus* (5 cm tall, 1 leaf stage), blackgrass (*Alopecurus myosuroides*) (3 cm tall, 1 leaf stage), and annual ryegrass, (*Lolium multiflorum*) (8 cm tall, 1 leaf stage) and also on preemergence plantings of the same species. All plantings were in 25 cm diameter soil pans. The tests were maintained in a greenhouse and plant response ratings were taken 5 weeks after application. The results of these tests are shown in Table VII.

kochia (*Kochia scoparia*) 5 cm tall, wild chamomile (*Matricaria inodora*) 3 cm tall, wild mustard (*Brassica arvensis*) 7 cm tall, dog fennel (*Eupatorium capillifolium*) 3 cm tall, and wild buckwheat (*Polygonum convolvulus*) 6 cm tall and to preemergence plantings of the same species, all planted in soil pots. The tests were maintained in a greenhouse and plant response ratings were taken four weeks after application, as shown in Table VIII for

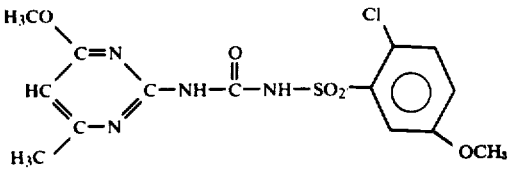

TABLE VII

| Structure | Rate, kg ai/ha | Preemergence | | | | | |
|---|---|---|---|---|---|---|---|
| | | Wheat | Wild Oats | Bromus tectorum | Bromus secalinus | Blackgrass | Annual Ryegrass |
| (H₃CO/HC/C=N pyrimidine)—NH—C(O)—NH—SO₂—Ph—CF₃ | 1/32 | 0 | 0 | 0 | 0 | 0 | 0 |
| | 1/16 | 0 | 0 | 0 | 0 | 0 | 0 |
| | 1/8 | 0 | 0 | 0 | 3G | 1G | 1G |
| (O—CH₃/Cl—Ph)—SO₂—NH—C(O)—NH—C(pyrimidine, O—CH₃, CH₃) | 1/32 | 2G | 4G | 8G | &C | 9C | 9C |
| | 1/16 | 2G | 5G | 9G | &C | &C | &C |
| | 1/8 | 8G | 9C | &C | &C | &C | &C |
| (CF₃/HC/H₃C pyrimidine)—NH—C(O)—NH—SO₂—Ph | 1/32 | 0 | 0 | 0 | 0 | 0 | 0 |
| | 1/16 | 0 | 0 | 0 | 0 | 0 | 0 |
| | 1/8 | — | 0 | 0 | 5C | 4C | 2C |
| (O—CH₃/Cl—Ph)—SO₂—NH—C(O)—NH—C(pyrimidine, O—CH₃, CH₃) | 1/32 | 1G | 4G | 7G | 9G | 9G6C | 9G5C |
| | 1/16 | 1G | 5G | 8G | 10C | 10C | 9C |
| | 1/8 | 1G | 7G | 9G | 10C | 9C | 9C |
| (H₃CO/HC/H₃CO pyrimidine)—NH—C(O)—NH—SO₂—Ph—CF₃ | 1/32 | 0 | 0 | 0 | 0 | 0 | 0 |
| | 1/16 | 0 | 0 | 0 | 0 | 0 | 0 |
| | 1/8 | 1G | 0 | 0 | 3G | 5G | 3C |

C. The compound was applied in a nonphytotoxic solvent as an overall spray to established (postemergence) plantings of wheat 22 cm tall, wild oats (*Avena fatua*) 14 cm tall, downy brome (*Bromus tectorum*) 3 cm tall, cheat (*Bromus secalinus*) 5 cm tall, barley 22 cm tall,

TABLE VIII

| Rate, kg ai/ha | Preemergence | | | | | | | | | |
|---|---|---|---|---|---|---|---|---|---|---|
| | Wheat | Wild Oats | Bromus tectorum | Bromus secalinus | Barley | Kochia | Matricaria | Wild Mustard | Dog Fennel | Wild Buckwheat |
| 1/16 | 2C | 3G | 4G | 6G | 2C | 9C | &C | &C | &C | 5G |
| 1/8 | 3C | 7G | — | 8G | 2C | &C | &C | &C | &C | 8G |
| 1/4 | 3C | 7G | 5G | 8G | 4G2C | &C | &C | &C | &C | 9G |
| 1/2 | 4C | 7G | 8G | 8G | 5G5X2C | &C | &C | &C | &C | 8G |

TABLE VIII-continued

| Rate, kg ai/ha | Postemergence | | | | | | | | | |
|---|---|---|---|---|---|---|---|---|---|---|
| | Wheat | Wild Oats | Bromus tectorum | Bromus secalinus | Barley | Kochia | Matricaria | Wild Mustard | Dog Fennel | Wild Buckwheat |
| 1/16 | 0 | 2G | 7G | 7G | — | &C | &C | &C | &C | &C |
| 1/8 | 0 | 2G | 7G | 7G | 2G | &C | &C | &C | &C | 7C |
| 1/4 | 0 | 3G | 7G | 7G | 2G5C | 9C | &C | &C | &C | &C |
| 1/2 | 3G | 8G | &C | 9C | 4G5C | &C | &C | &C | &C | &C |

The following data show the value of the compounds of this invention for the control of nutsedge.

Nutsedge (*Cyperus rotundus*) tubers (5 per pot) were planted approximately 2.5 cm deep in 10 cm pots containing Fallsington silt loam. Each compound to be evaluated was applied as a preemergence soil surface spray, a directed tuber spray, soil incorporated throughout the top 2.5 cm of soil and sprayed postemergence on the foliage of plants approximately 8–10 cm tall. The compounds were dissolved in a suitable solvent and applied at a spray volume of 560 l/ha. The effects of chemical treatment on plant growth were visually evaluated four weeks after treatment as shown in Table IX.

It was observed in yet another test that compounds of this invention have utility for the selective control of nutsedge in crops.

Several plastic pans 25 cm in diameter and lined with polyethylene liners were filled with Fallsington silt loam soil and seeds of the following plants planted 2.5 cm deep in each pan: corn (*Zea mays*), soybean (*Glycine max*), rice (*Oryza sativa*), cotton (*Gossypium hirsutum*) and nutsedge tubers (*Cyperus rotundus*). Each compound to be evaluated was dissolved in a suitable solvent and applied pre- and postemergence at a spray volume of 560 l/ha. The plants treated postemergence ranged in height from 6–14 cm at the time of treatment. Four weeks after treatment, the effects of chemical treatment on plant growth were visually rated, as shown in Table X.

TABLE IX

| Structure | Rate, kg/ha | Plant Response 4 Weeks after Treatment | | | |
|---|---|---|---|---|---|
| | | Pre surface spray | Pre tuber + soil spray | Pre soil inc. 2.5 cm. | Post foliar spray |
| 2,6-F₂-C₆H₃-SO₂-NH-C(O)-NH-(4-OCH₃-6-CH₃-pyrimidin-2-yl) | 1/64 | 5E,7G | &E | &E | 5C,7G |
| | 1/32 | &E | &E | 9E,9G | &C |
| | 1/16 | &E | &E | &E | &C |
| | 1/8 | &E | &E | &E | &C |
| | 1/4 | &E | &E | &E | &C |
| 2,6-Cl₂-C₆H₃-SO₂-NH-C(O)-NH-(4,6-(CH₃)₂-pyrimidin-2-yl) | 1/32 | 5G | 7E,7G | 8E,9G | &C |
| | 1/16 | 5G | 7E,8G | 9E,9G | 9C |
| | 1/8 | 8E,8G | &E | 9E,9G | &C |
| | 1/4 | 5E,6G | &E | &E | &C |
| 2,6-Cl₂-C₆H₃-SO₂-NH-C(O)-NH-(4-OCH₃-6-CH₃-pyrimidin-2-yl) | 1/8 | &C | &E | &E | &C |
| | 1/4 | &E | &E | &E | &C |
| 2,6-F₂-C₆H₃-SO₂-NH-C(O)-NH-(4,6-(CH₃)₂-pyrimidin-2-yl) | 1/32 | 0 | 0 | 0 | 0 |
| | 1/16 | 3G | 6G | 7G | 3C,3G |
| | 1/8 | 9E,8G | 8G | 8G | 9C |

TABLE X

| Structure | Rate, kg/ha | Pre-emergence | | | | | Post-emergence | | | |
|---|---|---|---|---|---|---|---|---|---|---|
| | | Corn | Cotton | Soybean | Rice | Nutsedge | Corn | Cotton | Soybean | Rice | Nutsedge |
| [2-CH₃-C₆H₄-SO₂-NH-C(O)-NH-(4-CH₃,6-CF₃-pyrimidin-2-yl)] | 0.06<br>0.12 | 2C<br>4C,3G | 0<br>0 | 0<br>1G | 5G<br>7G | 9G<br>&E | 0<br>2G | 0<br>3C,5G | 2H<br>7H,3G | 1G<br>3C,4G | 0<br>6G |
| [2-Cl-C₆H₄-SO₂-NH-C(O)-NH-(4-CH₃,6-CF₃-pyrimidin-2-yl)] | 0.06<br>0.12 | 5U,7G<br>7U,9G | 1G<br>2G | 1G<br>5H,3G | 7H,8G<br>8H,8G | &E<br>&E | 7H,6G<br>7H,7G | &C<br>&C | 4H,5G<br>7H,7G | 3C,5G<br>5C,7G | 5C,7G<br>&C |
| [2,6-Cl₂-C₆H₃-SO₂-NH-C(O)-NH-(4-CH₃,6-CH₃-pyrimidin-2-yl)] | 0.03<br>0.06 | 8C,8G<br>9C,8G | 1G<br>3G | 8H,7G<br>8H,8G | 8H,8G<br>&H | &E<br>&E | 7C,8G<br>8C,8G | &C<br>&C | &C<br>&C | 7C,8G<br>8C,8G | 6G<br>5C,7G |
| [2,6-Cl₂-C₆H₃-SO₂-NH-C(O)-NH-(4-CH₃,6-H-pyrimidin-2-yl)] | 0.03<br>0.06 | 0<br>1G | 0<br>1G | 0<br>1G | 0<br>3G | 0<br>&E | 0<br>0 | 0<br>5H,4G | 4H,4G<br>5H,5G | 0<br>1G | 1<br>4G |
| [2-F,5-CH₃-C₆H₃-SO₂-NH-C(O)-NH-(4-CH₃,6-OCH₃-pyrimidin-2-yl)] | 0.03<br>0.06 | 7H,7G<br>7H,8G | 0<br>1G | 6H,3G<br>8H,7G | 2H,5G<br>5H,7G | 8G<br>9G | 3G<br>5H,7G | 5H,7G<br>&C | &C<br>&C | 2C,3G<br>3C,3G | 1G<br>6G |
| [2,5-F₂-C₆H₃-SO₂-NH-C(O)-NH-(4-OCH₃,6-OCH₃-pyrimidin-2-yl)] | 0.03<br>0.06 | 1G<br>2G | 1G<br>2G | — | 3G<br>5G | &E<br>&E | 1G<br>2G | 5H,6G<br>7H,7G | &C<br>&C | 1G<br>1G | 8G<br>8G |

TABLE X-continued

| Structure | Rate, kg/ha | Pre-emergence ||||| Post-emergence ||||
|---|---|---|---|---|---|---|---|---|---|---|
| | | Corn | Cotton | Soybean | Rice | Nutsedge | Corn | Cotton | Soybean | Rice | Nutsedge |
| 2-Br-5-F-C₆H₃-SO₂-NH-C(=O)-NH-(4,6-dimethoxypyrimidin-2-yl) | 0.03 | 0 | 0 | 0 | 0 | 2G | 0 | &C | &C | 0 | 7G |
| | 0.06 | 1G | 1G | 0 | 0 | &E | 0 | &C | &C | 0 | 8G |
| 2,5-Cl₂-C₆H₃-SO₂-NH-C(=O)-NH-(4,6-dimethoxypyrimidin-2-yl) | 0.015 | 2G | 0 | 0 | 1G | 9G | 2G | 2H,5G | &C | 0 | 4C,8G |
| | 0.03 | 2G | 0 | 0 | 1G | &E | 2G | 7H,7G | &C | 0 | &C |
| | 0.06 | 2G | 1H | 1G | 2G | &E | 2G | 8H,8G | &C | 1C | &C |
| | 0.12 | 5H,6G | 1H,1G | 8H,8G | 5G | &E | 2G | &C | &C | 2G | &C |
| | 0.25 | 7H,6G | 1H,1G | 8H,8G | 5H,7G | &E | 5H,6G | &C | &C | 2C,2G | &C |
| | 0.5 | 8H,8G | 2H,3G | 9H,9G | 7H,8G | &E | 6H,6G | &C | &C | 2C,3G | &C |
| 2-CH₃-5-Cl-C₆H₃-SO₂-NH-C(=O)-NH-(4,6-dimethoxypyrimidin-2-yl) | 0.25 | 1G | 0 | 2H,2G | 4G | 8E,9G | 0 | 9C,8G | &C | 0 | 3C,7G |
| | 0.5 | 2G | 2G | 7H,6G | 5H,6G | 9E,9G | 0 | 9C,9G | &C | 0 | 4C,7G |
| | 1 | 7G | 2G | 9H,8G | 7H,7G | &E | 2G | 9C,9G | &C | 0 | 4C,7G |
| | 2 | 7H,8G | 2H,7G | 9H,9G | 7H,7G | &E | 1G | &C | &C | 1G | 4C,8G |
| | 4 | 7H,9G | 2H,7G | 9H,9G | 8H,8G | &E | 1G | &C | &C | 1G | 5C,8G |
| 2-F-3-Cl-C₆H₃-SO₂-NH-C(=O)-NH-(4,6-dimethoxypyrimidin-2-yl) | 0.015 | 0 | 0 | 0 | 2G | 2G | 1G | 9C,8G | 9C,8G | 0 | 2C,7G |
| | 0.03 | 1G | 1G | 1G | 4G | 9E,9G | 1G | 9C,9G | &C | 3G | 5C,7G |
| | 0.06 | 3G | 1G | 1G | 6G | &E | 1G | &C | &C | 2G | 5C,7G |
| | 0.12 | 3G | 3G | 5H,6G | 5H,7G | &E | 1G | &C | &C | 3G | 7C,8G |
| | 0.25 | 5H,7G | 3G | 7H,8G | 7H,8G | &E | 2G | &C | &C | | 7C,8G |
| 2-thienyl-SO₂-NH-C(=O)-NH-(4,6-dimethoxypyrimidin-2-yl) | 0.06 | 3G | 3C,5G | 4C,6G | 3C,5G | 5G | 1G | 8C,7G | 9C,9G | 2C | 8G |
| | 0.12 | 4H,5G | 5H,6G | 7H,8G | 8C | 9G | 5H,7G | 9C,9G | &C | &C | 8G |

As noted in the following tests, the compounds of this invention are useful for the control of certain aquatic weeds.

The compounds were applied in a nonphytotoxic solvent as an overall spray to small ponds containing water hyacinth (*Eichornia crassipes*) plants about 25 to 30 cm tall. The tests were maintained in a greenhouse and plant response ratings were taken four weeks after application. This test illustrates the utility of these compounds for the control of aquatic weeds, results being given in Table XI.

TABLE XI

| Structure | Rate kg ai/ha | Plant Response Ratings — Water Hyacinth |
|---|---|---|
| 2,5-diCl-C$_6$H$_3$-SO$_2$-NH-C(O)-NH-C(=N-C(OCH$_3$)=CH-C(OCH$_3$)=N-) | 1/32 | 9G |
| 2-Cl-C$_6$H$_4$-SO$_2$-NH-C(O)-NH-C(=N-C(OCH$_3$)=CH-C(CH$_3$)=N-) | 1/32<br>1/16 | 9G,2C<br>9C |
| (H$_3$CO-C=N-CH=C(CH$_3$)-N=C-)-NH-C(O)-NH-SO$_2$-C$_6$H$_4$-2-CH$_3$ | 1/16<br>1/8<br>1/4<br>1/2 | 9G<br>9G<br>9G,4C<br>9G,4C |
| (H$_3$CO-C=N-CH=C(CH$_3$)-N=C-)-NH-C(O)-NH-SO$_2$-C$_6$H$_3$-2,6-diCl | 1/32 | 9G,9C |
| (H$_3$CO-C=N-CH=C(CH$_3$)-N=C-)-NH-C(O)-NH-SO$_2$-C$_6$H$_4$-2-F | 1/32<br>1/16 | 9G,1C<br>9G,1C |
| (thiophen-2-yl)-SO$_2$-NH-C(O)-NH-C(=N-C(CH$_3$)=CH-C(CH$_3$)=N-) | 1/32<br>1/16 | 9G<br>9G |
| (thiophen-2-yl)-SO$_2$-NH-C(O)-NH-C(=N-C(CH$_3$)=CH-C(OCH$_3$)=N-) | 1/32<br>1/16 | 9G,5C<br>9C |
| (H$_3$C-C=N-CH=C(CH$_3$)-N=C-)-NH-C(O)-NH-SO$_2$-C$_6$H$_4$-2-Cl | 1/32<br>1/16 | 9G<br>9G,2C |
| (H$_3$CO-C=N-CH=C(OCH$_3$)-N=C-)-NH-C(O)-NH-SO$_2$-C$_6$H$_3$-2,5-(OCH$_3$)$_2$ | 1/32 | 9G |

TABLE XI-continued

| Structure | Plant Response Ratings | |
|---|---|---|
| | Rate kg ai/ha | Water Hyacinth |
| (2-methylphenyl)-SO$_2$-NH-C(=O)-NH-C(=N-C(CH$_3$)=CH-N=C-CH$_3$) (triazine with CH$_3$ substituents) | 1/32 | 9G |

PLANT GROWTH REGULANT USES

In addition to their use as herbicides, compounds of Formula I are also useful as agents to beneficially modify growth of selected plant species. Rates (usually 0.01 to 1.0 kg/ha) and timing of application are selected according to species to achieve desirable effects with a minimum of phytotoxicity. Both vegetative and reproductive growth may be controlled. Examples below illustrate the response to sugarcane, sorghum, bahia and other grasses to compounds of this invention. In sugarcane and sorghum, a "chemical ripening" effect is produced which results in a greater yield of soluble solids (mostly sugars). In many other grasses, growth and seed stalk development are restricted by these compounds which reduces mowing requirements. These compounds also are useful for growth control of woody and herbaceous broadleaf plants.

EXAMPLE A

Dwarf sugarcane plants, 6-8 months old, grown 3-5 stalks (1.5-3 meters tall) per 25 cm. pot were sprayed with the compounds given below (2 pots per compound). Each stalk was measured to the highest visible leaf collar to the start and end of the study to determine effects on growth in height. When stalks were harvested, 5 weeks after treatment, juice was extracted therefrom and soluble solids determined at the centers of the top, middle and bottom thirds of each stalk. Table XII shows that in stalks treated with compounds of this invention, soluble solids were increased and growth was restricted as compared to the solvent control (500 l/ha water plus surfactant Tween 20 ® at 0.2%).

TABLE XII

| Structure | Kg/Ha | Growth (cm) | Sections of Sugarcane Stalks | | |
|---|---|---|---|---|---|
| | | | Bottom | Middle | Top |
| 2-Cl-C$_6$H$_4$-SO$_2$-NH-C(=O)-NHC(=N-C(OCH$_3$)=CH-N=C-CH$_3$) | 0.25 | 15 | 18.2 | 17.6 | 11.1 |
| | 1.0 | 9 | 18.3 | 19.0 | 14.6 |
| 2-CH$_3$-C$_6$H$_4$-SO$_2$-NH-C(=O)-NHC(=N-C(OCH$_3$)=CH-N=C-CH$_3$) | 0.25 | 15 | 18.1 | 18.9 | 13.4 |
| | 1.0 | 6 | 19.9 | 20.4 | 15.8 |
| Solvent control | — | 40 | 16.7 | 13.8 | 6.1 |

EXAMPLE B

Tracy sweet sorghum plants grown one per 15 cm pot to a stage just prior to head emergence were sprayed with compounds given below. Visual effects were noted about 3 weeks after spraying; then at 4 weeks plants were harvested and soluble solids determined at the centers of the top. middle, and bottom thirds of each stalk. As shown in Table XIII, percent soluble solids was increased, and growth and flowering were restricted in stalks treated with compounds of this invention.

TABLE XIII
| Compound | Kg/Ha | 3-Week Response Rating[1] | Soluble Solids Expressed as % of Control Values in Various Sections of Sorghum Stalks | | |
|---|---|---|---|---|---|
| | | | Bottom | Middle | Top |
| 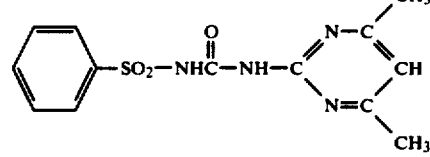 | 1.0<br>4.0 | 9G,F,2X<br>9G,F | 114<br>115 | 132<br>128 | 69 |
| 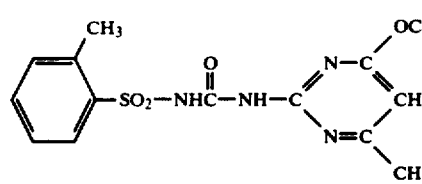 | 0.03<br>0.5 | 9G,F,3X<br>&G,F,3X | 119<br>119 | 99<br>119 | 84<br>112 |
| 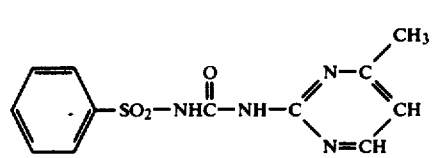 | 1.0 | 8G,F,2X | 114 | 140 | 96 |
| 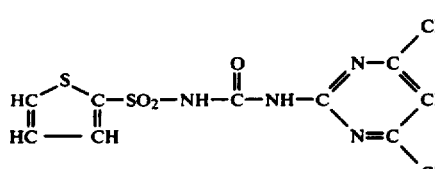 | 0.125<br>2.0 | &G,F,1C<br>&G,F | 119<br>122 | 109<br>115 | 88<br>66 |
| 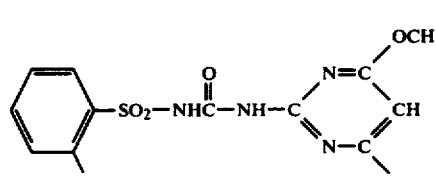 | 0.5<br>2.0 | 9G,F,2X<br>&G,F,2X | 111<br>118 | 100<br>105 | 57<br>59 |
| 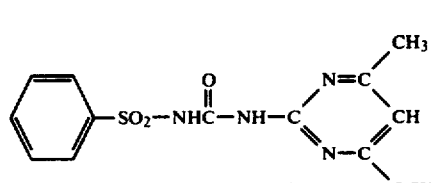 | 0.5 | 7G | 115 | 106 | 98 |
| 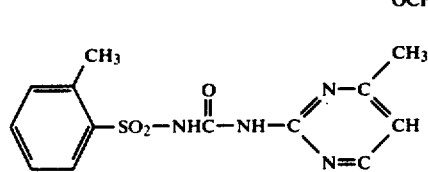 | 0.125<br>0.5 | 9G,F,1C<br>9G,F,2C | 139<br>147 | 115<br>129 | 140<br>146 |
| 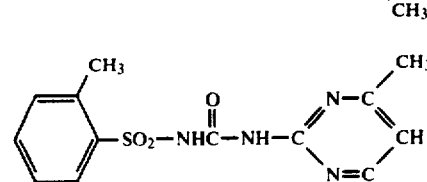 | 0.125<br>0.5 | 8G,F<br>&G,F | 113<br>120 | 113<br>113 | 114<br>121 |

TABLE XIII-continued
| Compound | Kg/Ha | 3-Week Response Rating[1] | Soluble Solids Expressed as % of Control Values in Various Sections of Sorghum Stalks | | |
|---|---|---|---|---|---|
| | | | Bottom | Middle | Top |
| 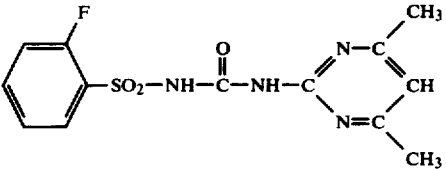 | 0.125<br>0.5 | &G,F,1C<br>&G,F,1C | 127<br>127 | 127<br>127 | 136<br>136 |
| 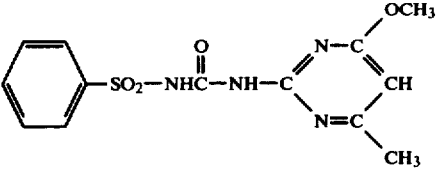 | 0.25<br>1.0 | &G,F<br>&G,F | 120<br>120 | 120<br>120 | 121<br>121 |
| 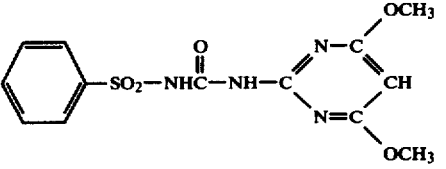 | 0.25<br>1.0 | &G,F<br>&G,F | 120<br>113 | 113<br>113 | 107<br>107 |
| 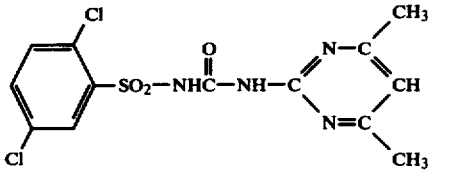 | 0.5 | 6G,F,2X | — | 122 | — |
| 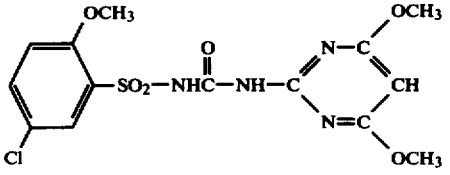 | 0.125 | 9G,F,8X | — | 130 | — |
| 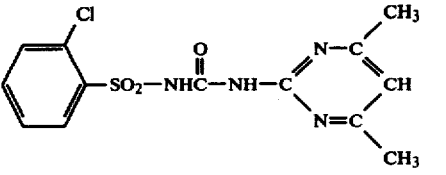 | 0.06 | 9G,F,2X | — | 139 | — |
| 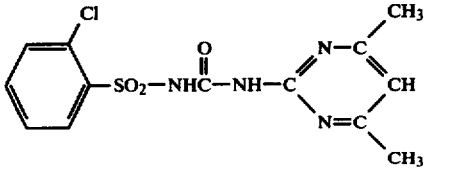 | 0.06 | &G,F,2U | — | 165 | — |
| 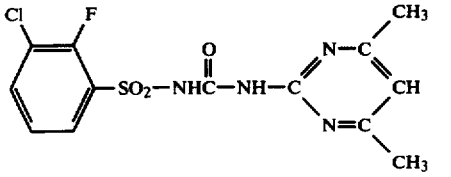 | 0.06 | &G,F,1X | — | 165 | — |

TABLE XIII-continued

| Compound | Kg/Ha | 3-Week Response Rating[1] | Soluble Solids Expressed as % of Control Values in Various Sections of Sorghum Stalks | | |
|---|---|---|---|---|---|
| | | | Bottom | Middle | Top |
| [Cl, F-phenyl-SO$_2$-NHC(O)-NH-C(=N-)(OCH$_3$)-pyrimidine with OCH$_3$, CH] | 0.25 | 0 | — | 122 | — |
| [Cl-phenyl-SO$_2$-NHC(O)-NH-C(=N-)(OCH$_3$)-pyrimidine with CH, CH$_3$] | 0.03 | &G,F,2X | 119 | 112 | 116 |
| | 0.125 | &G,F,2X | 135 | 111 | 105 |
| | 0.5 | &G,F,2X | 126 | 117 | 108 |

[1] F = flowering delayed.

EXAMPLE C

Bahia grass plants (*Paspalum notatum*, Flugge) well established in 13-cm pots, we sprayed with the compounds of Table XIV when seedheads were just ready to emerge. Plants were about 35 cm tall and 3 pots were sprayed over the top (560 lHa) with each rate. The response set forth in Table XIV were recorded 45 days after treatment. Compounds of the invention retarded growth and suppressed seedhead development.

the compounds with selectivity for two important crops, rice and wheat.

The test compounds were applied in a nonphytotoxic solvent to soil pots containing seeds of an intermediate hybrid rice, japonica rice, barnyardgrass (*Echinochloa crusgalli*), and morning glory (*Ipomoea sp.*). One compound was also applied to wheat, wild oats (*Avena fatua*), downy brome (*Bromus tectorum*), and cheat (*Bromus secalinus*). Established plantings (postemergence) of some or all of the species mentioned above

TABLE XIV

| Compound | Kg/Ha | 45-Day Response Rating[1] | Percent Seedhead Suppression |
|---|---|---|---|
| [thiophene-C-SO$_2$-NH-C(O)-NH-C(=N-)(CH$_3$)-pyrimidine with CH, CH$_3$] | 0.03 | 2G | 10 |
| | 0.125 | 2G | 30 |
| | 0.5 | 3G,2U | 90 |
| | 1.0 | 3G,2U | 100 |
| [CH$_3$-phenyl-SO$_2$-NH-C(O)-NH-C(=N-)(OCH$_3$)-pyrimidine with CH, CH$_3$] | 0.008 | 2G | 0 |
| | 0.03 | 3G | 30 |
| | 0.125 | 9G,1C,2U | 95 |
| | 0.5 | 9G,2C,2U | 95 |
| [Cl-phenyl-SO$_2$-NH-C(O)-NH-C(=N-)(OCH$_3$)-pyrimidine with CH, CH$_3$] | 0.008 | 2G | 70 |
| | 0.03 | 7G | 70 |
| | 0.125 | &G,2C,2U | 95 |
| | 0.5 | &G,3C,2U | 100 |

The following test data are presented to further illustrate the biological activity of the compounds of this invention. The data illustrate the herbicidal efficacy of were also included in the test. The plants were maintained in a greenhouse, and visual plant response ratings were generally taken about three weeks after application. The results are reported in Table XV.

TABLE XV

| COMPOUND | | Preemergence | | | | | | | | | Postemergence | | | | | | |
|---|---|---|---|---|---|---|---|---|---|---|---|---|---|---|---|---|---|
| | Kg ai/ha | Inter-med-iate Rice | Japonica Rice | Barn-yard-grass | Mor-ning glory | Wheat | Wild Oats | Bromus tectorum | Bromus secalinus | Inter-med-iate Rice | Japonica Rice | Barn-yard-grass | Mor-ning glory | Wheat | Wild Oats | Bromus tectorum | Bromus secalinus |
| ![structure with Cl, Cl, Cl substituents, SO2NHCNH, pyrimidine with CH3 and OCH3] | 1/16 | 0 | 0 | 6G | 3G | 0 | 0 | 5G | 5G | 0 | 0 | 9G | 9G | 0 | 0 | 4G | 4G |
| | 1/4 | 5G | 2G | 9C | 6G | 1G | 3G | 6G | 7G | 0 | 0 | 9G | 9G | 0 | 0 | 2G | 6G |
| ![structure with Cl, SO2NHCNH, pyridine with CH3 and OCH3] | 1/32 | 0 | 0 | 5G | 0 | | | | | — | 0 | 6G | 8G | | | | |
| | 1/8 | 9C | 7C | 9C | 8G | | | | | 0 | 0 | 9G | 10C | | | | |
| | | | | | 3C | | | | | | | 6C | | | | | |

What is claimed is:
1. A compound having the formula:

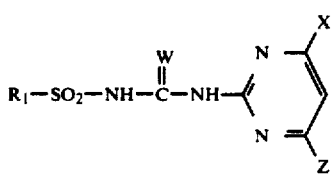

wherein
R₁ is

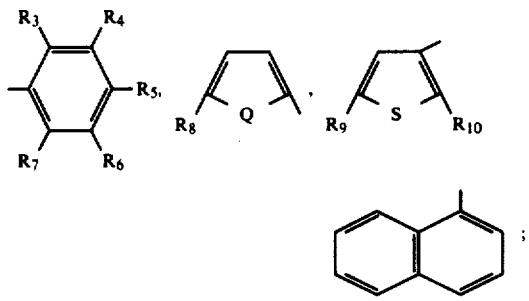

$R_3$ and $R_4$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S$— or $CH_3OCH_2$—; and Z is methyl or methoxy; or an agriculturally suitable salt thereof;

provided that:
(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;
(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and
(c) when $R_3$ and $R_7$ are both hydrogen at least one of $R_4$, $R_5$ or $R_6$ must be hydrogen.

2. A compound of claim 1 wherein
R₁ is

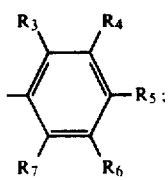

3. A compound of claim 2 wherein
$R_3$ is hydrogen, fluorine, chlorine, bromine, alkyl of 1–4 carbon atoms, alkoxy of 1–4 carbon atoms, $CH_3S$—, $CH_3CH_2S$— or nitro; and $R_5$ is hydrogen, fluorine, chlorine, bromine or methyl; and $R_6$ is hydrogen, fluorine, chlorine, bromine, alkyl of 1–4 carbon atoms, alkoxy of 1–4 carbon atoms, trifluoromethyl, nitro, $CH_3S$— or $CH_3CH_2S$—;

provided that:
(a) when $R_5$ is other than hydrogen, $R_3$, $R_6$ or $R_7$ must independently be hydrogen, fluorine, chlorine, bromine, methyl or methoxy, and $R_4$ must be hydrogen, fluorine, chlorine, bromine, or methyl.

4. A compound of claim 3 wherein
X is methyl or alkoxy having 1–3 carbon atoms; and
Z is methyl or methoxy;

5. A compound of claim 4 wherein
$R_3$ is hydrogen, fluorine, chlorine, bromine, alkyl of 1–2 carbon atoms, alkoxy of 1–2 carbon atoms, $CH_3S$—, $CH_3CH_2S$— or nitro; and $R_4$, $R_5$ and $R_7$ are independently hydrogen, fluorine, chlorine or methyl; and $R_6$ is hydrogen, fluorine, chlorine, bromine, alkyl of 1–2 carbon atoms, alkoxy of 1–2 carbon atoms, trifluoromethyl, nitro, $CH_3S$—, or $CH_3CH_2S$—.

6. A compound of claim 4 wherein
$R_3$, $R_4$, $R_5$, $R_6$ and $R_7$ are independently hydrogen, fluorine, chlorine or methyl.

7. A compound of claim 4 wherein
$R_3$ is fluorine, chlorine or methyl; and
$R_4$, $R_5$, $R_6$ and $R_7$ are independently hydrogen, fluorine, chlorine or methyl;

provided that:
when $R_5$ is other than hydrogen, $R_4$ and $R_6$ must be hydrogen.

8. A compound of claim 4 wherein
$R_3$ is fluorine, chlorine or methyl; and
$R_4$ and $R_6$ are hydrogen; and
$R_5$ and $R_7$ are independently hydrogen, fluorine, chlorine or methyl.

9. A compound of claim 4 wherein
$R_3$ is hydrogen, fluorine, chlorine, bromine, alkyl of 1–4 carbon atoms, alkoxy of 1–4 carbon atoms, $CH_3S$—, or $CH_3CH_2S$—; and $R_4$ $R_5$ and $R_7$ are hydrogen; and $R_6$ is hydrogen, fluorine, chlorine, bromine, alkyl of 1–4 carbon atoms, alkoxy of 1–4 carbon atoms, trifluoromethyl, nitro, $CH_3S$— or $CH_3CH_2S$.

10. A compound of claim 9 wherein
$R_3$ is fluorine, chlorine, bromine, alkyl of 1–2 carbon atoms or alkoxy of 1–2 carbon atoms; and $R_6$ is hydrogen, fluorine, chlorine, bromine, alkyl of 1–2 carbon atoms, alkoxy of 1–2 carbon atoms, trifluoromethyl or nitro.

11. A compound of claim 9 wherein
$R_3$ is fluorine, chlorine, bromine, methyl or methoxy; and $R_6$ is hydrogen, fluorine, chlorine, bromine, methyl, methoxy or nitro.

12. A compound of claim 5 wherein $R_3$ is nitro and each of $R_4$, $R_5$, $R_6$ and $R_7$ is hydrogen.

13. A compound of claim 1 wherein
R₁ is

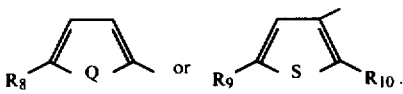

14. A compound of claim 13 wherein
Q is sulfur;
X is methyl or alkoxy of 1-3 carbon atoms; and
Z is methyl or methoxy 15. A compound of claim 13 wherein
R₁ is

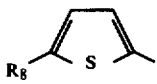

and R₈ is hydrogen.

16. A compound of claim 1 wherein
R₁ is

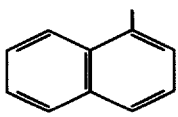

and W is oxygen.

17. A compound of claim 1 which is N-[(4-methoxy-6-methylpyrimidin-2-yl)aminocarbonyl]-2-chlorobenzenesulfonamide.

18. A compound of claim 1 which is N-[(4,6-dimethoxypyrimidin-2-yl)aminocarbonyl]-2,5-dichlorobenzenesulfonamide.

19. A compound of claim 1 which is N-[(4-methoxy-6-methylpyrimidin-2-yl)aminocarbonyl]-2-methylbenzenesulfonamide.

20. A compound of claim 1 which is N-[(4,6-dimethylpyrimidin-2-yl)aminocarbonyl]-2-thiophenesulfonamide.

21. A compound of claim 1 which is N-[(4-methoxy-6-methylpyrimidin-2-yl)aminocarbonyl]-2-chloro-5-methoxybenzenesulfonamide.

22. A compound of claim 1 which is N-[(4,6-dimethylpyrimidin-2-yl)aminocarbonyl]-2,6-dichlorobenzenesulfonamide.

23. A compound of claim 1 which is N-[(4,6-dimethylpyrimidin-2-yl)aminocarbonyl]-benzenesulfonamide.

24. A compound of claim 1 which is N-[(4-methoxy-6-methylpyrimidin-2-yl)aminocarbonyl]-2-nitrobenzenesulfonamide.

25. A compound of claim 1 which is N-[(4,6-dimethoxypyrimidin-2-yl)aminocarbonyl]-2-nitrobenzenesulfonamide.

26. A compound of claim 1 which is N-[(4-chloro-6-methylpyrimidin-2-yl)aminocarbonyl]-2-nitrobenzenesulfonamide.

27. A compound of claim 1 which is N-[(4,6-dimethylpyrimidin-2-yl)aminocarbonyl]-2-nitrobenzenesulfonamide.

28. A composition suitable for controlling the growth of undesired vegetation which comprises an effective amount of a compound of claim 1 and at least one of the following: surfactant, solid or liquid diluent.

29. A composition suitable for controlling the growth of undesired vegetation which comprises an effective amount of a compound of claim 2 and at least one of the following: surfactant, solid or liquid diluent.

30. A composition suitable for controlling the growth of undesired vegetation which comprises an effective amount of a compound of claim 3 and at least one of the following: surfactant, solid or liquid diluent.

31. A composition suitable for controlling the growtn of undesired vegetation which comprises an effective amount of a compound of claim 4 and at least one of the following: surfactant, solid or liquid diluent.

32. A composition suitable for controlling the growth of undesired vegetation which comprises an effective amount of a compound of claim 5 and at least one of the following: surfactant, solid or liquid diluent.

33. A composition suitable for controlling the growth of undesired vegetation which comprises an effective amount of a compound of claim 6 and at least one of the following: surfactant, solid or liquid diluent.

34. A composition suitable for controlling the growth of undesired vegetation which comprises an effective amount of a compound of claim 7 and at least one of the following: surfactant, solid or liquid diluent.

35. A composition suitable for controlling the growth of undesired vegetation which comprises an effective amount of a compound of claim 8 and at least one of the following: surfactant, solid or liquid diluent.

36. A composition suitable for controlling the growth of undesired vegetation which comprises an effective amount of a compound of claim 9 and at least one of the following: surfactant, solid or liquid diluent.

37. A composition suitable for controlling the growth of undesired vegetation which comprises an effective amount of a compound of claim 10 and at least one of the following: surfactant, solid or liquid diluent.

38. A composition suitable for controlling the growth of undesired vegetation which comprises an effective amount of a compound of claim 11 and at least one of the following: surfactant, solid or liuid diluent.

39. A composition suitable for controlling the growth of undesired vegetation which comprises an effective amount of a compound of claim 12 and at least one of the following: surfactant, solid or liquid diluent.

40. A composition suitable for controlling the growth of undesired vegetation wnich comprises an effective amount of a compound of claim 13 and at least one of the following: surfactant, solid or liquid diluent.

41. A composition suitable for controlling the growth of undesired vegetation which comprises an effective amount of a compound of claim 14 and at least one of the following: surfactant, solid or liquid diluent.

42. A composition suitable for controlling the growth of undesired vegetation which comprises an effective amount of a compound of claim 15 and at least one of the following: surfactant, solid or liquid diluent.

43. A composition suitable for controlling the growth of undesired vegetation which comprises an effective amount of a compound of claim 16 and at least one of the following: surfactant, solid or liquid diluent.

44. A composition suitable for controlling the growth of undesired vegetation which comprises an effective amount of the compound of claim 17 and at least one of the following: surfactant, solid or liquid diluent.

45. A composition suitable for controlling the growth of undesired vegetation which comprises an effective amount of the compound of claim 18 and at least one of the following: surfactant, solid or liquid diluent.

46. A composition suitable for controlling the growth of undesired vegetation which comprises an effective amount of the compound of claim 19 and at least one of the following: surfactant, solid or liquid diluent.

47. A composition suitable for controlling the growth of undesired vegetation which comprises an effective amount of the compound of claim 20 and at least one of the following: surfactant, solid or liquid diluent.

48. A composition suitable for controlling the growth of undesired vegetation which comprises an effective amount of the compound of claim 21 and at least one of the following: surfactant, solid or liquid diluent.

49. A composition suitable for controlling the growth of undesired vegetation which comprises an effective amount of the compound of claim 22 and at least one of the following: surfactant, solid or liquid diluent.

50. A composition suitable for controlling the growth of undesired vegetation which comprises an effective amount of the compound of claim 23 and at least one of the following: surfactant, solid or liquid diluent.

51. A composition suitable for controlling the growth of undesired vegetation which comprises an effective amount of the compound of claim 24 and at least one of the following: surfactant, solid or liquid diluent.

52. A composition suitable for controlling the growth of undesired vegetation which comprises an effective amount of the compound of claim 25 and at least one of the following: surfactant, solid or liquid diluent.

53. A composition suitable for controlling the growth of undesired vegetation which comprises an effective amount of the compound of claim 26 and at least one of the following: surfactant, solid or liquid diluent.

54. A composition suitable for controlling the growth of undesired vegetation which comprises an effective amount of the compound of claim 27 and at least one of the following: surfactant, solid or liquid diluent.

55. A composition suitable for use as a growth regulant which comprises an effective amount of a compound of claim 1 and at least one of the following: surfactant, solid or liquid diluent.

56. A composition suitable for use as a growth regulant which comprises an effective amount of a compound of claim 9 and at least one of the following: surfactant, solid or liquid diluent.

57. A composition suitable for use as a growth regulant which comprises an effective amount of the compound of claim 18 and at least one of the following: surfactant, solid or liquid diluent.

58. A composition suitable for use as a growth regulant which comprises an effective amount of the compound of claim 23 and at least one of the following: surfactant, solid or liquid diluent.

59. A method for controlling the growth of undesired vegetation which comprises applying to the locus to be protected an effective amount of a compound of claim 1.

60. A method for controlling the growth of undesired vegetation which comprises applying to the locus to be protected an effective amount of a compound of claim 2.

61. A method for controlling the growth of undesired vegetation which comprises applying to the locus to be protected an effective amount of a compound of claim 3.

62. A method for controlling the growth of undesired vegetation which comprises applying to the locus to be protected an effective amount of a compound of claim 4.

63. A method for controlling the growth of undesired vegetation which comprises applying to the locus to be protected an effective amount of a compound of claim 5.

64. A method for controlling the growth of undesired vegetation which comprises applying to the locus to be protected an effective amount of a compound of claim 6.

65. A method for controlling the growth of undesired vegetation which comprises applying to the locus to be protected an effective amount of a compound of claim 7.

66. A method for controlling the growth of undesired vegetation which comprises applying to the locus to be protected an effective amount of a compound of claim 8.

67. A method for controlling the growth of undesired vegetation which comprises applying to the locus to be protected an effective amount of a compound of claim 9.

68. A method for controlling the growth of undesired vegetation which comprises applying the the locus to be protected an effective amount of a compound of claim 10.

69. A method for controlling the growth of undesired vegetation which comprises applying to the locus to be protected an effective amount of a compound of claim 11.

70. A method for controlling the growth of undesired vegetation which comprises applying to the locus to be protected an effective amount of a compound of claim 12.

71. A method for controlling the growth of undesired vegetation which comprises applying to the locus to be protected an effective amount of a compound of claim 13.

72. A method for controlling the growth of undesired vegetation which comprises applying to the locus to be protected an effective amount of a compound of claim 14.

73. A method for controlling the growth of undesired vegetation which comprises applying to the locus to be protected an effective amount of a compound of claim 15.

74. A method for controlling the growth of undesired vegetation which comprises applying to the locus to be protected an effective amount of a compound of claim 16.

75. A method for controlling the growth of undesired vegetation which comprises applying to the locus to be protected an effective amount of the compound of claim 17.

76. A method for controlling the growth of undesired vegetation which comprises applying to the locus to be protected an effective amount of the compound of claim 18.

77. A method for controlling the growth of undesired vegetation which comprises applying to the locus to be protected an effective amount of the compound of claim 19.

78. A method for controlling the growth of undesired vegetation which comprises applying to the locus to be protected an effective amount of the compound of claim 20.

79. A method for controlling the growth of undesired vegetation which comprises applying to the locus to be protected an effective amount of the compound of claim 21.

80. A method for controlling the growth of undesired vegetation which comprises applying to the locus to be protected an effective amount of the compound of claim 22.

81. A method for controlling the growth of undesired vegetation which comprises applying to the locus to be protected an effective amount of the compound of claim 23.

82. A method for controlling the growth of undesired vegetation which comprises applying to the locus to be protected an effective amount of the compound of claim 24.

83. A method for controlling the growth of undesired vegetation which comprises applying to the locus to be protected an effective amount of the compound of claim 25.

84. A method for controlling the growth of undesired vegetation which comprises applying to the locus to be protected an effective amount of the compound of claim 26.

85. A method for controlling the growth of undesired vegetation which comprises applying to the locus to be protected an effective amount of the compound of claim 27.

86. A method for selectively controlling the growth of nutsedge, *Cyperus, spp.*, in crops which comprises applying to the locus of the area to be controlled an effective amount of a compound of claim 1.

87. A method for selectively controlling the growth of nutsedge, *Cyperus, spp.*, in crops which comprises applying to the locus of the area to be controlled an effective amount of a compound of claim 2.

88. A method for selectively controlling the growth of nutsedge, *Cyperus, spp.*, in crops which comprises applying to the locus of the area to be controlled an effective amount of a compound of claim 3.

89. A method for selectively controlling the growth of nutsedge, *Cyperus, spp.*, in crops which comprises applying to the locus of the area to be controlled an effective amount of a compound of claim 4.

90. A method for selectively controlling the growth of nutsedge, *Cyperus, spp.*, in crops which comprises applying to the locus of the area to be controlled an effective amount of a compound of claim 5.

91. A method for selectively controlling the growth of nutsedge, *Cyperus, spp.*, in crops which comprises applying to the locus of the area to be controlled an effective amount of a compound of claim 6.

92. A method for selectively controlling the growth of nutsedge, *Cyperus, spp.*, in crops which comprises applying to the locus of the area to be controlled an effective amount of a compound of claim 7.

93. A method for selectively controlling the growth of nutsedge, *Cyperus, spp.*, in crops which comprises applying to the locus of the area to be controlled an effective amount of a compound of claim 8.

94. A method for selectively controlling the growth of nutsedge, *Cyperus, spp.*, in crops which comprises applying to the locus of the area to be controlled an effective amount of a compound of claim 9.

95. A method for selectively controlling the growth of nutsedge, *Cyperus, spp.*, in crops which comprises applying to the locus of the area to be controlled an effective amount of a compound of claim 10.

96. A method for selectively controlling the growth of nutsedge, *Cyperus, spp.*, in crops which comprises applying to the locus of the area to be controlled an effective amount of a compound of claim 11.

97. A method for selectively controlling the growth of nutsedge, *Cyperus, spp.*, in crops which comprises applying to the locus of the area to be controlled an effective amount of a compound of claim 12.

98. A method for selectively controlling the growth of nutsedge, *Cyperus, spp.*, in crops which comprises applying to the locus of the area to be controlled an effective amount of a compound of claim 13.

99. A method for selectively controlling the growth of nutsedge, *Cyperus, spp.*, in crops which comprises applying to the locus of the area to be controlled an effective amount of a compound of claim 14.

100. A method for selectively controlling the the growth of nutsedge, *Cyperus, spp.*, in crops which comprises applying to the locus of the area to be controlled an effective amount of a compound of claim 15.

101. A method for selectively controlling the growth of nutsedge, *Cyperus, spp.*, in crops which comprises applying to the locus of the area to be controlled an effective amount of a compound of claim 16.

102. A method for selectively controlling the growth of nutsedge, *Cyperus, spp.*, in crops which comprises applying to the locus of the area to be controlled an effective amount of the compound of claim 18.

103. A method for selectively controlling the growth of nutsedge, *Cyperus, spp.*, in crops which comprises applying to the locus of the area to be controlled an effective amount of the compound of claim 22.

104. A method for selectively controlling the growth of undesired vegetation in wheat comprising applying to the locus of such undesired vegetation an effective amount of a compound of claim 1.

105. A method for selectively controlling the growth of undesired vegetation in wheat comprising applying to the locus of such undesired vegetation an effective amount of the compound of claim 2.

106. A method for selectively controlling the growth of undesired vegetation in wheat comprising applying to the locus of such undesired vegetation an effective amount of the compound of claim 3.

107. A method for selectively controlling the growth of undesired vegetation in wheat comprising applying to the locus of such undesired vegetation an effective amount of the compound of claim 4.

108. A method for selectively controlling the growth of undesired vegetation in wheat comprising applying to the locus of such undesired vegetation an effective amount of the compound of claim 5.

109. A method for selectively controlling the growth of undesired vegetation in wheat, comprising applying to the locus of such undesired vegetation an effective amount of a compound of claim 6.

110. A method for selectively controlling the growth of undesired vegetation in wheat, comprising applying to the locus of such undesired vegetation an effective amount of a compound of claim 7.

111. A method for selectively controlling the growth of undesired vegetation in wheat, comprising applying to the locus of such undesired vegetation an effective amount of a compound of claim 8.

112. A method for selectively controlling the growth of undesired vegetation in wheat, comprising applying to the locus of such undesired vegetation an effective amount of a compound of claim 9.

113. A method for selectively controlling the growth of undesired vegetation in wheat, comprising applying to the locus of such undesired vegetation an effective amount of a compound of claim 10.

114. A method for selectively controlling the growth of undesired vegetation in wheat, comprising applying to the locus of such undesired vegetation an effective amount of a compound of claim 11.

115. A method for selectively controlling the growth of undesired vegetation in wheat, comprising applying to the locus of such undesired vegetation an effective amount of a compound of claim 13.

116. A method for selectively controlling the growth of undesired vegetation in wheat, comprising applying to the locus of such undesired vegetation an effective amount of a compound of claim 14.

117. A method for selectively controlling the growth of undesired vegetation in wheat, comprising applying to the locus of such undesired vegetation an effective amount of a compound of claim 15.

118. A method for selectively controlling the growth of undesired vegetation in wheat, comprising applying to the locus of such undesired vegetation an effective amount of a compound of claim 16.

119. A method for selectively controlling the growth of undesired vegetation in wheat which comprises applying to the locus of the undesired vegetation an effective amount of the compound of claim 21.

120. A method for controlling the growth of water hyacinth which comprises applying thereto an effective amount of a compound of claim 1.

121. A method for controlling the growth of water hyacinth which comprises applying thereto an effective amount of a compound of claim 9.

122. A method for controlling the growth of water hyacinth which comprises applying thereto an effective amount of the compound of claim 17.

123. A method for regulating the growth of vegetation which comprises applying to the locus of the vegetation an effective amount of a compound of claim 1.

124. A method for regulating the growth of vegetation which comprises applying to the locus of the vegetation an effective amount of a compound of claim 9.

125. A method for regulating the growth of vegetation which comprises applying to the locus of the vegetation an effective amount of the compound of claim 18.

126. A method for regulating the growth of vegetation which comprises applying to the locus of the vegetation an effective amount of the compound of claim 23.

* * * * *